US012721915B2

(12) United States Patent
Ludwig et al.

(10) Patent No.: US 12,721,915 B2
(45) Date of Patent: Sep. 1, 2026

(54) HER3 RADIOIMMUNOTHERAPY FOR THE TREATMENT OF SOLID CANCERS

(71) Applicant: ACTINIUM PHARMACEUTICALS, INC., New York, NY (US)

(72) Inventors: Dale L Ludwig, Rockaway, NJ (US); Eileen Geoghegan, Mamaroneck, NY (US); Sandesh Seth, New York, NY (US); Paul Diamond, Fort Lee, NJ (US)

(73) Assignee: ACTINIUM PHARMACEUTICALS, INC., New York, NY (US)

( * ) Notice: Subject to any disclaimer, the term of this patent is extended or adjusted under 35 U.S.C. 154(b) by 1278 days.

(21) Appl. No.: 17/532,919

(22) Filed: Nov. 22, 2021

(65) Prior Publication Data

US 2022/0143228 A1 May 12, 2022

Related U.S. Application Data

(63) Continuation-in-part of application No. PCT/US2021/056259, filed on Oct. 22, 2021.

(60) Provisional application No. 63/250,725, filed on Sep. 30, 2021, provisional application No. 63/226,699, filed on Jul. 28, 2021, provisional application No. 63/118,181, filed on Nov. 25, 2020, provisional application No. 63/116,225, filed on Nov. 20, 2020, provisional application No. 63/104,386, filed on Oct. 22, 2020.

(51) Int. Cl.

| | |
|---|---|
| ***A61K 51/10*** | (2006.01) |
| ***A61K 9/00*** | (2006.01) |
| ***A61K 31/454*** | (2006.01) |
| ***A61K 31/502*** | (2006.01) |
| ***A61K 31/5025*** | (2006.01) |
| ***A61K 31/55*** | (2006.01) |
| ***A61K 39/395*** | (2006.01) |

(52) U.S. Cl.

CPC .......... *A61K 51/103* (2013.01); *A61K 9/0019* (2013.01); *A61K 9/0053* (2013.01); *A61K 31/454* (2013.01); *A61K 31/502* (2013.01); *A61K 31/5025* (2013.01); *A61K 31/55* (2013.01); *A61K 39/3955* (2013.01); *A61K 51/1093* (2013.01)

(58) Field of Classification Search

None

See application file for complete search history.

(56) References Cited

U.S. PATENT DOCUMENTS

| | | | | |
|---|---|---|---|---|
| 4,923,985 | A | 5/1990 | Gansow | |
| 7,705,130 | B2 | 4/2010 | Rothe | |
| 7,834,019 | B2 | 11/2010 | Sagara | |
| 7,846,440 | B2 | 12/2010 | Schoeberl | |
| 7,935,708 | B2 | 5/2011 | Sagara | |
| 8,236,313 | B2 | 8/2012 | Isenberg | |
| 8,288,396 | B2 | 10/2012 | Goto | |
| 8,436,004 | B2 | 5/2013 | Bamba | |
| 8,557,788 | B2 | 10/2013 | Isenberg | |
| 8,597,652 | B2 | 12/2013 | Fuh | |
| 8,710,065 | B2 | 4/2014 | Tong | |
| 8,716,297 | B2 | 5/2014 | Woods | |
| 8,791,125 | B2 | 7/2014 | Sagara | |
| 8,796,289 | B2 | 8/2014 | Zhu | |
| 8,961,966 | B2 | 2/2015 | Schoeberl | |
| 9,051,327 | B2 | 6/2015 | Zhu | |
| 9,181,239 | B2 | 11/2015 | Mastracchio | |
| 9,249,230 | B2 | 2/2016 | Rothe | |
| 9,327,035 | B2 | 5/2016 | Fuh | |
| 9,714,244 | B2 | 7/2017 | O'Dowd | |
| 9,718,821 | B2 | 8/2017 | Woods | |
| 9,850,247 | B2 | 12/2017 | Harrison | |
| 9,969,789 | B2 | 5/2018 | Uger | |
| 10,370,439 | B2 | 8/2019 | Isenberg | |
| 10,413,607 | B2 | 9/2019 | Bae | |
| 10,519,247 | B2 * | 12/2019 | Ward | ...................... A61P 35/00 |
| 10,662,241 | B1 | 5/2020 | Boyd-Kirkup | |
| 10,736,975 | B2 | 8/2020 | Dave | |
| 11,000,604 | B2 | 5/2021 | Zeglis | |

(Continued)

FOREIGN PATENT DOCUMENTS

| | | | |
|---|---|---|---|
| WO | 2002/090360 | A1 | 11/2002 |
| WO | 2005/117973 | A2 | 12/2005 |

(Continued)

OTHER PUBLICATIONS

MacCallum et al. (1996). J. Mol. Biol. 262:732-745.*

(Continued)

*Primary Examiner* — Christine J Saoud
*Assistant Examiner* — Jon M Lockard
(74) *Attorney, Agent, or Firm* — Michael E. Dukes; Dentons Cohen & Grigsby, P.C.

(57) ABSTRACT

Provided are compositions and methods for treating a solid cancer such as a HER3-positive tumor in a subject by administering an effective amount of a HER3-targeting agent labeled with a radionuclide such as $^{225}$Ac, $^{177}$Lu, $^{131}$I, $^{90}$Y, $^{213}$Bi, $^{211}$At, $^{213}$Bi, $^{227}$Th, or $^{212}$Pb, alone or in combination with other therapeutic agents or modalities. The effective amount of the radiolabeled HER3-targeting agent may be a maximum tolerate dose administered in a single bolus or in fractionated doses that together equal the maximum tolerated dose.

32 Claims, 12 Drawing Sheets

Specification includes a Sequence Listing.

(Continued)

(56) References Cited

U.S. PATENT DOCUMENTS

| | | | |
|---|---|---|---|
| 2009/0246206 | A1 | 10/2009 | Nielsen |
| 2010/0113445 | A1 | 5/2010 | Deanda |
| 2010/0239579 | A1 | 9/2010 | Smith |
| 2013/0183311 | A1 | 7/2013 | Nielsen |
| 2014/0193414 | A1 | 7/2014 | Fuh |
| 2016/0222459 | A1 | 8/2016 | Keating |
| 2016/0303232 | A1 | 10/2016 | Adiwijaya |
| 2017/0037145 | A1 | 2/2017 | Geuijen |
| 2017/0058035 | A1 | 3/2017 | Logtenberg |
| 2018/0193477 | A1 | 7/2018 | Ng |
| 2018/0362443 | A1 | 12/2018 | LaVallee |
| 2019/0300624 | A1 | 10/2019 | Boyd-Kirkup |
| 2020/0102393 | A1 | 4/2020 | Throsby |
| 2020/0121814 | A1 | 4/2020 | Mahmood |
| 2020/0276307 | A1 | 9/2020 | Daly |
| 2020/0308275 | A1 | 10/2020 | Boyd-Kirkup |
| 2021/0024651 | A1 | 1/2021 | Boyd-Kirkup |
| 2021/0155698 | A1 | 5/2021 | Logtenberg |
| 2021/0206875 | A1 | 7/2021 | Throsby |
| 2021/0246206 | A1 | 8/2021 | Liu |

FOREIGN PATENT DOCUMENTS

| | | | | |
|---|---|---|---|---|
| WO | 2006/091209 A2 | 8/2006 | | |
| WO | 2007/077028 A2 | 7/2007 | | |
| WO | 2008/060785 A2 | 5/2008 | | |
| WO | 2008/100624 A2 | 8/2008 | | |
| WO | WO-2009033743 A1 * | 3/2009 | .............. | A61P 25/28 |
| WO | 2010/108127 A1 | 9/2010 | | |
| WO | 2011/143624 A2 | 11/2011 | | |
| WO | 2015/019037 A1 | 2/2015 | | |
| WO | 2016/187514 A1 | 11/2016 | | |
| WO | 2017/013436 A1 | 1/2017 | | |
| WO | 2017/015007 A1 | 1/2017 | | |
| WO | 2017/155937 A1 | 9/2017 | | |
| WO | 2017/216559 A1 | 12/2017 | | |
| WO | 2018/011569 A1 | 1/2018 | | |
| WO | 2018/011570 A1 | 1/2018 | | |
| WO | 2019/185164 A1 | 10/2019 | | |
| WO | 2019/185878 A1 | 10/2019 | | |
| WO | 2020/132672 A1 | 6/2020 | | |
| WO | 2022/109404 A1 | 5/2022 | | |

OTHER PUBLICATIONS

De Pascalis et al. (2002). Journal of Immunology. 169:3076-3084.*

Casset et al. (2003). Biochemical and Biophysical Research Communications. 307:198-205.*

Chen et al. (1999). J. Mol. biol. 293:865-881.*

Wu et al. (1999). J. Mol. Biol. 294:151-162.*

Rudikoff et al. (1982). PNAS. 79:1979-1983.*

Meneses-Lorente G, Friess T, Kolm I, et al. Preclinical pharmacokinetics, pharmacodynamics, and efficacy of RG7116: a novel humanized, glycoengineered anti-HER3 antibody. Cancer Chemother Pharmacol. 2015;75(4):837-850.

Meulendijks D, Jacob W, Martinez-Garcia M, et al. First-in-Human Phase I Study of Lumretuzumab, a Glycoengineered Humanized Anti-HER3 Monoclonal Antibody, in Patients with Metastatic or Advanced HER3-Positive Solid Tumors. Clin Cancer Res. 2016;22(4):877-885.

Mirschberger C, Schiller CB, Schraml M, et al. RG7116, a Therapeutic Antibody That Binds the Inactive HER3 Receptor and Is Optimized for Immune Effector Activation. Cancer Res. 2013;73(16):5183-5194.

Mishra R, Patel H, Alanazi S, Yuan L, Garrett Jt. HER3 signaling and targeted therapy in cancer. Oncol Rev. 2018;12(1).

Reynolds KL, Bedard PL, Lee S-H, et al. A phase I open-label dose-escalation study of the anti-HER3. Monoclonal antibody LJM716 in patients with advanced squamous cell carcinoma of the esophagus or head and neck and HER2-overexpressing breast or gastric cancer. BMC Cancer. 2017;17(1):646.

International Search Report issued Mar. 25, 2022 in Int'l App. No. PCT/US21/60370 (filed Nov. 22, 2021).

International Preliminary Report on Patentability issued Mar. 25, 2022 in Int'l App. No. PCT/US21/60370 (filed Nov. 22, 2021).

* cited by examiner

| SEQ ID NO | AMINO ACID SEQUENCE |
|---|---|
| 1 | SHWLH<br>Heavy Chain CDR 1 |
| 2 | VLDPSDFYSNYNQNFKG<br>Heavy Chain CDR 2 |
| 3 | GLLSGDYAMDY<br>Heavy Chain CDR 3 |
| 4 | RSSQSIVHSNGNTYLE<br>Light Chain CDR 1 |
| 5 | KVSNRFS<br>Light Chain CDR 2 |
| 6 | FQGSYVPWT<br>Light Chain CDR 3 |
| 7 | QVQLQQPGAE LVRPGTSVKL SCKASGYTFT **SHWLH**WVKQR PGQGLEWIG**V LDPSDFYSNY**<br>**NQNFKG**KATL TVDTSSSTAY MQLSSLTSED SAVYYCAR**GL LSGDYAMDY**W GAGTSVTVSS<br>Heavy Chain Variable Region |
| 8 | DVLMTQIPLS LPVSLGDQAS ISC**RSSQSIV HSNGNTYLE**W YLQKPGQSPK SLIY**KVSNRF**<br>**S**GVPDRFSGS GSGTDFTLKI SRVEAEDLGV YYC**FQGSYVP WT**FGGGTKLE IK<br>Light Chain Variable Region |
| 13 | QVQLQQPGAE<br>Heavy Chain N-terminal Region |
| 14 | DVLMTQIPLS<br>Light Chain N-terminal Region |

FIG. 1

| SEQ ID NO | AMINO ACID SEQUENCE |
|---|---|
| 9 | MGWSCIIVLL VSTATGVHSQ VQLQQPGAEL VRPGTSVKLS CKASGYTFTS HWLHWVKQRP GQGLEWIGVL DPSDFYSNYN QNFKGKATLT VDTSSSTAYM QLSSLTSEDS AVYYCARGLL SGDYAMDYWG QGTSVTVSSA KTTPPSVYPL APGSAAQTNS MVTLGCLVKG YFPEPVTVTW NSGSLSSGVH TFPAVLQSDL YTLSSSVTVP SSTWPSQTVT CNVAHPASST KVDKKIVPRD CGCKPCICTV PEVSSVFIFP PKPKDVLTIT LTPKVTCVVV DISKDDPEVQ FSWFVDDVEV HTAQTQPREE QFNSTFRSVS ELPIMHQDWL NGKEFKCRVN SAAFPAPIEK TISKTKGRPK APQVYTIPPP KEQMAKDKVS LTCMITDFFP EDITVEWQWN GQPAENYKNT QPIMDTDGSY FVYSKLNVQK SNWEAGNTFT CSVLHEGLHN HHTEKSLSHS PGK<br>Full Length Heavy Chain with Leader Sequence |
| 10 | MKLPVRLLVL MFWIPASSSD VLMTQIPLSL PVSLGDQASI SCRSSQSIVH SNGNTYLEWY LQKPGQSPKS LIYKVSNRFS GVPDRFSGSG SGTDFTLKIS RVEAEDLGVY YCFQGSYVPW TFGGGTKLEI KRADAAPTVS IFPPSSEQLT SGGASVVCFL NNFYPRDINV KWKIDGSERQ NGVLNSWTDQ DSKDSTYSMS STLTLTKDEY ERHNSYTCEA THKTSTSPIV KSFNRNEC<br>Full Length Light Chain with Leader Sequence |
| 11 | QVQLQQPGAE LVRPGTSVKL SCKASGYTFT SHWLHWVKQR PGQGLEWIGV LDPSDFYSNY NQNFKGKATL TVDTSSSTAY MQLSSLTSED SAVYYCARGL LSGDYAMDYW GQGTSVTVSS AKTTPPSVYP LAPGSAAQTN SMVTLGCLVK GYFPEPVTVT WNSGSLSSGV HTFPAVLQSD LYTLSSSVTV PSSTWPSQTV TCNVAHPASS TKVDKKIVPR DCGCKPCICT VPEVSSVFIF PPKPKDVLTI TLTPKVTCVV VDISKDDPEV QFSWFVDDVE VHTAQTQPRE EQFNSTFRSV SELPIMHQDW LNGKEFKCRV NSAAFPAPIE KTISKTKGRP KAPQVYTIPP PKEQMAKDKV SLTCMITDFF PEDITVEWQW NGQPAENYKN TQPIMDTDGS YFVYSKLNVQ KSNWEAGNTF TCSVLHEGLH NHHTEKSLSH SPGK<br>Full Length Heavy Chain Sequence |
| 12 | DVLMTQIPLS LPVSLGDQAS ISCRSSQSIV HSNGNTYLEW YLQKPGQSPK SLIYKVSNRF SGVPDRFSGS GSGTDFTLKI SRVEAEDLGV YYCFQGSYVP WTFGGGTKLE IKRADAAPTV SIFPPSSEQL TSGGASVVCF LNNFYPRDIN VKWKIDGSER QNGVLNSWTD QDSKDSTYSM SSTLTLTKDE YERHNSYTCE ATHKTSTSPI VKSFNRNEC<br>Full Length Light Chain Sequence |

FIG. 2

SEQUENCE LISTING

```
<160> NUMBER OF SEQ ID NOS: 118

<210> SEQ ID NO 1
<211> LENGTH: 5
<212> TYPE: PRT
<213> ORGANISM: Mus musculus

<400> SEQUENCE: 1

Ser His Trp Leu His
1               5


<210> SEQ ID NO 2
<211> LENGTH: 17
<212> TYPE: PRT
<213> ORGANISM: Mus musculus

<400> SEQUENCE: 2

Val Leu Asp Pro Ser Asp Phe Tyr Ser Asn Tyr Asn Gln Asn Phe Lys
1               5                   10                  15

Gly


<210> SEQ ID NO 3
<211> LENGTH: 11
<212> TYPE: PRT
<213> ORGANISM: mus musculus

<400> SEQUENCE: 3

Gly Leu Leu Ser Gly Asp Tyr Ala Met Asp Tyr
1               5                   10


<210> SEQ ID NO 4
<211> LENGTH: 16
<212> TYPE: PRT
<213> ORGANISM: mus musculus

<400> SEQUENCE: 4

Arg Ser Ser Gln Ser Ile Val His Ser Asn Gly Asn Thr Tyr Leu Glu
1               5                   10                  15


<210> SEQ ID NO 5
<211> LENGTH: 7
<212> TYPE: PRT
```

<213> ORGANISM: mus musculus

<400> SEQUENCE: 5

Lys Val Ser Asn Arg Phe Ser
1 5

<210> SEQ ID NO 6
<211> LENGTH: 9
<212> TYPE: PRT
<213> ORGANISM: mus musculus

<400> SEQUENCE: 6

Phe Gln Gly Ser Tyr Val Pro Trp Thr
1 5

<210> SEQ ID NO 7
<211> LENGTH: 120
<212> TYPE: PRT
<213> ORGANISM: mus musculus

<400> SEQUENCE: 7

Gln Val Gln Leu Gln Gln Pro Gly Ala Glu Leu Val Arg Pro Gly Thr
1 5 10 15

Ser Val Lys Leu Ser Cys Lys Ala Ser Gly Tyr Thr Phe Thr Ser His
20 25 30

Trp Leu His Trp Val Lys Gln Arg Pro Gly Gln Gly Leu Glu Trp Ile
35 40 45

Gly Val Leu Asp Pro Ser Asp Phe Tyr Ser Asn Tyr Asn Gln Asn Phe
50 55 60

Lys Gly Lys Ala Thr Leu Thr Val Asp Thr Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Gly Leu Leu Ser Gly Asp Tyr Ala Met Asp Tyr Trp Gly Ala
100 105 110

Gly Thr Ser Val Thr Val Ser Ser
115 120

<210> SEQ ID NO 8
<211> LENGTH: 112
<212> TYPE: PRT
<213> ORGANISM: mus musculus

<400> SEQUENCE: 8

Asp Val Leu Met Thr Gln Ile Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Ser Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser Tyr Val Pro Trp Thr Phe Gly Gly Gly Thr Lys Leu Glu Ile Lys
100 105 110

<210> SEQ ID NO 9
<211> LENGTH: 463
<212> TYPE: PRT
<213> ORGANISM: mus musculus

<400> SEQUENCE: 9

Met Gly Trp Ser Cys Ile Ile Val Leu Leu Val Ser Thr Ala Thr Gly
1 5 10 15

Val His Ser Gln Val Gln Leu Gln Gln Pro Gly Ala Glu Leu Val Arg
20 25 30

Pro Gly Thr Ser Val Lys Leu Ser Cys Lys Ala Ser Gly Tyr Thr Phe
35 40 45

Thr Ser His Trp Leu His Trp Val Lys Gln Arg Pro Gly Gln Gly Leu
50 55 60

Glu Trp Ile Gly Val Leu Asp Pro Ser Asp Phe Tyr Ser Asn Tyr Asn
65 70 75 80

Gln Asn Phe Lys Gly Lys Ala Thr Leu Thr Val Asp Thr Ser Ser Ser
85 90 95

Thr Ala Tyr Met Gln Leu Ser Ser Leu Thr Ser Glu Asp Ser Ala Val
100 105 110

Tyr Tyr Cys Ala Arg Gly Leu Leu Ser Gly Asp Tyr Ala Met Asp Tyr
115 120 125

Trp Gly Gln Gly Thr Ser Val Thr Val Ser Ser Ala Lys Thr Thr Pro
130 135 140

Pro Ser Val Tyr Pro Leu Ala Pro Gly Ser Ala Ala Gln Thr Asn Ser
145 150 155 160

Met Val Thr Leu Gly Cys Leu Val Lys Gly Tyr Phe Pro Glu Pro Val
165 170 175

Thr Val Thr Trp Asn Ser Gly Ser Leu Ser Ser Gly Val His Thr Phe
180 185 190

Pro Ala Val Leu Gln Ser Asp Leu Tyr Thr Leu Ser Ser Ser Val Thr
195 200 205

Val Pro Ser Ser Thr Trp Pro Ser Gln Thr Val Thr Cys Asn Val Ala
210 215 220

His Pro Ala Ser Ser Thr Lys Val Asp Lys Lys Ile Val Pro Arg Asp
225 230 235 240

Cys Gly Cys Lys Pro Cys Ile Cys Thr Val Pro Glu Val Ser Ser Val
245 250 255

Phe Ile Phe Pro Pro Lys Pro Lys Asp Val Leu Thr Ile Thr Leu Thr
260 265 270

Pro Lys Val Thr Cys Val Val Val Asp Ile Ser Lys Asp Asp Pro Glu
275 280 285

Val Gln Phe Ser Trp Phe Val Asp Asp Val Glu Val His Thr Ala Gln
290 295 300

Thr Gln Pro Arg Glu Glu Gln Phe Asn Ser Thr Phe Arg Ser Val Ser
305 310 315 320

Glu Leu Pro Ile Met His Gln Asp Trp Leu Asn Gly Lys Glu Phe Lys
325 330 335

Cys Arg Val Asn Ser Ala Ala Phe Pro Ala Pro Ile Glu Lys Thr Ile
340 345 350

Ser Lys Thr Lys Gly Arg Pro Lys Ala Pro Gln Val Tyr Thr Ile Pro
355 360 365

Pro Pro Lys Glu Gln Met Ala Lys Asp Lys Val Ser Leu Thr Cys Met
370 375 380

Ile Thr Asp Phe Phe Pro Glu Asp Ile Thr Val Glu Trp Gln Trp Asn
385 390 395 400

Gly Gln Pro Ala Glu Asn Tyr Lys Asn Thr Gln Pro Ile Met Asp Thr
405 410 415

Asp Gly Ser Tyr Phe Val Tyr Ser Lys Leu Asn Val Gln Lys Ser Asn
420 425 430

Trp Glu Ala Gly Asn Thr Phe Thr Cys Ser Val Leu His Glu Gly Leu
435 440 445

His Asn His His Thr Glu Lys Ser Leu Ser His Ser Pro Gly Lys
450 455 460

<210> SEQ ID NO 10
<211> LENGTH: 238
<212> TYPE: PRT
<213> ORGANISM: mus musculus

<400> SEQUENCE: 10

Met Lys Leu Pro Val Arg Leu Leu Val Leu Met Phe Trp Ile Pro Ala
1 5 10 15

Ser Ser Ser Asp Val Leu Met Thr Gln Ile Pro Leu Ser Leu Pro Val
20 25 30

Ser Leu Gly Asp Gln Ala Ser Ile Ser Cys Arg Ser Ser Gln Ser Ile
35 40 45

Val His Ser Asn Gly Asn Thr Tyr Leu Glu Trp Tyr Leu Gln Lys Pro
50 55 60

Gly Gln Ser Pro Lys Ser Leu Ile Tyr Lys Val Ser Asn Arg Phe Ser
65 70 75 80

Gly Val Pro Asp Arg Phe Ser Gly Ser Gly Ser Gly Thr Asp Phe Thr
85 90 95

Leu Lys Ile Ser Arg Val Glu Ala Glu Asp Leu Gly Val Tyr Tyr Cys
100 105 110

Phe Gln Gly Ser Tyr Val Pro Trp Thr Phe Gly Gly Gly Thr Lys Leu
115 120 125

Glu Ile Lys Arg Ala Asp Ala Ala Pro Thr Val Ser Ile Phe Pro Pro
130 135 140

Ser Ser Glu Gln Leu Thr Ser Gly Gly Ala Ser Val Val Cys Phe Leu
145 150 155 160

Asn Asn Phe Tyr Pro Arg Asp Ile Asn Val Lys Trp Lys Ile Asp Gly
165 170 175

Ser Glu Arg Gln Asn Gly Val Leu Asn Ser Trp Thr Asp Gln Asp Ser
180 185 190

Lys Asp Ser Thr Tyr Ser Met Ser Ser Thr Leu Thr Leu Thr Lys Asp
195 200 205

Glu Tyr Glu Arg His Asn Ser Tyr Thr Cys Glu Ala Thr His Lys Thr
210 215 220

Ser Thr Ser Pro Ile Val Lys Ser Phe Asn Arg Asn Glu Cys
225 230 235

<210> SEQ ID NO 11
<211> LENGTH: 444
<212> TYPE: PRT
<213> ORGANISM: mus musculus

<400> SEQUENCE: 11

Gln Val Gln Leu Gln Gln Pro Gly Ala Glu Leu Val Arg Pro Gly Thr
1 5 10 15

-continued

```
Ser Val Lys Leu Ser Cys Lys Ala Ser Gly Tyr Thr Phe Thr Ser His
            20                  25                  30

Trp Leu His Trp Val Lys Gln Arg Pro Gly Gln Gly Leu Glu Trp Ile
        35                  40                  45

Gly Val Leu Asp Pro Ser Asp Phe Tyr Ser Asn Tyr Asn Gln Asn Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Leu Leu Ser Gly Asp Tyr Ala Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430
```

His Thr Glu Lys Ser Leu Ser His Ser Pro Gly Lys
435 440

<210> SEQ ID NO 12
<211> LENGTH: 219
<212> TYPE: PRT
<213> ORGANISM: mus musculus

<400> SEQUENCE: 12

Asp Val Leu Met Thr Gln Ile Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Ser Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser Tyr Val Pro Trp Thr Phe Gly Gly Gly Thr Lys Leu Glu Ile Lys
100 105 110

Arg Ala Asp Ala Ala Pro Thr Val Ser Ile Phe Pro Pro Ser Ser Glu
115 120 125

Gln Leu Thr Ser Gly Gly Ala Ser Val Val Cys Phe Leu Asn Asn Phe
130 135 140

Tyr Pro Arg Asp Ile Asn Val Lys Trp Lys Ile Asp Gly Ser Glu Arg
145 150 155 160

Gln Asn Gly Val Leu Asn Ser Trp Thr Asp Gln Asp Ser Lys Asp Ser
165 170 175

Thr Tyr Ser Met Ser Ser Thr Leu Thr Leu Thr Lys Asp Glu Tyr Glu
180 185 190

Arg His Asn Ser Tyr Thr Cys Glu Ala Thr His Lys Thr Ser Thr Ser
195 200 205

Pro Ile Val Lys Ser Phe Asn Arg Asn Glu Cys
210 215

<210> SEQ ID NO 13
<211> LENGTH: 10
<212> TYPE: PRT
<213> ORGANISM: mus musculus

<400> SEQUENCE: 13

Gln Val Gln Leu Gln Gln Pro Gly Ala Glu
1 5 10

<210> SEQ ID NO 14
<211> LENGTH: 10
<212> TYPE: PRT
<213> ORGANISM: mus musculus

<400> SEQUENCE: 14

Asp Val Leu Met Thr Gln Ile Pro Leu Ser
1 5 10

<210> SEQ ID NO 15
<211> LENGTH: 5
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 15

Asp Tyr Ala Met Ser
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ile Ser Asp Gly Gly Thr Tyr Thr Tyr Tyr Pro Asp Ser Val Lys
1               5                   10                  15

Gly

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Trp Gly Asp Tyr Asp Gly Phe Asp Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Ser Gln Glu Ile Ser Gly Tyr Leu Ser
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Ser Thr Leu Asp Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Leu Gln Tyr Asp Ser Tyr Pro Tyr Thr
1               5


<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Thr Ile Ser Asp Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115


<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Arg Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105


<210> SEQ ID NO 23
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 23

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Ala Met Ser Trp Ile Arg Gln Ala Pro Gly
    50                  55                  60

Lys Gly Leu Glu Trp Val Ser Thr Ile Ser Asp Gly Gly Thr Tyr Thr
65                  70                  75                  80

Tyr Tyr Pro Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Glu Trp Gly Asp Tyr Asp Gly Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Met His Glu Ala Leu His Asn His Tyr Thr Gln Lys Ser
450 455 460

Leu Ser Leu Ser Pro Gly Lys
465 470

<210> SEQ ID NO 24
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Met Asp Met Arg Val Pro Ala Gln Leu Leu Gly Leu Leu Leu Leu Trp
1 5 10 15

Leu Arg Gly Ala Arg Cys Asp Ile Gln Met Thr Gln Ser Pro Ser Ser
20 25 30

Leu Ser Ala Ser Val Gly Asp Arg Val Thr Ile Thr Cys Arg Ala Ser
35 40 45

Gln Glu Ile Ser Gly Tyr Leu Ser Trp Tyr Gln Gln Lys Pro Gly Lys
50 55 60

Ala Pro Lys Arg Leu Ile Tyr Ala Ala Ser Thr Leu Asp Ser Gly Val
65 70 75 80

Pro Ser Arg Phe Ser Gly Ser Gly Ser Gly Thr Glu Phe Thr Leu Thr
85 90 95

Ile Ser Ser Leu Gln Pro Glu Asp Phe Ala Thr Tyr Tyr Cys Leu Gln
100 105 110

Tyr Asp Ser Tyr Pro Tyr Thr Phe Gly Gln Gly Thr Lys Leu Glu Ile
115 120 125

Lys Arg Thr Val Ala Ala Pro Ser Val Phe Ile Phe Pro Pro Ser Asp
130 135 140

Glu Gln Leu Lys Ser Gly Thr Ala Ser Val Val Cys Leu Leu Asn Asn
145 150 155 160

Phe Tyr Pro Arg Glu Ala Lys Val Gln Trp Lys Val Asp Asn Ala Leu
165 170 175

Gln Ser Gly Asn Ser Gln Glu Ser Val Thr Glu Gln Asp Ser Lys Asp
180 185 190

Ser Thr Tyr Ser Leu Ser Ser Thr Leu Thr Leu Ser Lys Ala Asp Tyr
195 200 205

Glu Lys His Lys Val Tyr Ala Cys Glu Val Thr His Gln Gly Leu Ser
210 215 220

Ser Pro Val Thr Lys Ser Phe Asn Arg Gly Glu Cys
225 230 235

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Ser His Trp Leu His
1 5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Val Leu Asp Pro Ser Asp Phe Tyr Ser Asn Tyr Asn Gln Asn Phe Lys
1 5 10 15

Gly

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Gly Leu Leu Ser Gly Asp Tyr Ala Met Asp Tyr
1 5 10

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Arg Ser Ser Gln Ser Ile Val His Ser Asn Gly Asn Thr Tyr Leu Glu
1 5 10 15

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Lys Val Ser Asn Arg Phe Ser
1 5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Phe Gln Gly Ser Tyr Val Pro Trp Thr
1 5

<210> SEQ ID NO 31
<211> LENGTH: 120

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser His
            20                  25                  30

Trp Leu His Trp Val Lys Gln Arg Pro Gly Gln Gly Leu Glu Trp Ile
        35                  40                  45

Gly Val Leu Asp Pro Ser Asp Phe Tyr Ser Asn Tyr Asn Gln Asn Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Leu Leu Ser Gly Asp Tyr Ala Met Asp Tyr Trp Gly Gln
            100                 105                 110

Gly Thr Ser Val Thr Val Ser Ser
        115                 120
```

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Val Pro Trp Thr Phe Gly Gly Gly Thr Lys Leu Glu Ile Lys
            100                 105                 110
```

<210> SEQ ID NO 33
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Gly Trp Ser Cys Ile Ile Val Leu Leu Val Ser Thr Ala Thr Gly
1               5                   10                  15

Val His Ser Gln Val Gln Leu Gln Gln Pro Gly Ala Glu Leu Val Arg
```

-continued

```
            20                  25                  30

Pro Gly Thr Ser Val Lys Leu Ser Cys Lys Ala Ser Gly Tyr Thr Phe
        35                  40                  45

Thr Ser His Trp Leu His Trp Val Lys Gln Arg Pro Gly Gln Gly Leu
    50                  55                  60

Glu Trp Ile Gly Val Leu Asp Pro Ser Asp Phe Tyr Ser Asn Tyr Asn
65                  70                  75                  80

Gln Asn Phe Lys Gly Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Leu Leu Ser Gly Asp Tyr Ala Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Pro Ser Ser Thr Trp Pro Ser Gln Thr Val Thr Cys Asn Val Ala
    210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
            260                 265                 270

Pro Lys Val Thr Cys Val Val Val Asp Ile Ser Lys Asp Asp Pro Glu
        275                 280                 285

Val Gln Phe Ser Trp Phe Val Asp Asp Val Glu Val His Thr Ala Gln
    290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
        355                 360                 365

Pro Pro Lys Glu Gln Met Ala Lys Asp Lys Val Ser Leu Thr Cys Met
    370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                405                 410                 415

Asp Gly Ser Tyr Phe Val Tyr Ser Lys Leu Asn Val Gln Lys Ser Asn
            420                 425                 430

Trp Glu Ala Gly Asn Thr Phe Thr Cys Ser Val Leu His Glu Gly Leu
        435                 440                 445
```

-continued

```
His Asn His His Thr Glu Lys Ser Leu Ser His Ser Pro Gly Lys
    450                 455                 460


<210> SEQ ID NO 34
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Lys Leu Pro Val Arg Leu Leu Val Leu Met Phe Trp Ile Pro Ala
1               5                   10                  15

Ser Ser Ser Asp Val Leu Met Thr Gln Ile Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Ser Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235


<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Phe Gly Leu Ser Val Gly
1               5


<210> SEQ ID NO 36
<211> LENGTH: 16
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 36

His Ile Trp Trp Asp Asp Asp Lys Tyr Tyr Asn Pro Ala Leu Lys Ser
1 5 10 15

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Ile Gly Ala Asp Ala Leu Pro Phe Asp Tyr
1 5 10

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Arg Ser Ser Lys Ser Leu Leu His Ser Asn Gly Asn Thr Tyr Leu Tyr
1 5 10 15

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Arg Met Ser Asn Leu Ala Ser
1 5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Met Gln His Leu Glu Tyr Pro Phe Thr
1 5

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Gln Val Thr Leu Lys Glu Ser Gly Pro Gly Ile Leu Arg Pro Ser Gln
1 5 10 15

```
Thr Leu Ser Leu Thr Cys Ser Phe Ser Gly Phe Ser Leu Ser Thr Phe
            20                  25                  30

Gly Leu Ser Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Ile Gly Ala Asp Ala Leu Pro Phe Asp Tyr Trp Gly Gln
            100                 105                 110

Gly Thr Thr Leu Thr Val Ser Ser
        115                 120


<210> SEQ ID NO 42
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Leu Thr Gln Thr Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110


<210> SEQ ID NO 43
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Arg
            20                  25                  30

Pro Ser Gln Thr Leu Ser Leu Thr Cys Ser Phe Ser Gly Phe Ser Leu
        35                  40                  45

Ser Thr Phe Gly Leu Ser Val Gly Trp Ile Arg Gln Pro Ser Gly Lys
    50                  55                  60

Gly Leu Glu Trp Leu Ala His Ile Trp Trp Asp Asp Asp Lys Tyr Tyr
65                  70                  75                  80
```

```
Asn Pro Ala Leu Lys Ser Arg Leu Thr Ile Ser Lys Asp Thr Ser Lys
                85                  90                  95

Asn Gln Val Phe Leu Lys Ile Ala Asn Val Asp Thr Ala Asp Thr Ala
            100                 105                 110

Thr Tyr Tyr Cys Ala Arg Ile Gly Ala Asp Ala Leu Pro Phe Asp Tyr
        115                 120                 125

Trp Gly Gln Gly Thr Thr Leu Thr Val Ser Ser Ala Lys Thr Thr Pro
    130                 135                 140

Pro Ser Val Tyr Pro Leu Ala Pro Gly Cys Gly Asp Thr Thr Gly Ser
145                 150                 155                 160

Ser Val Thr Ser Gly Cys Leu Val Lys Gly Tyr Phe Pro Glu Pro Val
                165                 170                 175

Thr Val Thr Trp Asn Ser Gly Ser Leu Ser Ser Ser Val His Thr Phe
            180                 185                 190

Pro Ala Leu Leu Gln Ser Gly Leu Tyr Thr Met Ser Ser Ser Val Thr
        195                 200                 205

Val Pro Ser Ser Thr Trp Pro Ser Gln Thr Val Thr Cys Ser Val Ala
    210                 215                 220

His Pro Ala Ser Ser Thr Thr Val Asp Lys Lys Leu Glu Pro Ser Gly
225                 230                 235                 240

Pro Ile Ser Thr Ile Asn Pro Cys Pro Pro Cys Lys Glu Cys His Lys
                245                 250                 255

Cys Pro Ala Pro Asn Leu Glu Gly Gly Pro Ser Val Phe Ile Phe Pro
            260                 265                 270

Pro Asn Ile Lys Asp Val Leu Met Ile Ser Leu Thr Pro Lys Val Thr
        275                 280                 285

Cys Val Val Val Asp Val Ser Glu Asp Asp Pro Asp Val Gln Ile Ser
    290                 295                 300

Trp Phe Val Asn Asn Val Glu Val His Thr Ala Gln Thr Gln Thr His
305                 310                 315                 320

Arg Glu Asp Tyr Asn Ser Thr Ile Arg Val Val Ser Thr Leu Pro Ile
                325                 330                 335

Gln His Gln Asp Trp Met Ser Gly Lys Glu Phe Lys Cys Lys Val Asn
            340                 345                 350

Asn Lys Asp Leu Pro Ser Pro Ile Glu Arg Thr Ile Ser Lys Ile Lys
        355                 360                 365

Gly Leu Val Arg Ala Pro Gln Val Tyr Thr Leu Pro Pro Pro Ala Glu
    370                 375                 380

Gln Leu Ser Arg Lys Asp Val Ser Leu Thr Cys Leu Val Val Gly Phe
385                 390                 395                 400

Asn Pro Gly Asp Ile Ser Val Glu Trp Thr Ser Asn Gly His Thr Glu
                405                 410                 415

Glu Asn Tyr Lys Asp Thr Ala Pro Val Leu Asp Ser Asp Gly Ser Tyr
            420                 425                 430

Phe Ile Tyr Ser Lys Leu Asn Met Lys Thr Ser Lys Trp Glu Lys Thr
        435                 440                 445

Asp Ser Phe Ser Cys Asn Val Arg His Glu Gly Leu Lys Asn Tyr Tyr
    450                 455                 460

Leu Lys Lys Thr Ile Ser Arg Ser Pro Gly Lys
465                 470                 475
```

<210> SEQ ID NO 44
<211> LENGTH: 239
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 44

Met Arg Cys Leu Ala Glu Phe Leu Gly Leu Leu Val Leu Trp Ile Pro
1 5 10 15

Gly Ala Ile Gly Asp Ile Val Leu Thr Gln Thr Ala Pro Ser Val Pro
20 25 30

Val Thr Pro Gly Glu Ser Val Ser Ile Ser Cys Arg Ser Ser Lys Ser
35 40 45

Leu Leu His Ser Asn Gly Asn Thr Tyr Leu Tyr Trp Phe Leu Gln Arg
50 55 60

Pro Gly Gln Ser Pro Gln Leu Leu Ile Tyr Arg Met Ser Asn Leu Ala
65 70 75 80

Ser Gly Val Pro Asp Arg Phe Ser Gly Ser Gly Ser Gly Thr Ala Phe
85 90 95

Thr Leu Arg Ile Ser Arg Val Glu Ala Glu Asp Val Gly Val Tyr Tyr
100 105 110

Cys Met Gln His Leu Glu Tyr Pro Phe Thr Phe Gly Ser Gly Thr Lys
115 120 125

Leu Glu Ile Lys Arg Ala Asp Ala Ala Pro Thr Val Ser Ile Phe Pro
130 135 140

Pro Ser Ser Glu Gln Leu Thr Ser Gly Gly Ala Ser Val Val Cys Phe
145 150 155 160

Leu Asn Asn Phe Tyr Pro Arg Asp Ile Asn Val Lys Trp Lys Ile Asp
165 170 175

Gly Ser Glu Arg Gln Asn Gly Val Leu Asn Ser Trp Thr Asp Gln Asp
180 185 190

Ser Lys Asp Ser Thr Tyr Ser Met Ser Ser Thr Leu Thr Leu Thr Lys
195 200 205

Asp Glu Tyr Glu Arg His Asn Ser Tyr Thr Cys Glu Ala Thr His Lys
210 215 220

Thr Ser Thr Ser Pro Ile Val Lys Ser Phe Asn Arg Asn Glu Cys
225 230 235

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Asp His Ile Ile His
1 5

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Tyr Ile Tyr Pro Arg Asp Gly Tyr Ile Lys Tyr Asn Glu Lys Phe Lys
1 5 10 15

Gly

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Gly Tyr Tyr Tyr Ala Met Asp Tyr
1 5

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Arg Ser Ser Gln Ser Ile Val His Ser Ile Gly Asn Thr Tyr Leu Glu
1 5 10 15

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Phe Gln Gly Ser His Val Pro Phe Thr
1 5

<210> SEQ ID NO 50
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

Gln Val Gln Leu Gln Gln Ser Asp Ala Glu Leu Val Lys Pro Gly Ala
1 5 10 15

Ser Val Lys Ile Ser Cys Lys Val Ser Gly Tyr Thr Phe Thr Asp His
20 25 30

Ile Ile His Trp Met Lys Gln Arg Pro Glu Gln Gly Leu Glu Trp Ile
35 40 45

Gly Tyr Ile Tyr Pro Arg Asp Gly Tyr Ile Lys Tyr Asn Glu Lys Phe
50 55 60

Lys Gly Lys Ala Thr Leu Thr Ala Asp Lys Ser Ser Ser Thr Ala Tyr
65 70 75 80

Met Gln Val Asn Ser Leu Thr Ser Glu Asp Ser Ala Val Tyr Phe Cys
85 90 95

Ala Arg Gly Tyr Tyr Tyr Ala Met Asp Tyr Trp Gly Gln Gly Thr Ser
100 105 110

Val Thr Val Ser Ser
115

<210> SEQ ID NO 51
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Ile Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```

<210> SEQ ID NO 52
<211> LENGTH: 460
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

```
Met Glu Trp Ser Trp Val Ser Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Val Ser Gly Tyr Thr Phe
        35                  40                  45

Thr Asp His Ile Ile His Trp Met Lys Gln Arg Pro Glu Gln Gly Leu
    50                  55                  60

Glu Trp Ile Gly Tyr Ile Tyr Pro Arg Asp Gly Tyr Ile Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Val Asn Ser Leu Thr Ser Glu Asp Ser Ala Val
            100                 105                 110

Tyr Phe Cys Ala Arg Gly Tyr Tyr Tyr Ala Met Asp Tyr Trp Gly Gln
        115                 120                 125

Gly Thr Ser Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190
```

Leu Gln Ser Asp Leu Tyr Thr Leu Ser Ser Ser Val Thr Val Pro Ser
195 200 205

Ser Thr Trp Pro Ser Gln Thr Val Thr Cys Asn Val Ala His Pro Ala
210 215 220

Ser Ser Thr Lys Val Asp Lys Lys Ile Val Pro Arg Asp Cys Gly Cys
225 230 235 240

Lys Pro Cys Ile Cys Thr Val Pro Glu Val Ser Ser Val Phe Ile Phe
245 250 255

Pro Pro Lys Pro Lys Asp Val Leu Thr Ile Thr Leu Thr Pro Lys Val
260 265 270

Thr Cys Val Val Val Asp Ile Ser Lys Asp Asp Pro Glu Val Gln Phe
275 280 285

Ser Trp Phe Val Asp Asp Val Glu Val His Thr Ala Gln Thr Gln Pro
290 295 300

Arg Glu Glu Gln Phe Asn Ser Thr Phe Arg Ser Val Ser Glu Leu Pro
305 310 315 320

Ile Met His Gln Asp Trp Leu Asn Gly Lys Glu Phe Lys Cys Arg Val
325 330 335

Asn Ser Ala Ala Phe Pro Ala Pro Ile Glu Lys Thr Ile Ser Lys Thr
340 345 350

Lys Gly Arg Pro Lys Ala Pro Gln Val Tyr Thr Ile Pro Pro Pro Lys
355 360 365

Glu Gln Met Ala Lys Asp Lys Val Ser Leu Thr Cys Met Ile Thr Asp
370 375 380

Phe Phe Pro Glu Asp Ile Thr Val Glu Trp Gln Trp Asn Gly Gln Pro
385 390 395 400

Ala Glu Asn Tyr Lys Asn Thr Gln Pro Ile Met Asp Thr Asp Gly Ser
405 410 415

Tyr Phe Val Tyr Ser Lys Leu Asn Val Gln Lys Ser Asn Trp Glu Ala
420 425 430

Gly Asn Thr Phe Thr Cys Ser Val Leu His Glu Gly Leu His Asn His
435 440 445

His Thr Glu Lys Ser Leu Ser His Ser Pro Gly Lys
450 455 460

<210> SEQ ID NO 53
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Met Lys Leu Pro Val Arg Leu Leu Val Leu Met Phe Trp Ile Pro Ala
1 5 10 15

Ser Arg Ser Asp Val Leu Met Thr Gln Thr Pro Leu Ser Leu Pro Val
20 25 30

Ser Leu Gly Asp Gln Ala Ser Ile Ser Cys Arg Ser Ser Gln Ser Ile
35 40 45

Val His Ser Ile Gly Asn Thr Tyr Leu Glu Trp Tyr Leu Gln Lys Pro
50 55 60

Gly Gln Ser Pro Lys Leu Leu Ile Tyr Lys Val Ser Asn Arg Phe Ser
65 70 75 80

Gly Val Pro Glu Arg Phe Ser Gly Ser Gly Ser Gly Thr Asp Phe Thr

```
                85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235


<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Tyr Trp Met His
1               5


<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Met Ile Asp Pro Ser Asp Val Tyr Thr Asn Tyr Asn Pro Lys Phe Lys
1               5                   10                  15

Gly


<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Tyr Ser Gly Asp Tyr
1               5


<210> SEQ ID NO 57
<211> LENGTH: 115
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 57

```
Gln Val Gln Leu Leu Gln Pro Gly Ala Glu Leu Val Arg Pro Gly Thr
1               5                   10                  15

Ser Val Lys Leu Ser Cys Lys Thr Ser Gly Tyr Thr Phe Ser Ser Tyr
            20                  25                  30

Trp Met His Trp Val Lys Gln Arg Pro Gly Gln Gly Leu Glu Trp Ile
        35                  40                  45

Gly Met Ile Asp Pro Ser Asp Val Tyr Thr Asn Tyr Asn Pro Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Ser Gly Asp Tyr Trp Gly Gln Gly Thr Thr Leu Thr
            100                 105                 110

Val Ser Ser
        115
```

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 58

```
Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Val Pro Trp Thr Phe Gly Gly Gly Thr Lys Leu Glu Ile Lys
            100                 105                 110
```

<210> SEQ ID NO 59
<211> LENGTH: 458
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 59

```
Met Gly Trp Ser Cys Ile Ile Val Leu Leu Val Ser Thr Ala Thr Cys
1               5                   10                  15

Val His Ser Gln Val Gln Leu Leu Gln Pro Gly Ala Glu Leu Val Arg
            20                  25                  30

Pro Gly Thr Ser Val Lys Leu Ser Cys Lys Thr Ser Gly Tyr Thr Phe
```

-continued

```
        35                  40                  45

Ser Ser Tyr Trp Met His Trp Val Lys Gln Arg Pro Gly Gln Gly Leu
    50                  55                  60

Glu Trp Ile Gly Met Ile Asp Pro Ser Asp Val Tyr Thr Asn Tyr Asn
65                  70                  75                  80

Pro Lys Phe Lys Gly Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Asn Tyr Ser Gly Asp Tyr Trp Gly Gln Gly Thr
        115                 120                 125

Thr Leu Thr Val Ser Ser Ala Lys Thr Thr Pro Pro Ser Val Tyr Pro
    130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Pro Ser Ser Thr
        195                 200                 205

Trp Pro Ser Gln Thr Val Thr Cys Asn Val Ala His Pro Ala Ser Ser
    210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
                245                 250                 255

Lys Pro Lys Asp Val Leu Thr Ile Thr Leu Thr Pro Lys Val Thr Cys
            260                 265                 270

Val Val Val Asp Ile Ser Lys Asp Asp Pro Glu Val Gln Phe Ser Trp
        275                 280                 285

Phe Val Asp Asp Val Glu Val His Thr Ala Gln Thr Gln Pro Arg Glu
    290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
                325                 330                 335

Ala Ala Phe Pro Ala Pro Ile Glu Lys Thr Ile Ser Lys Thr Lys Gly
            340                 345                 350

Arg Pro Lys Ala Pro Gln Val Tyr Thr Ile Pro Pro Pro Lys Glu Gln
        355                 360                 365

Met Ala Lys Asp Lys Val Ser Leu Thr Cys Met Ile Thr Asp Phe Phe
    370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asp Thr Asp Gly Ser Tyr Phe
                405                 410                 415

Val Tyr Ser Lys Leu Asn Val Gln Lys Ser Asn Trp Glu Ala Gly Asn
            420                 425                 430

Thr Phe Thr Cys Ser Val Leu His Glu Gly Leu His Asn His His Thr
        435                 440                 445

Glu Lys Ser Leu Ser His Ser Pro Gly Lys
    450                 455
```

<210> SEQ ID NO 60
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

```
Met Lys Leu Pro Val Arg Leu Leu Val Leu Met Phe Trp Ile Pro Ala
1               5                   10                  15

Ser Ser Ser Asp Val Leu Met Thr Gln Ile Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

```
Thr Tyr Gly Met Ser
1               5
```

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Trp Ile Asn Thr Tyr Ser Gly Val Pro Thr Tyr Ala Asp Asp Phe Lys
1 5 10 15

Gly

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Gly Arg Asp Gly Tyr Gln Val Ala Trp Phe Ala Tyr
1 5 10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Ile Thr Ser Thr Asp Ile Asp Asp Asp Met Asn
1 5 10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Glu Gly Asn Thr Leu Arg Pro
1 5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Leu Gln Ser Asp Asn Leu Pro Tyr Thr
1 5

<210> SEQ ID NO 67
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 67

Gln Ile Gln Leu Val Gln Ser Gly Pro Glu Leu Lys Lys Pro Gly Glu
1 5 10 15

Ala Val Lys Ile Ser Cys Lys Ser Ser Gly Tyr Thr Phe Thr Thr Tyr

```
            20                  25                  30

Gly Met Ser Trp Val Lys Gln Ala Pro Gly Arg Ala Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Ser Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Arg Asp Gly Tyr Gln Val Ala Trp Phe Ala Tyr Trp Gly
            100                 105                 110

Gln Gly Thr Leu Val Thr Val Ser Ala
        115                 120


<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Thr Thr Val Thr Gln Ser Pro Ala Ser Leu Ser Met Ala Ile Gly
1               5                   10                  15

Asp Lys Val Thr Ile Arg Cys Ile Thr Ser Thr Asp Ile Asp Asp Asp
            20                  25                  30

Met Asn Trp Phe Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Gly
    50                  55                  60

Ser Gly Tyr Gly Thr Asp Phe Ile Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105


<210> SEQ ID NO 69
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Ala Val Lys Ile Ser Cys Lys Ser Ser Gly Tyr Thr Phe
        35                  40                  45

Thr Thr Tyr Gly Met Ser Trp Val Lys Gln Ala Pro Gly Arg Ala Leu
    50                  55                  60

Lys Trp Met Gly Trp Ile Asn Thr Tyr Ser Gly Val Pro Thr Tyr Ala
65                  70                  75                  80

Asp Asp Phe Lys Gly Arg Phe Ala Phe Ser Leu Glu Ser Ser Ala Ser
```

```
                85                  90                  95

Thr Ala Tyr Leu Gln Ile Asn Asn Leu Lys Asn Glu Asp Thr Ala Thr
            100                 105                 110

Tyr Phe Cys Ala Arg Gly Arg Asp Gly Tyr Gln Val Ala Trp Phe Ala
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Gln Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460
```

```
<210> SEQ ID NO 70
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 70

Met Phe Ser Leu Ala Leu Leu Leu Ser Leu Leu Leu Leu Cys Val Ser
1 5 10 15

Asp Ser Arg Ala Glu Thr Thr Val Thr Gln Ser Pro Ala Ser Leu Ser
20 25 30

Met Ala Ile Gly Asp Lys Val Thr Ile Arg Cys Ile Thr Ser Thr Asp
35 40 45

Ile Asp Asp Asp Met Asn Trp Phe Gln Gln Lys Pro Gly Glu Pro Pro
50 55 60

Lys Leu Leu Ile Ser Glu Gly Asn Thr Leu Arg Pro Gly Val Pro Ser
65 70 75 80

Arg Phe Ser Gly Ser Gly Tyr Gly Thr Asp Phe Ile Phe Thr Ile Glu
85 90 95

Asn Met Leu Ser Glu Asp Val Ala Asp Tyr Tyr Cys Leu Gln Ser Asp
100 105 110

Asn Leu Pro Tyr Thr Phe Gly Gly Gly Thr Lys Leu Glu Ile Lys Arg
115 120 125

Ala Asp Ala Ala Pro Thr Val Ser Ile Phe Pro Pro Ser Ser Glu Gln
130 135 140

Leu Thr Ser Gly Gly Ala Ser Val Val Cys Phe Leu Asn Asn Phe Tyr
145 150 155 160

Pro Arg Asp Ile Asn Val Lys Trp Lys Ile Asp Gly Ser Glu Arg Gln
165 170 175

Asn Gly Val Leu Asn Ser Trp Thr Asp Gln Asp Ser Lys Asp Ser Thr
180 185 190

Tyr Ser Met Ser Ser Thr Leu Thr Leu Thr Lys Asp Glu Tyr Glu Arg
195 200 205

His Asn Ser Tyr Thr Cys Glu Ala Thr His Lys Thr Ser Thr Ser Pro
210 215 220

Ile Val Lys Ser Phe Asn Arg Asn Glu Cys
225 230

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Asn Tyr Trp Met His
1 5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Met Ile Asp Pro Ser Asp Ser Tyr Thr Asn Tyr Asn Pro Lys Phe Lys
1 5 10 15

Gly

<210> SEQ ID NO 73
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 73

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Met Ile Asp Pro Ser Asp Ser Tyr Thr Asn Tyr Asn Pro Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Ser Gly Asp Tyr Trp Gly Gln Gly Thr Thr Leu Thr
            100                 105                 110

Val Ser Ser
        115
```

<210> SEQ ID NO 74
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Val Pro Trp Thr Phe Gly Gly Gly Thr Lys Leu Glu Ile Lys
            100                 105                 110
```

<210> SEQ ID NO 75
<211> LENGTH: 458
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 75

```
Met Gly Trp Ser Cys Ile Ile Val Leu Leu Val Ser Thr Ala Thr Gly
1               5                   10                  15
```

-continued

```
Val His Ser Gln Val Gln Leu Gln Gln Pro Gly Ala Glu Leu Val Arg
            20                  25                  30

Pro Gly Thr Ser Val Lys Leu Ser Cys Lys Ala Ser Gly Tyr Thr Phe
        35                  40                  45

Thr Asn Tyr Trp Met His Trp Val Lys Gln Arg Pro Gly Gln Gly Leu
    50                  55                  60

Glu Trp Ile Gly Met Ile Asp Pro Ser Asp Ser Tyr Thr Asn Tyr Asn
65                  70                  75                  80

Pro Lys Phe Lys Gly Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Asn Tyr Ser Gly Asp Tyr Trp Gly Gln Gly Thr
        115                 120                 125

Thr Leu Thr Val Ser Ser Ala Lys Thr Thr Pro Pro Ser Val Tyr Pro
    130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Pro Ser Ser Thr
        195                 200                 205

Trp Pro Ser Gln Thr Val Thr Cys Asn Val Ala His Pro Ala Ser Ser
    210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
                245                 250                 255

Lys Pro Lys Asp Val Leu Thr Ile Thr Leu Thr Pro Lys Val Thr Cys
            260                 265                 270

Val Val Val Asp Ile Ser Lys Asp Asp Pro Glu Val Gln Phe Ser Trp
        275                 280                 285

Phe Val Asp Asp Val Glu Val His Thr Ala Gln Thr Gln Pro Arg Glu
    290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
                325                 330                 335

Ala Ala Phe Pro Ala Pro Ile Glu Lys Thr Ile Ser Lys Thr Lys Gly
            340                 345                 350

Arg Pro Lys Ala Pro Gln Val Tyr Thr Ile Pro Pro Pro Lys Glu Gln
        355                 360                 365

Met Ala Lys Asp Lys Val Ser Leu Thr Cys Met Ile Thr Asp Phe Phe
    370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asp Thr Asp Gly Ser Tyr Phe
                405                 410                 415

Val Tyr Ser Lys Leu Asn Val Gln Lys Ser Asn Trp Glu Ala Gly Asn
            420                 425                 430
```

```
Thr Phe Thr Cys Ser Val Leu His Glu Gly Leu His Asn His His Thr
        435                 440                 445

Glu Lys Ser Leu Ser His Ser Pro Gly Lys
    450                 455


<210> SEQ ID NO 76
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235


<210> SEQ ID NO 77
<211> LENGTH: 449
<212> TYPE: PRT
<213> ORGANISM: Artificial Sequence
<220> FEATURE:
<223> OTHER INFORMATION: Antibody heavy chain

<400> SEQUENCE: 77

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
```

-continued

```
        35                  40                  45

Ser Thr Ile Ser Asp Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 78
<211> LENGTH: 214
<212> TYPE: PRT
<213> ORGANISM: Artificial Sequence
<220> FEATURE:
<223> OTHER INFORMATION: Antibody light chain

<400> SEQUENCE: 78

Asp Ile Gln Met Thr Gln Ser Pro Ser Ser Leu Ser Ala Ser Val Gly
1 5 10 15

Asp Arg Val Thr Ile Thr Cys Arg Ala Ser Gln Glu Ile Ser Gly Tyr
20 25 30

Leu Ser Trp Tyr Gln Gln Lys Pro Gly Lys Ala Pro Lys Arg Leu Ile
35 40 45

Tyr Ala Ala Ser Thr Leu Asp Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln Tyr Asp Ser Tyr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 79
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 79

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Met Ser Trp Val Arg Gln Ala Pro Gly Lys Gly Leu Glu Trp Val
35 40 45

Ala Thr Ile Ser Asp Gly Gly Thr Tyr Thr Tyr Tyr Pro Asp Asn Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys

```
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115


<210> SEQ ID NO 80
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Thr Ile Ser Asp Gly Gly Thr Tyr Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115


<210> SEQ ID NO 81
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Thr Ile Ser Asp Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115
```

<210> SEQ ID NO 82
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ser Asp Gly Gly Thr Tyr Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115
```

<210> SEQ ID NO 83
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 83

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Ser Asp Gly Gly Thr Tyr Thr Tyr Tyr Pro Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115
```

<210> SEQ ID NO 84
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 84

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Thr Ile Ser Asp Gly Gly Thr Tyr Thr Tyr Tyr Pro Asp Asn Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115


<210> SEQ ID NO 85
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Thr Ile Ser Asp Gly Gly Thr Tyr Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115


<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Leu Leu Ile
        35                  40                  45
```

```
Tyr Ala Ala Ser Thr Leu Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105


<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Phe Gln Gln Lys Pro Gly Lys Ala Pro Lys Ser Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105


<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Arg Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105


<210> SEQ ID NO 89
```

<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 89

Asp Ile Gln Met Thr Gln Ser Pro Ser Ser Leu Ser Ala Ser Val Gly
1 5 10 15

Asp Arg Val Thr Ile Thr Cys Arg Ala Ser Gln Glu Ile Ser Gly Tyr
20 25 30

Leu Ser Trp Tyr Gln Gln Lys Pro Gly Lys Ala Pro Lys Leu Leu Ile
35 40 45

Tyr Ala Ala Ser Thr Leu Asp Ser Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Leu Gln Tyr Asp Ser Tyr Pro Tyr
85 90 95

Thr Phe Gly Gln Gly Thr Lys Leu Glu Ile Lys
100 105

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 90

Asp Ile Gln Met Thr Gln Ser Pro Ser Ser Leu Ser Ala Ser Val Gly
1 5 10 15

Asp Arg Val Thr Ile Thr Cys Arg Ala Ser Gln Glu Ile Ser Gly Tyr
20 25 30

Leu Ser Trp Tyr Gln Gln Lys Pro Gly Lys Ala Pro Lys Leu Leu Ile
35 40 45

Tyr Ala Ala Ser Thr Leu Asp Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Ser Tyr Pro Tyr
85 90 95

Thr Phe Gly Gln Gly Thr Lys Leu Glu Ile Lys
100 105

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 91

Asp Ile Gln Met Thr Gln Ser Pro Ser Ser Leu Ser Ala Ser Val Gly
1 5 10 15

Asp Arg Val Thr Ile Thr Cys Arg Ala Ser Gln Glu Ile Ser Gly Tyr
20 25 30

-continued

```
Leu Ser Trp Leu Gln Gln Lys Pro Gly Gly Ala Ile Lys Arg Leu Ile
        35                  40                  45

Tyr Ala Ala Ser Thr Leu Asp Ser Gly Val Pro Ser Arg Phe Ser Gly
    50                  55                  60

Ser Gly Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105


<210> SEQ ID NO 92
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Asn Phe Gly Leu Ser Leu Met Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Ala Met Ser Trp Val Arg Gln Thr Pro Glu Lys Arg Leu
    50                  55                  60

Glu Trp Val Ala Thr Ile Ser Asp Gly Gly Thr Tyr Thr Tyr Tyr Pro
65                  70                  75                  80

Asp Asn Val Lys Gly Arg Phe Thr Ile Ser Arg Asp Asn Ala Lys Asn
                85                  90                  95

Asn Leu Tyr Leu Gln Met Ser His Leu Lys Ser Glu Asp Thr Ala Met
            100                 105                 110

Tyr Tyr Cys Ala Arg Glu Trp Gly Asp Tyr Asp Gly Phe Asp Tyr Trp
        115                 120                 125

Gly Gln Gly Thr Thr Leu Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285
```

His Glu Asp Pro Glu Val Lys Phe Asn Trp Tyr Val Asp Gly Val Glu
290 295 300

Val His Asn Ala Lys Thr Lys Pro Arg Glu Glu Gln Tyr Asn Ser Thr
305 310 315 320

Tyr Arg Val Val Ser Val Leu Thr Val Leu His Gln Asp Trp Leu Asn
325 330 335

Gly Lys Glu Tyr Lys Cys Lys Val Ser Asn Lys Ala Leu Pro Ala Pro
340 345 350

Ile Glu Lys Thr Ile Ser Lys Ala Lys Gly Gln Pro Arg Glu Pro Gln
355 360 365

Val Tyr Thr Leu Pro Pro Ser Arg Glu Glu Met Thr Lys Asn Gln Val
370 375 380

Ser Leu Thr Cys Leu Val Lys Gly Phe Tyr Pro Ser Asp Ile Ala Val
385 390 395 400

Glu Trp Glu Ser Asn Gly Gln Pro Glu Asn Asn Tyr Lys Thr Thr Pro
405 410 415

Pro Val Leu Asp Ser Asp Gly Ser Phe Phe Leu Tyr Ser Lys Leu Thr
420 425 430

Val Asp Lys Ser Arg Trp Gln Gln Gly Asn Val Phe Ser Cys Ser Val
435 440 445

Met His Glu Ala Leu His Asn His Tyr Thr Gln Lys Ser Leu Ser Leu
450 455 460

Ser Pro Gly Lys
465

<210> SEQ ID NO 93
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Met Asp Met Arg Val Pro Ala His Val Phe Gly Phe Leu Leu Leu Trp
1 5 10 15

Phe Pro Gly Thr Arg Cys Asp Ile Gln Met Thr Gln Ser Pro Ser Ser
20 25 30

Leu Ser Ala Ser Leu Gly Glu Arg Val Ser Leu Thr Cys Arg Ala Ser
35 40 45

Gln Glu Ile Ser Gly Tyr Leu Ser Trp Leu Gln Gln Lys Pro Asp Gly
50 55 60

Thr Ile Lys Arg Leu Ile Tyr Ala Ala Ser Thr Leu Asp Ser Gly Val
65 70 75 80

Pro Lys Arg Phe Ser Gly Ser Arg Ser Gly Ser Asp Tyr Ser Leu Thr
85 90 95

Ile Gly Ser Leu Glu Ser Glu Asp Leu Ala Asp Tyr Tyr Cys Leu Gln
100 105 110

Tyr Asp Ser Tyr Pro Tyr Thr Phe Gly Gly Gly Thr Lys Leu Glu Ile
115 120 125

Lys Arg Thr Val Ala Ala Pro Ser Val Phe Ile Phe Pro Pro Ser Asp
130 135 140

Glu Gln Leu Lys Ser Gly Thr Ala Ser Val Val Cys Leu Leu Asn Asn
145 150 155 160

Phe Tyr Pro Arg Glu Ala Lys Val Gln Trp Lys Val Asp Asn Ala Leu

```
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 94
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Ala Met Ser Trp Ile Arg Gln Ala Pro Gly
    50                  55                  60

Lys Gly Leu Glu Trp Val Ser Thr Ile Ser Asp Gly Gly Thr Tyr Thr
65                  70                  75                  80

Tyr Tyr Pro Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Glu Trp Gly Asp Tyr Asp Gly Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285
```

-continued

```
Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 95
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Ala Met Ser Trp Ile Arg Gln Ala Pro Gly
    50                  55                  60

Lys Gly Leu Glu Trp Val Ser Thr Ile Ser Asp Gly Gly Thr Tyr Thr
65                  70                  75                  80

Tyr Tyr Pro Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Glu Trp Gly Asp Tyr Asp Gly Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175
```

```
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 96
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Phe Gln Gln Lys Pro Gly Lys
```

```
    50                  55                  60

Ala Pro Lys Ser Leu Ile Tyr Ala Ala Ser Thr Leu Asp Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Leu Gln
            100                 105                 110

Tyr Asp Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 97
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Tyr Gln Gln Lys Pro Gly Lys
    50                  55                  60

Ala Pro Lys Arg Leu Ile Tyr Ala Ala Ser Thr Leu Asp Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

Tyr Asp Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

-continued

```
Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 98
<211> LENGTH: 449
<212> TYPE: PRT
<213> ORGANISM: Artificial Sequence
<220> FEATURE:
<223> OTHER INFORMATION: Antibody heavy chain no leader sequence

<400> SEQUENCE: 98

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Thr Ile Ser Asp Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

-continued

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 99
<211> LENGTH: 445
<212> TYPE: PRT
<213> ORGANISM: Artificial Sequence
<220> FEATURE:
<223> OTHER INFORMATION: Antibody heavy chain no leader sequence

<400> SEQUENCE: 99

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Thr Ile Ser Asp Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
```

```
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 100
<211> LENGTH: 214
<212> TYPE: PRT
<213> ORGANISM: Artificial Sequence
<220> FEATURE:
<223> OTHER INFORMATION: Antibody light chain no leader sequence

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Phe Gln Gln Lys Pro Gly Lys Ala Pro Lys Ser Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 101
<211> LENGTH: 214
<212> TYPE: PRT
<213> ORGANISM: Artificial Sequence
<220> FEATURE:
<223> OTHER INFORMATION: Antibody light chain no leader sequence

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Arg Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 102
<211> LENGTH: 450
<212> TYPE: PRT
<213> ORGANISM: Artificial Sequence
<220> FEATURE:
<223> OTHER INFORMATION: Antibody heavy chain

<400> SEQUENCE: 102
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
            420                 425                 430

Glu Ala Leu His Asn His Tyr Thr Gln Lys Ser Leu Ser Leu Ser Pro
        435                 440                 445

Gly Lys
    450


<210> SEQ ID NO 103
<211> LENGTH: 214
<212> TYPE: PRT
<213> ORGANISM: Artificial Sequence
<220> FEATURE:
<223> OTHER INFORMATION: Antibody light chain

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 104
<211> LENGTH: 448
<212> TYPE: PRT
<213> ORGANISM: Artificial Sequence
<220> FEATURE:
<223> OTHER INFORMATION: Antibody heavy chain

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45
```

```
Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 105
<211> LENGTH: 214
<212> TYPE: PRT

<213> ORGANISM: Artificial Sequence
<220> FEATURE:
<223> OTHER INFORMATION: Antibody light chain

<400> SEQUENCE: 105

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Ile Gly
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Tyr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 106
<211> LENGTH: 447
<212> TYPE: PRT
<213> ORGANISM: Artificial Sequence
<220> FEATURE:
<223> OTHER INFORMATION: Antibody heavy chain

<400> SEQUENCE: 106

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Glu Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Asp Lys Trp Thr Trp Tyr Phe Asp Leu Trp Gly Arg Gly Thr Leu
100 105 110

```
Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 107
<211> LENGTH: 220
<212> TYPE: PRT
<213> ORGANISM: Artificial Sequence
<220> FEATURE:
<223> OTHER INFORMATION: Antibody light chain

<400> SEQUENCE: 107

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30
```

```
Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 108
<211> LENGTH: 445
<212> TYPE: PRT
<213> ORGANISM: Artificial Sequence
<220> FEATURE:
<223> OTHER INFORMATION: Antibody heavy chain

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 109
<211> LENGTH: 217
<212> TYPE: PRT
<213> ORGANISM: Artificial Sequence
<220> FEATURE:
<223> OTHER INFORMATION: Antibody light chain

<400> SEQUENCE: 109

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Val Val Ser Trp Tyr Gln Gln His Pro Gly Lys Ala Pro Lys Leu
        35                  40                  45

Ile Ile Tyr Glu Val Ser Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Cys Ser Tyr Ala Gly Ser
                85                  90                  95
```

-continued

```
Ser Ile Phe Val Ile Phe Gly Gly Gly Thr Lys Val Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215


<210> SEQ ID NO 110
<211> LENGTH: 449
<212> TYPE: PRT
<213> ORGANISM: Artificial Sequence
<220> FEATURE:
<223> OTHER INFORMATION: Antibody heavy chain

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45

Gly Trp Ile Tyr Ala Gly Thr Gly Ser Pro Ser Tyr Asn Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Arg Asp Tyr Tyr Ser Asn Ser Leu Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

-continued

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 111
<211> LENGTH: 220
<212> TYPE: PRT
<213> ORGANISM: Artificial Sequence
<220> FEATURE:
<223> OTHER INFORMATION: Antibody light chain

<400> SEQUENCE: 111

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
```

```
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 112
<211> LENGTH: 446
<212> TYPE: PRT
<213> ORGANISM: Artificial Sequence
<220> FEATURE:
<223> OTHER INFORMATION: Antibody heavy chain

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
```

-continued

```
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 113
<211> LENGTH: 214
<212> TYPE: PRT
<213> ORGANISM: Artificial Sequence
<220> FEATURE:
<223> OTHER INFORMATION: Antibody light chain

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

210

<210> SEQ ID NO 114
<211> LENGTH: 25
<212> TYPE: DNA
<213> ORGANISM: Artificial Sequence
<220> FEATURE:
<223> OTHER INFORMATION: Morpholino

<400> SEQUENCE: 114
cgtcacaggc aggacccact gccca 25

<210> SEQ ID NO 115
<211> LENGTH: 1342
<212> TYPE: PRT
<213> ORGANISM: Homo sapiens

<400> SEQUENCE: 115

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300
```

-continued

Cys Pro Pro Asp Lys Met Glu Val Asp Lys Asn Gly Leu Lys Met Cys
305 310 315 320

Glu Pro Cys Gly Gly Leu Cys Pro Lys Ala Cys Glu Gly Thr Gly Ser
325 330 335

Gly Ser Arg Phe Gln Thr Val Asp Ser Ser Asn Ile Asp Gly Phe Val
340 345 350

Asn Cys Thr Lys Ile Leu Gly Asn Leu Asp Phe Leu Ile Thr Gly Leu
355 360 365

Asn Gly Asp Pro Trp His Lys Ile Pro Ala Leu Asp Pro Glu Lys Leu
370 375 380

Asn Val Phe Arg Thr Val Arg Glu Ile Thr Gly Tyr Leu Asn Ile Gln
385 390 395 400

Ser Trp Pro Pro His Met His Asn Phe Ser Val Phe Ser Asn Leu Thr
405 410 415

Thr Ile Gly Gly Arg Ser Leu Tyr Asn Arg Gly Phe Ser Leu Leu Ile
420 425 430

Met Lys Asn Leu Asn Val Thr Ser Leu Gly Phe Arg Ser Leu Lys Glu
435 440 445

Ile Ser Ala Gly Arg Ile Tyr Ile Ser Ala Asn Arg Gln Leu Cys Tyr
450 455 460

His His Ser Leu Asn Trp Thr Lys Val Leu Arg Gly Pro Thr Glu Glu
465 470 475 480

Arg Leu Asp Ile Lys His Asn Arg Pro Arg Arg Asp Cys Val Ala Glu
485 490 495

Gly Lys Val Cys Asp Pro Leu Cys Ser Ser Gly Gly Cys Trp Gly Pro
500 505 510

Gly Pro Gly Gln Cys Leu Ser Cys Arg Asn Tyr Ser Arg Gly Gly Val
515 520 525

Cys Val Thr His Cys Asn Phe Leu Asn Gly Glu Pro Arg Glu Phe Ala
530 535 540

His Glu Ala Glu Cys Phe Ser Cys His Pro Glu Cys Gln Pro Met Glu
545 550 555 560

Gly Thr Ala Thr Cys Asn Gly Ser Gly Ser Asp Thr Cys Ala Gln Cys
565 570 575

Ala His Phe Arg Asp Gly Pro His Cys Val Ser Ser Cys Pro His Gly
580 585 590

Val Leu Gly Ala Lys Gly Pro Ile Tyr Lys Tyr Pro Asp Val Gln Asn
595 600 605

Glu Cys Arg Pro Cys His Glu Asn Cys Thr Gln Gly Cys Lys Gly Pro
610 615 620

Glu Leu Gln Asp Cys Leu Gly Gln Thr Leu Val Leu Ile Gly Lys Thr
625 630 635 640

His Leu Thr Met Ala Leu Thr Val Ile Ala Gly Leu Val Val Ile Phe
645 650 655

Met Met Leu Gly Gly Thr Phe Leu Tyr Trp Arg Gly Arg Arg Ile Gln
660 665 670

Asn Lys Arg Ala Met Arg Arg Tyr Leu Glu Arg Gly Glu Ser Ile Glu
675 680 685

Pro Leu Asp Pro Ser Glu Lys Ala Asn Lys Val Leu Ala Arg Ile Phe
690 695 700

Lys Glu Thr Glu Leu Arg Lys Leu Lys Val Leu Gly Ser Gly Val Phe
705 710 715 720

Gly Thr Val His Lys Gly Val Trp Ile Pro Glu Gly Glu Ser Ile Lys

-continued

```
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu  Glu Glu Val Glu Leu  Glu Pro Glu
        995                 1000                1005

Leu Asp  Leu Asp Leu Asp Leu  Glu Ala Glu Glu Asp  Asn Leu Ala
    1010                 1015                 1020

Thr Thr  Thr Leu Gly Ser Ala  Leu Ser Leu Pro Val  Gly Thr Leu
    1025                 1030                 1035

Asn Arg  Pro Arg Gly Ser Gln  Ser Leu Leu Ser Pro  Ser Ser Gly
    1040                 1045                 1050

Tyr Met  Pro Met Asn Gln Gly  Asn Leu Gly Glu Ser  Cys Gln Glu
    1055                 1060                 1065

Ser Ala  Val Ser Gly Ser Ser  Glu Arg Cys Pro Arg  Pro Val Ser
    1070                 1075                 1080

Leu His  Pro Met Pro Arg Gly  Cys Leu Ala Ser Glu  Ser Ser Glu
    1085                 1090                 1095

Gly His  Val Thr Gly Ser Glu  Ala Glu Leu Gln Glu  Lys Val Ser
    1100                 1105                 1110

Met Cys  Arg Ser Arg Ser Arg  Ser Arg Ser Pro Arg  Pro Arg Gly
    1115                 1120                 1125

Asp Ser  Ala Tyr His Ser Gln  Arg His Ser Leu Leu  Thr Pro Val
    1130                 1135                 1140
```

Thr Pro Leu Ser Pro Pro Gly Leu Glu Glu Glu Asp Val Asn Gly
1145 1150 1155

Tyr Val Met Pro Asp Thr His Leu Lys Gly Thr Pro Ser Ser Arg
1160 1165 1170

Glu Gly Thr Leu Ser Ser Val Gly Leu Ser Ser Val Leu Gly Thr
1175 1180 1185

Glu Glu Glu Asp Glu Asp Glu Glu Tyr Glu Tyr Met Asn Arg Arg
1190 1195 1200

Arg Arg His Ser Pro Pro His Pro Pro Arg Pro Ser Ser Leu Glu
1205 1210 1215

Glu Leu Gly Tyr Glu Tyr Met Asp Val Gly Ser Asp Leu Ser Ala
1220 1225 1230

Ser Leu Gly Ser Thr Gln Ser Cys Pro Leu His Pro Val Pro Ile
1235 1240 1245

Met Pro Thr Ala Gly Thr Thr Pro Asp Glu Asp Tyr Glu Tyr Met
1250 1255 1260

Asn Arg Gln Arg Asp Gly Gly Gly Pro Gly Gly Asp Tyr Ala Ala
1265 1270 1275

Met Gly Ala Cys Pro Ala Ser Glu Gln Gly Tyr Glu Glu Met Arg
1280 1285 1290

Ala Phe Gln Gly Pro Gly His Gln Ala Pro His Val His Tyr Ala
1295 1300 1305

Arg Leu Lys Thr Leu Arg Ser Leu Glu Ala Thr Asp Ser Ala Phe
1310 1315 1320

Asp Asn Pro Asp Tyr Trp His Ser Arg Leu Phe Pro Lys Ala Asn
1325 1330 1335

Ala Gln Arg Thr
1340

<210> SEQ ID NO 116
<211> LENGTH: 345
<212> TYPE: PRT
<213> ORGANISM: Artificial Sequence
<220> FEATURE:
<223> OTHER INFORMATION: Fusion protein

<400> SEQUENCE: 116

Glu Glu Glu Leu Gln Val Ile Gln Pro Asp Lys Ser Val Ser Val Ala
1 5 10 15

Ala Gly Glu Ser Ala Ile Leu His Cys Thr Val Thr Ser Leu Ile Pro
20 25 30

Val Gly Pro Ile Gln Trp Phe Arg Gly Ala Gly Pro Ala Arg Glu Leu
35 40 45

Ile Tyr Asn Gln Lys Glu Gly His Phe Pro Arg Val Thr Thr Val Ser
50 55 60

Glu Ser Thr Lys Arg Glu Asn Met Asp Phe Ser Ile Ser Ile Ser Asn
65 70 75 80

Ile Thr Pro Ala Asp Ala Gly Thr Tyr Tyr Cys Val Lys Phe Arg Lys
85 90 95

Gly Ser Pro Asp Thr Glu Phe Lys Ser Gly Ala Gly Thr Glu Leu Ser
100 105 110

Val Arg Ala Lys Pro Ser Asp Lys Thr His Thr Cys Pro Pro Cys Pro
115 120 125

Ala Pro Glu Leu Leu Gly Gly Pro Ser Val Phe Leu Phe Pro Pro Lys
130 135 140

```
Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345
```

<210> SEQ ID NO 117
<211> LENGTH: 345
<212> TYPE: PRT
<213> ORGANISM: Artificial Sequence
<220> FEATURE:
<223> OTHER INFORMATION: Fusion protein

<400> SEQUENCE: 117

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160
```

Val Val Asp Val Ser His Glu Asp Pro Glu Val Lys Phe Asn Trp Tyr
165 170 175

Val Asp Gly Val Glu Val His Asn Ala Lys Thr Lys Pro Arg Glu Glu
180 185 190

Gln Tyr Asn Ser Thr Tyr Arg Val Val Ser Val Leu Thr Val Leu His
195 200 205

Gln Asp Trp Leu Asn Gly Lys Glu Tyr Lys Cys Lys Val Ser Asn Lys
210 215 220

Ala Leu Pro Ala Pro Ile Glu Lys Thr Ile Ser Lys Ala Lys Gly Gln
225 230 235 240

Pro Arg Glu Pro Gln Val Tyr Thr Leu Pro Pro Ser Arg Asp Glu Leu
245 250 255

Thr Lys Asn Gln Val Ser Leu Thr Cys Leu Val Lys Gly Phe Tyr Pro
260 265 270

Ser Asp Ile Ala Val Glu Trp Glu Ser Asn Gly Gln Pro Glu Asn Asn
275 280 285

Tyr Lys Thr Thr Pro Pro Val Leu Asp Ser Asp Gly Ser Phe Phe Leu
290 295 300

Tyr Ser Lys Leu Thr Val Asp Lys Ser Arg Trp Gln Gln Gly Asn Val
305 310 315 320

Phe Ser Cys Ser Val Met His Glu Ala Leu His Asn His Tyr Thr Gln
325 330 335

Lys Ser Leu Ser Leu Ser Pro Gly Lys
340 345

<210> SEQ ID NO 118
<211> LENGTH: 347
<212> TYPE: PRT
<213> ORGANISM: Artificial Sequence
<220> FEATURE:
<223> OTHER INFORMATION: Fusion protein

<400> SEQUENCE: 118

Glu Glu Glu Leu Gln Val Ile Gln Pro Asp Lys Ser Val Ser Val Ala
1 5 10 15

Ala Gly Glu Ser Ala Ile Leu His Cys Thr Val Thr Ser Leu Ile Pro
20 25 30

Val Gly Pro Ile Gln Trp Phe Arg Gly Ala Gly Pro Ala Arg Glu Leu
35 40 45

Ile Tyr Asn Gln Lys Glu Gly His Phe Pro Arg Val Thr Thr Val Ser
50 55 60

Glu Ser Thr Lys Arg Glu Asn Met Asp Phe Ser Ile Ser Ile Ser Asn
65 70 75 80

Ile Thr Pro Ala Asp Ala Gly Thr Tyr Tyr Cys Val Lys Phe Arg Lys
85 90 95

Gly Ser Pro Asp Thr Glu Phe Lys Ser Gly Ala Gly Thr Glu Leu Ser
100 105 110

Val Arg Ala Lys Pro Ser Glu Ser Lys Tyr Gly Pro Pro Cys Pro Pro
115 120 125

Cys Pro Ala Pro Glu Phe Leu Gly Gly Pro Ser Val Phe Leu Phe Pro
130 135 140

Pro Lys Pro Lys Asp Thr Leu Met Ile Ser Arg Thr Pro Glu Val Thr
145 150 155 160

Cys Val Val Val Asp Val Ser Gln Glu Asp Pro Glu Val Gln Phe Asn
165 170 175

-continued

```
Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345
```

HER3 RADIOIMMUNOTHERAPY FOR THE TREATMENT OF SOLID CANCERS

CROSS-REFERENCE TO RELATED APPLICATIONS

This application
- is a continuation-in-part of International Application No. PCT/US21/56259 filed Oct. 22, 2021, which claims priority to each of U.S. provisional application Ser. Nos. 63,250,725 filed Sep. 30, 2021, 63/226,699 filed Jul. 28, 2021, and 63/104,386 filed Oct. 22, 2020;
- claims the benefit of U.S. provisional patent application no. 63/118,181 filed Nov. 25, 2020; and
- claims the benefit of U.S. provisional patent application no. 63/116,225 filed Nov. 20, 2020,
- each of the foregoing applications hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 22, 2021, is named ATNM-010PCT_SL_ST25. txt and is 191,107 bytes in size.

FIELD OF THE INVENTION

The present invention relates to the field of radiotherapeutics.

BACKGROUND OF THE INVENTION

ErbB3/HER3 is a type I transmembrane glycoprotein that is a member of the erythroblastic oncogene B (ErbB) family of tyrosine kinase receptors (EGFR, HER2, HER3, and HER4). Signaling through HER3 can be activated in a ligand-dependent or ligand-independent manner. In the absence of ligand, HER3 receptor molecules are normally expressed at the cell surface as monomers with a conformation that prevents receptor dimerization. In this conformation, the dimerization loop of subdomain II makes intramolecular contact with a pocket on subdomain IV. Binding of a HER3 ligand such as a neuregulin (NRG), e.g. NRG1 (also known as heregulin, HRG) or NRG2, to subdomains I and III of the extracellular region causes a conformational change that results in exposure of the dimerization loop of subdomain II, facilitating receptor dimerization and signaling. Certain cancer-associated mutations in HER3 disrupt this interaction between subdomains II and IV, i.e., the interaction required for formation of the inactive 'closed' conformation, and thereby cause constitutive presentation of the dimerization loop and activation of HER3-mediated signaling in the absence of ligand binding.

Antibodies that target HER3 may be employed to target specific cancer cells, particularly certain solid cancers. HER3 is overexpressed in several types of cancers such as breast, gastrointestinal, and pancreatic cancers. A correlation between the expression of HER2/HER3 and the progression from a non-invasive stage to an invasive stage of these cancers has been shown. Agents that interfere with HER3-mediated signaling, such as anti-HER3 antibodies, may enable the establishment of a robust immune response to the cancer cells that would be otherwise inadequate using conventional therapy.

Accordingly, one object of the presently disclosed invention is to provide therapeutically effective radiolabeled HER3 targeting agents, such as for the treatment of HER3-positive cancers. A related object of the presently disclosed invention is to provide therapeutic methods including administration of such a radiolabeled HER3 targeting agent, either alone or in combination with one or more additional therapeutic agents.

SUMMARY OF THE INVENTION

The present invention provides a HER3 targeting agent, such as a monoclonal antibody, peptide, or small molecule that targets HER3, labeled with a radioisotope, and methods of diagnosing and/or treating HER3-positive (HER3-expressing) cancers using the radiolabeled HER3 targeting agent.

According to certain aspects of the present invention, the radiolabeled HER3 targeting agent useful for diagnostics purposes may be an anti-HER3 antibody, peptide, or small molecule including a radioisotope, such as $^{111}$In, $^{68}$Ga, $^{64}$Cu, $^{89}$Zr, or $^{177}$Lu.

According to certain other aspects, the radiolabeled HER3 targeting agent useful for therapeutic interventions may be an anti-HER3 antibody, peptide, or small molecule including a radioisotope, such as: $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb, or combinations thereof. According to certain preferred aspects, the radiolabeled HER3 targeting agent may include $^{131}$I, $^{90}$Y, $^{177}$Lu, $^{225}$Ac, $^{213}$Bi, $^{211}$At, $^{227}$Th, or $^{212}$Pb.

According to certain aspects, the HER3-positive cancer may be a solid tumor.

Therapeutic methods of the presently disclosed invention generally include administering to a patient a therapeutically effective amount of the radiolabeled HER3 targeting agent. According to certain aspects, the effective amount of the radiolabeled HER3 targeting agent may be a maximum tolerated dose (MTD) or may be a fractioned dose wherein the total amount of radiation administered in the fractioned doses is the MTD.

According to certain aspects, provided and/or used is a composition or quantity of the HER3 targeting agent that includes a radiolabeled fraction and a non-radiolabeled fraction of the HER3 targeting agent. As such, an effective amount of the HER3 targeting agent may include a total protein dose of less than 100 mg, such as from 5 mg to 60 mg, or 5 mg to 45 mg. According to certain aspects, the total protein dose may be from 0.001 mg/kg to 3 mg/kg body weight of the subject, such as from 0.005 mg/kg to 2 mg/kg body weight of the subject. According to certain aspects, the total protein dose may be less than 2 mg/kg, or less than 1 mg/kg, less than 0.5 mg/kg, or even less than 0.1 mg/kg. A portion of the total protein dose is radiolabeled (i.e., radioconjugate) as indicated, wherein the effective amount of the radiolabeled HER3 targeting agent may depend on the specific radioisotope selected. Preferred radioisotopes for therapeutic interventions include $^{225}$Ac, $^{177}$Lu, $^{131}$I, $^{90}$Y, $^{213}$Bi, $^{211}$At, $^{227}$Th, or $^{212}$Pb. Thus, the HER3 targeting agent may include a radiolabeled fraction and an unlabeled fraction.

According to certain aspects, an effective amount of a HER3 targeting agent in terms of radiation dose, i.e., of the radiolabeled portion thereof, such as an $^{225}$Ac-anti-HER3 antibody, peptide, or small molecule, may include a dose of 0.1 to 20 μCi/kg body weight of the subject, such as 0.1 to 10 μCi/kg or 0.1 to 5 uCi/kg body weight of the subject, or 0.5 to 20 μCi/kg or 1 to 10 uCi/kg body weight of the subject.

According to certain aspects, the effective amount of the HER3 targeting agent, i.e., the radiolabeled portion thereof, such as an $^{225}$Ac-anti-HER3 antibody, peptide, or small molecule may depend on the configuration of the targeting agent, i.e., full length antibody or antigen-binding antibody fragment (e.g., Fab, $Fab_2$, minibody, nanobody, etc) such as any of those disclosed herein. For example, when the HER3 targeting agent includes an $^{225}$Ac-anti-HER3 antibody that is a full-length antibody, the dose may be below 5 uCi/kg body weight of the subject, such as 0.1 to 5 uCi/kg body weight of the subject. Alternatively, when the HER3 targeting agent includes an $^{225}$Ac-anti-HER3 antibody that is a fragment, the dose may be greater than 5 uCi/kg body weight of the subject, such as 5 to 20 uCi/kg body weight of the subject.

According to certain aspects, the HER3 targeting agent is an anti-HER3 antibody, such as a monoclonal antibody or an antigen binding fragment thereof, such as an IgG or an antigen binding fragment thereof, such as one that binds to an epitope of HER3 recognized by Patritumab from Daiichi Sankyo, Seribantumab (MM-121) from Merrimack Pharmaceuticals, Lumretuzumab from Roche, Elgemtumab from Novartis, GSK2849330 from GlaxoSmithKline, CDX-3379 of Celldex Therapeutics, EV20 and MP-RM-1 from MediPharma, ISU104 from Isu Abxis Co., HMBD-001 (10D1F) from Hummingbird Bioscience Pte., REGN1400 from Regeneron Pharmaceuticals, and/or AV-203 from AVEO Oncology. According to certain aspects, the anti-HER3 antibody is selected from one or more of Patritumab, Seribantumab, Lumretuzumab, Elgemtumab, AV-203, CDX-3379, or GSK2849330.

According to certain aspects, the HER3 targeting agent may be administered according to a dosing schedule selected from the group consisting of one dose every 7, 10, 12, 14, 20, 24, 28, 35, and 42 days throughout a treatment period, wherein the treatment period includes at least two doses.

According to certain aspects, the HER3 targeting agent may be administered according to a dose schedule that includes 2 doses, such as on days 1 and 5, 6, 7, 8, 9, or 10 of a treatment period, or days 1 and 8 of a treatment period.

According to certain aspects, the HER3 targeting agent may be administered as a single bolus or infusion in a single subject specific dose.

According to certain aspects, the methods may further include administration of one or more further therapeutic agents, such as a chemotherapeutic agent, a small molecule drug, an anti-inflammatory agent, an immunosuppressive agent, an immunomodulatory agent, an antimyeloma agent, a cytokine, or a combination thereof. Exemplary chemotherapeutic agents include at least radiosensitizers that may synergize with the radiolabeled HER3 targeting agent, such as temozolomide, cisplatin, and/or fluorouracil.

According to certain aspects, the methods may further include administration of one or more immune checkpoint therapies. Exemplary immune checkpoint therapies include an antibody against CTLA-4, PD-1, TIM-3, VISTA, BTLA, LAG-3, TIGIT, CD28, OX40, GITR, CD137, CD40, CD4OL, CD27, HVEM, PD-L1, PD-L2, PD-L3, PD-L4, CD80, CD86, CD137-L, GITR-L, CD226, B7-H3, B7-H4, BTLA, TIGIT, GALS, KIR, 2B4, CD160, CGEN-15049, or any combination thereof. According to certain aspects, the immune checkpoint therapy may include an antibody against an immune checkpoint protein selected from the group consisting of an antibody against PD-1, PD-L1, PD-L2, CTLA-4, CD137, and a combination thereof.

According to certain aspects, the immune checkpoint therapy may be administered to a subject in an effective amount, such as a dose of 0.1 mg/kg to 50 mg/kg of the patient's body weight, such as 0.1-5 mg/kg, or 5-30 mg/kg.

According to certain aspects, the methods may further include administration of one or more DNA damage response inhibitors (DDRi). Exemplary DDRi agents one or more antibodies or small molecules targeting poly(ADP-ribose) polymerase (i.e., a poly(ADP-ribose) polymerase inhibitor or PARPi). The PARPi may, for example, include olaparib, niraparib, rucaparib, talazoparib, or any combination thereof. According to certain aspects, the PARPi may be provided in a subject effective amount including 0.1 mg/day-1200 mg/day, such as 0.100 mg/day-600 mg/day, or 0.25 mg/day-1 mg/day. Exemplary subject effective amounts include 0.1 mg, 0.25 mg, 0.5 mg, 0.75 mg, 1.0 mg, 100 mg, 200 mg, 300 mg, 400 mg, 500 mg, 600 mg, 700 mg, 750 mg, 800 mg, 900 mg, and 1000 mg, taken orally in one or two doses per day.

Another exemplary DDRi includes an inhibitor of Ataxia telangiectasia mutated (ATM), Ataxia talangiectasia mutated and Rad-3 related (ATR), or Wee1. Exemplary inhibitors of ATM include KU-55933, KU-59403, wortmannin, CP466722, and KU-60019. Exemplary inhibitors of ATR include at least Schisandrin B, NU6027, NVP-BEA235, VE-821, VE-822, AZ20, and AZD6738. Exemplary inhibitors of Wee1 include AZD-1775 (i.e., adavosertib).

According to certain aspects, the methods may further include administration of one or more CD47 blockades. The CD47 blockade may include a monoclonal antibody, SIRPα-Fc fusion protein or other molecule that prevents CD47 binding to SIRPα or otherwise blocks or downregulates the immunosuppressive activity of CD47, such as magrolimab, lemzoparlimab, AO-176, AK117, IMC-002, IBI-188, IBI-322, BI 766063, ZL-1201, AXL148, RRx-001, ES004, SRF231, SHR-1603, TJC4, TTI-621, or TTI-622. Exemplary effective doses for the CD47 blockade include 0.05 to 5 mg/kg patient weight. The CD47 blockade may also include agents that modulate the expression of CD47 and/or SIRPα, such as a nucleic acid approach, e.g., anti-sense, RNAi, or μRNA approaches. Exemplary CD47 blockades also include phosphorodiamidate morpholino oligomers (PMO) that block translation of CD47 such as MBT-001.

According to certain aspects, the methods may further include administration of a combination of further therapeutic agents. Exemplary combinations include at least one or more DDRi and/or one or more immune checkpoint therapies and/or one or more CD47 blockades and/or one or more chemotherapeutics and/or one or more small molecule anticancer drugs and/or one or more targeting agents directed against different cancer-associated antigens.

According to certain aspects, the radiolabeled HER3 targeting agent and the one or more further therapeutic agents may be administered simultaneously or sequentially. When more than one additional therapeutic agent is administered, the agents may be administered simultaneously or sequentially.

According to certain aspects of the present invention, the radiolabeled HER3 targeting agent may be a multi-specific targeting agent such as a multi-specific antibody or bispecific antibody, in which at least one part recognizes HER3. Thus, the methods may include administering to the subject an effective amount of a multi-specific antibody, wherein the multi-specific antibody includes: a first target recognition component which specifically binds to an epitope of HER3, and a second target recognition component which specifically binds to a different epitope of HER3 than the first target recognition component, or to an epitope of a different antigen such as a different cancer-associated antigen. According to certain aspects, the HER3 targeting agent is a multi-specific antibody against a first epitope of HER3 and at least a second epitope of HER3, or against HER3 and at least a second (different) antigen. Exemplary multi-specific antibodies that may be radiolabeled for diagnostic and/or therapeutic use according to the invention include bispecific antibodies against HER3/HER2 such as MM-111 from Merrimack Pharmaceuticals or MCLA-128 from Merus N.V.; or against IGF-1R/HER3 such as MM-141 (i.e., Istiratumab) from Merrimack Pharmaceuticals; or against EGFR/HER3 such as MEHD7945A (i.e., Duligotumab) from Roche or any of the cetuximab-based bispecific or multi-specific zybodies from Zyngenia Inc.

According to certain aspects, a composition is provided that includes a mixture of a HER3 targeting agent such as an antibody against HER3 and one or more further targeting agents, such as antibodies, targeting/against one or more different cancer associated antigens, wherein one or more of the HER3 targeting agent and the other targeting agent(s) may be radiolabeled or non-radiolabeled in any combination. An exemplary antibody composition including an antibody mixture includes at least Sym013 from Symphogen having six monoclonal antibodies against EGFR (HER1), HER2, and HER3. In one aspect, one or more of the antibodies of the Sym013 may be radiolabeled in any combination, such as at least a HER3 antibody and none or one or more of the antibodies against EGFR and HER2.

Additional features, advantages, and aspects of the invention may be set forth or apparent from consideration of the following detailed description, drawings if any, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

FIG. 1 provides the amino acid sequences of the N-terminal region, complementarity determining regions, and variable regions of the heavy and light chains of a HER3 monoclonal antibody that may be embodied in various aspects of the present invention.

FIG. 2 provides the amino acid sequences of the full-length heavy and light chains, with and without leader sequences, of a HER3 monoclonal antibody that may be embodied in various aspects of the present invention.

DETAILED DESCRIPTION OF THE INVENTION

Figure 3:
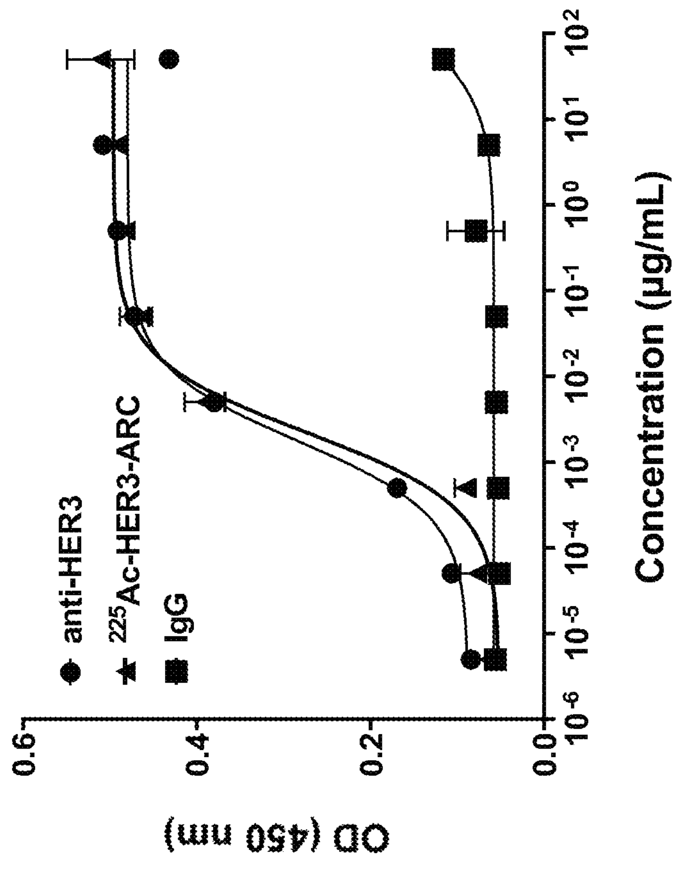
FIG. 3 shows ELISA assay binding characteristics of an Ac225 labeled DOTA-conjugated anti-HER3 monoclonal antibody versus the unmodified anti-HER3 antibody and a non-specific antibody (IgG), demonstrating that the modifications do not materially affect immune reactivity to HER3.

In one aspect, the presently disclosed invention provides compositions and methods for the treatment of cancers expressing HER3, i.e., HER3-positive cancers. This aspect generally includes administering to a mammalian subject in need of treatment, such as a human patient, an effective amount of a radiolabeled HER3 targeting agent, such as a radiolabeled antibody, peptide, or small molecule targeted to HER3, alone or in combination with one or more additional therapeutic agents and/or therapeutic modalities/treatments.

Additional therapeutic agents and modalities that may be used include, for example, at least one or more immune checkpoint therapy and/or one or more inhibitors of a component of the DNA damage response pathway (i.e., a DNA damage response inhibitor, DDRi, such as one or more agents against poly(ADP-ribose) polymerase, i.e., PARPi) and/or one or more CD47/SIRPα axis blockades and/or one or more chemotherapeutic agents such as radiosensitizers, and/or one or more small molecule oncology drugs such as tyrosine kinase inhibitors, and/or one or more targeting agents against different antigens.

The presently disclosed invention further provides methods for identifying, imaging and/or diagnosing HER3-positive cancers in a subject. The presently disclosed invention further provides methods for identifying, imaging and/or diagnosing HER3-positive cancer in a subject, followed by treating those subjects according to any of the methods disclosed herein.

Definitions and Abbreviations

The singular forms “a,” “an,” “the” and the like include plural referents unless the context clearly dictates otherwise.

Thus, for example, reference to "an" antibody includes both a single antibody and a plurality of different antibodies.

The words "comprising" and forms of the word "comprising" as well as the word "including" and forms of the word "including," as used in this description and in the claims, do not limit the inclusion of elements beyond what is referred to. Additionally, although throughout the present disclosure various aspects or elements thereof are described in terms of "including" or "comprising," corresponding aspects or elements thereof described in terms of "consisting essentially of" or "consisting of" are similarly disclosed. For example, while certain aspects of the invention have been described in terms of a method "including" or "comprising" administering a radiolabeled targeting agent, corresponding methods instead reciting "consisting essentially of" or "consisting of" administering the radiolabeled target are also within the scope of said aspects and disclosed by this disclosure.

The term "about" when used in this disclosure in connection with a numerical designation or value, e.g., in describing temperature, time, amount, and concentration, including in the description of a range, indicates a variance of ±10% and, within that larger variance, variances of ±5% or ±1% of the numerical designation or value.

As used herein, "administer", with respect to a targeting agent such as an antibody, antibody fragment, Fab fragment, or aptamer, means to deliver the agent to a subject's body via any known method suitable for antibody delivery. Specific modes of administration include, without limitation, intravenous, transdermal, subcutaneous, intraperitoneal, intrathecal and intra-tumoral administration. Exemplary administration methods for antibodies may be as substantially described in International Publication No. WO 2016/187514, incorporated by reference herein.

In addition, in this invention, antibodies may, for example, be formulated using one or more routinely used pharmaceutically acceptable carriers and excipients. Such carriers and excipients are well known to those skilled in the art. For example, injectable drug delivery systems include solutions, suspensions, gels, microspheres and polymeric injectables, and can include excipients such as solubility-altering agents (e.g., ethanol, propylene glycol and sucrose) and polymers (e.g., polycaprylactones and PLGA's).

As used herein, the term "antibody" includes, without limitation, (a) an immunoglobulin molecule including two heavy chains and two light chains and which recognizes an antigen; (b) polyclonal and monoclonal immunoglobulin molecules; (c) monovalent and divalent fragments thereof, such as Fab, di-Fab, scFvs, diabodies, minibodies, and nanobodies (sdAb); (d) naturally occurring and non-naturally occurring, such as wholly synthetic antibodies, IgG-Fc-silent, and chimeric; and (e) bi-specific and multi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. The N-terminus of each chain defines a "variable region" of about 100 to 110 or more amino acids primarily responsible for antigen recognition. The terms variable light chain (VL) and variable heavy chain (VH) refer to these regions of light and heavy chains respectively. Antibodies may be human, humanized or nonhuman. When a specific aspect of the presently disclosed invention refers to or recites an "antibody," it is envisioned as referring to any of the full-length antibodies or fragments thereof disclosed herein, unless explicitly denoted otherwise.

A "humanized" antibody refers to an antibody in which some, most or all amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

A "complementarity-determining region", or "CDR", refers to amino acid sequences that, together, define the binding affinity and specificity of the variable region of a native immunoglobulin binding site. There are three CDRs in each of the light and heavy chains of an antibody.

A "framework region", or "FR", refers to amino acid sequences interposed between CDRs, typically conserved, that act as the scaffold between the CDRs.

A "constant region" refers to the portion of an antibody molecule that is consistent for a class of antibodies and is defined by the type of light and heavy chains. For example, a light chain constant region can be of the kappa or lambda chain type and a heavy chain constant region can be of one of the five chain isotypes: alpha, delta, epsilon, gamma or mu. This constant region, in general, can confer effector functions exhibited by the antibodies. Heavy chains of various subclasses (such as the IgG subclass of heavy chains) are mainly responsible for different effector functions.

As used herein, a HER3 targeting agent may, for example, be an antibody as defined herein, e.g., full length antibody, minibody, or nanobody, that binds to any available epitope of HER3, such as human HER3, with a high immunoreactivity.

As used herein, "Immunoreactivity" refers to a measure of the ability of an immunoglobulin to recognize and bind to a specific antigen. "Specific binding" or "specifically binds" or "binds" refers to an antibody binding to an antigen or an epitope within the antigen with greater affinity than for other antigens, for example, within a relevant context such as within the body of a mammalian subject such as a human patient. An antibody, which may be embodied in or used in the various aspects of the invention, may for example bind to the antigen or the epitope within the antigen with an equilibrium dissociation constant ($K_D$) of about $1\times10^{-8}$ M or less, for example about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a nonspecific antigen (e.g., BSA, casein). The dissociation constant may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset).

An "epitope" refers to the target molecule site (e.g., at least a portion of an antigen) that is capable of being recognized by, and bound by, a targeting agent such as an antibody, antibody fragment, Fab fragment, or aptamer. For a protein antigen, for example, this may refer to the region of the protein (i.e., amino acids, and particularly their side chains) that is bound by the antibody. Overlapping epitopes include at least one to five common amino acid residues. Methods of identifying epitopes of antibodies are known to those skilled in the art and include, for example, those described in Antibodies, A Laboratory Manual, Cold Spring Harbor Laboratory, Ed Harlow and David Lane (1988).

Radiolabeled HER3 targeting agents as disclosed herein may be used to treat HER3-positive, i.e., HER3-expressing, cancers or precancerous conditions, such as solid tumors. By "HER3-positive" or "HER3-expressing" it is meant that at least some of the cancer cells within a patient, such as within a tumor, express or over-express HER3.

As used herein, the terms "proliferative disorder" and "cancer" may be used interchangeably and may include, without limitation, a solid cancer (e.g., a tumor) and pre-cancerous proliferative disorders. "Solid cancers" that may be treated by the various aspects of the invention and which may be HER3-positive include, without limitation, bone cancer, pancreatic cancer, skin cancer, cancer of the head or neck, cutaneous or intraocular malignant melanoma, uterine cancer, ovarian cancer, prostate cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, pediatric tumors, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally-induced cancers including those induced by asbestos. Such cancers may be metastatic or non-metastatic.

According to certain aspects, the solid cancer which may be treated by the various aspects of the invention and which may be HER3-positive, may be breast cancer such as tamoxifen-sensitive breast cancer, tamoxifen-resistant breast cancer, HER2-positive breast cancer, HER2-negative breast cancer, or triple negative breast cancer (TNBC), gastric cancer, bladder cancer, cervical cancer, endometrial cancer, skin cancer such as melanoma, stomach cancer, testicular cancer, esophageal cancer, bronchioloalveolar cancer, prostate cancer such as castration resistant prostate cancer (CRPC), colorectal cancer, ovarian cancer, cervical epidermoid cancer, liver cancer such as hepatocellular carcinoma (HCC) or cholangiocarcinoma, pancreatic cancer, lung cancer such as non-small cell lung carcinoma (NSCLC), renal cancer, head and neck cancer such as head and neck squamous cell cancer, a carcinoma, a sarcoma, or any combination thereof. Such cancers may be metastatic or non-metastatic.

According to certain aspects, the HER3 targeting agent may be labeled with a radioisotope/radionuclide. As used herein, a "radioisotope" or "radionuclide" can be an alpha-emitting isotope, a beta-emitting isotope, and/or a gamma-emitting isotope. Exemplary radionuclides that may be used to label HER3 targeting agents or other targeting agents include the following: $^{131}I$, $^{125}I$, $^{123}I$, $^{90}Y$, $^{177}Lu$, $^{186}Re$, $^{188}Re$, $^{89}Sr$, $^{153}Sm$, $^{32}P$, $^{225}Ac$, $^{213}Bi$, $^{213}Po$, $^{211}At$, $^{212}Bi$, $^{213}Bi$, $^{223}Ra$, $^{227}Th$, $^{149}Tb$, $^{137}Cs$, $^{212}Pb$, $^{103}Pd$, $^{134}Ce$, $^{43}Sc$, $^{44}Sc$, $^{47}Sc$, $^{55}Co$, $^{60}Cu$, $^{61}Cu$, $^{62}Cu$, $^{64}Cu$, $^{67}Cu$, $^{66}Ga$, $^{67}Ga$, $^{68}Ga$, $^{82}Rb$, $^{86}Y$, $^{87}Y$, $^{89}Zr$, $^{97}Ru$, $^{105}Rh$, $^{109}Pd$, $^{111}In$, $^{117m}Sn$, $^{149}Pm$, $^{149}Tb$, $^{153}Sm$, $^{177}Lu$, $^{199}Au$, $^{201}Tl$, and $^{203}Pb$. Methods for affixing a radioisotope to a protein such as an antibody or antibody fragment (i.e., "labeling" the protein with the radioisotope) are well known in the art. Specific compositions and methods for labeling are described, for example, in International Publication No. WO 2017/155937 and U.S. Provisional Patent Application Nos. 63/042,651 filed Dec. 9, 2019 and 63/119,093 filed Nov. 30, 2020 titled "Compositions and methods for preparation of site-specific radioconjugates," each of which is incorporated by reference herein. HER3 targeting agents and other targeting agents containing one or more cysteine residues, such as peptides, proteins, antibodies and protein antibody mimetics may, for example, be chemically conjugated to any of the chelator-bearing, such as DOTA-bearing, stable linkers disclosed in U.S. Pat. No. 11,000,604 titled "Reagent for site-selective bioconjugation of proteins or antibodies" for radionuclide labeling.

According to certain aspects, the HER3 targeting agent may be an antibody, peptide, or small molecule radiolabeled with $^{225}Ac$ ("$^{225}Ac$-labeled"), and the effective amount may, for example, be at or below 50.0 μCi/kg (i.e., where the amount of $^{225}Ac$ administered to the subject delivers a radiation dose of below 50.0 μCi per kilogram of subject's body weight). According to certain aspects, when the HER3 targeting agent is $^{225}Ac$-labeled, the effective amount is below 50 μCi/kg, 40 μCi/kg, 30 μCi/kg, 20 μCi/kg, 10 μCi/kg, 5 μCi/kg, 4 μCi/kg, 3 μCi/kg, 2 μCi/kg, 1 μCi/kg, or 0.5 μCi/kg. According to certain aspects, when the HER3 targeting agent is $^{225}Ac$-labeled, the effective amount is at least 0.05 μCi/kg, or 0.1 μCi/kg, 0.2 μCi/kg, 0.3 μCi/kg, 0.4 μCi/kg, 0.5 μCi/kg, 1 μCi/kg, 2 μCi/kg, 3 μCi/kg, 4 μCi/kg, 5 μCi/kg, 6 μCi/kg, 7 μCi/kg, 8 μCi/kg, 9 μCi/kg, 10 μCi/kg, 12 μCi/kg, 14 μCi/kg, 15 μCi/kg, 16 μCi/kg, 18 μCi/kg, 20 μCi/kg, 30 μCi/kg, or 40 μCi/kg. According to certain aspects, the $^{225}Ac$-labeled antibody may be administered at a dose that includes any combination of upper and lower limits as described herein, such as from at least 0.1 μCi/kg to at or below 5 μCi/kg, or from at least 5 μCi/kg to at or below 20 μCi/kg.

According to certain aspects, the HER3 targeting agent may be an antibody, peptide, or small molecule that is $^{225}Ac$-labeled, and the effective amount may be at or below 2 mCi (i.e., wherein the $^{225}Ac$ is administered to the subject in a non-weight-based dosage). According to certain aspects, the effective dose of the $^{225}Ac$-labeled HER3 targeting agent may be below 1 mCi, such as 0.9 mCi, 0.8 mCi, 0.7 mCi, 0.6 mCi, 0.5 mCi, 0.4 mCi, 0.3 mCi, 0.2 mCi, 0.1 mCi, 90 μCi, 80 μCi, 70 μCi, 60 μCi, 50 μCi, 40 μCi, 30 μCi, 20 μCi, 10 μCi, or 5 μCi. The effective amount of $^{225}Ac$-labeled HER3 targeting agent may be at least 2 μCi, such as at least 5 μCi, 10 μCi, 20 μCi, 30 μCi, 40 μCi, 50 μCi, 60 μCi, 70 μCi, 80 μCi, 90 μCi, 100 μCi, 200 μCi, 300 μCi, 400 μCi, 500 μCi, 600 μCi, 700 μCi, 800 μCi, 900 μCi, 1 mCi, 1.1 mCi, 1.2 mCi, 1.3 mCi, 1.4 mCi, or 1.5 mCi. According to certain aspects, the $^{225}Ac$-labeled HER3 targeting agent may be administered at a dose that includes any combination of upper and lower limits as described herein, such as from at least 2 μCi to at or below 1 mCi, or from at least 2 μCi to at or below 250 μCi, or from 75 μCi to at or below 400 μCi.

According to certain aspects, the $^{225}Ac$-labeled HER3 targeting agent includes a single dose that delivers less than 12Gy, or less than 8 Gy, or less than 6 Gy, or less than 4 Gy, or less than 2 Gy, such as doses of 2 Gy to 8 Gy, to the subject, such as predominantly to the targeted solid tumor.

According to certain aspects, the HER3 targeting agent may be an antibody, peptide, or small molecule radiolabeled with $^{177}$Lu ("$^{177}$Lu-labeled"), and the effective amount may be, for example, below 1 mCi/kg (i.e., where the amount of $^{177}$Lu-labeled antibody administered to the subject delivers a radiation dose of below 1000 μCi per kilogram of subject's body weight). According to certain aspects, when the antibody is $^{177}$Lu-labeled, the effective amount is below 900 μCi/kg, 800 μCi/kg, 700 μCi/kg, 600 μCi/kg, 500 μCi/kg, 400 μCi/kg, 300 μCi/kg, 200 μCi/kg, 150 μCi/kg, 100 μCi/kg, 80 μCi/kg, 60 μCi/kg, 50 μCi/kg, 40 μCi/kg, 30 μCi/kg, 20 μCi/kg, 10 μCi/kg, 5 μCi/kg, or 1 μCi/kg. According to certain aspects, the effective amount of the $^{177}$Lu-labeled antibody is at least 1 μCi/kg, 2.5 μCi/kg, 5 μCi/kg, 10 μCi/kg, 20 μCi/kg, 30 μCi/kg, 40 μCi/kg, 50 μCi/kg, 60 μCi/kg, 70 μCi/kg, 80 μCi/kg, 90 μCi/kg, 100 μCi/kg, 150 μCi/kg, 200 μCi/kg, 250 μCi/kg, 300 μCi/kg, 350 μCi/kg, 400 μCi/kg or 450 μCi/kg. According to certain aspects, an $^{177}$Lu-labeled antibody may be administered at a dose that includes any combination of upper and lower limits as described herein, such as from at least 5 mCi/kg to at or below 50 μCi/kg, or from at least 50 mCi/kg to at or below 500 μCi/kg.

According to certain aspects, the HER3 targeting agent may be an antibody that is $^{177}$Lu-labeled, and the effective amount may be below 45 mCi, such as below 40 mCi, 30 mCi, 20 mCi, 10 mCi, 5 mCi, 3.0 mCi, 2.0 mCi, 1.0 mCi, 800 μCi, 600 μCi, 400 μCi, 200 μCi, 100 μCi, or 50 μCi. The effective amount of $^{177}$Lu-labeled HER3 targeting agent may be at least 10 μCi, such as at least 25 μCi, 50 μCi, 100 μCi, 200 μCi, 300 μCi, 400 μCi, 500 μCi, 600 μCi, 700 μCi, 800 μCi, 900 μCi, 1 mCi, 2 mCi, 3 mCi, 4 mCi, 5 mCi, 10 mCi, 15 mCi, 20 mCi, 25 mCi, 30 mCi. According to certain aspects, an $^{177}$Lu-labeled antibody may be administered at a dose that includes any combination of upper and lower limits as described herein, such as from at least 10 mCi to at or below 30 mCi, or from at least 100 μCi to at or below 3 mCi, or from 3 mCi to at or below 30 mCi.

According to certain aspects, the HER3 targeting agent may be an antibody, peptide, or small molecule radiolabeled with $^{131}$I ("$^{131}$I-labeled"), and the effective amount may be below, for example, 1200 mCi (i.e., where the amount of $^{131}$I administered to the subject delivers a total body radiation dose of below 1200 mCi in a non-weight-based dose). According to certain aspects, the effective amount of the $^{131}$I-labeled targeting agent may be below 1100 mCi, below 1000 mCi, below 900 mCi, below 800 mCi, below 700 mCi, below 600 mCi, below 500 mCi, below 400 mCi, below 300 mCi, below 200 mCi, below 150 mCi, or below 100 mCi. According to certain aspects, the effective amount of the $^{131}$I-labeled targeting agent may be below 200 mCi, such as below 190 mCi, 180 mCi, 170 mCi, 160 mCi, 150 mCi, 140 mCi, 130 mCi, 120 mCi, 110 mCi, 100 mCi, 90 mCi, 80 mCi, 70 mCi, 60 mCi, or 50 mCi. According to certain aspects, the effective amount of the $^{131}$I-labeled targeting agent may be at least 1 mCi, such as at least 2 mCi, 3 mCi, 4 mCi, 5 mCi, 6 mCi, 7 mCi, 8 mCi, 9 mCi, 10 mCi, 20 mCi, 30 mCi, 40 mCi, 50 mCi, 60 mCi, 70 mCi, 80 mCi, 90 mCi, 100 mCi, 110 mCi, 120 mCi, 130 mCi, 140 mCi, 150 mCi, 160 mCi, 170 mCi, 180 mCi, 190 mCi, 200 mCi, 250 mCi, 300 mCi, 350 mCi, 400 mCi, 450 mCi, 500 mCi. According to certain aspects, an $^{131}$I-labeled targeting agent may be administered at a dose that includes any combination of upper and lower limits as described herein, such as from at least 1 mCi to at or below 100 mCi, or at least 10 mCi to at or below 200 mCi.

While select radionuclides are discussed in detail herein, any, such as any disclosed herein, may be used for radiolabeled targeting agents, such as a radiolabeled HER3 targeting agent as disclosed herein.

As used herein, a composition including a HER3 targeting agent includes a "patient specific composition" that includes both a radionuclide labeled portion and an unlabeled portion. According to certain aspects of the present invention, when the HER3 targeting agent is labeled with a radioisotope, the majority of the targeting agent (antibody, antibody fragment, etc.) administered to a patient may consist of unlabeled targeting agent, with the minority being the radiolabeled targeting agent. The ratio of labeled to non-labeled targeting agent can be adjusted using known methods. According to certain aspects of the present invention, the patient specific composition may include the HER3 targeting agent in a ratio of labeled:unlabeled HER3 targeting agent of from about 0.01:10 to 1:1, such as 0.1:10 to 1:1 labeled:unlabeled.

Accordingly to certain aspects of the present invention, the HER3 targeting agent may be provided in a total protein or peptide amount of up to 100 mg, such as up to 60 mg, such as 5 mg to 45 mg, or a total protein amount of from 0.001 mg/kg patient weight to 3.0 mg/kg patient weight, such as from 0.005 mg/kg patient weight to 2.0 mg/kg patient weight, or from 0.01 mg/kg patient weight to 1 mg/kg patient weight, or from 0.1 mg/kg patient weight to 0.6 mg/kg patient weight, or 0.3 mg/kg patient weight, or 0.4 mg/kg patient weight, or 0.5 mg/kg patient weight, or 0.6 mg/kg patient weight.

The inventive combination of a radiolabeled fraction and an unlabeled fraction of the antibody or other targeting agent allows the composition to be tailored to a specific patient, wherein each of the radiation dose and the protein dose of the antibody or other targeting agent are personalized to that patient based on at least one patient-specific parameter. As such, each vial of the composition may be made for a specific patient, where the entire content of the vial is delivered to that patient in a single dose. When a treatment regime calls for multiple doses, each dose may be formulated as a patient specific dose in a vial to be administered to the patient as a "single dose" (i.e., full contents of the vial administered at one time). The subsequent dose may be formulated in a similar manner, such that each dose in the regime provides a patient specific dose in a single dose container. One of the advantages of such a composition is that there will be no left-over radiation that would need to be discarded or handled by the medical personnel, e.g., no dilution, or other manipulation to obtain a dose for the patient. When provided in a single dose container, the container may simply be placed in-line in an infusion tubing set for infusion to the patient. Moreover, the volume can be standardized so that there is a greatly reduced possibility of medical error (i.e., delivery of an incorrect dose, as the entire volume of the composition is to be administered in one infusion).

Thus, according to certain aspects, the HER3 targeting agent may be provided as a single dose composition which may be tailored to a specific patient, wherein the amount of radiolabeled and unlabeled HER3 targeting agent in the composition may depend on one or more of a patient weight, age, gender, disease state and/or health status, such as detailed in International Publication No. WO 2016/187514 and U.S. Pat. No. 10,736,975. According to certain aspects, the HER3 targeting agent may be provided as a multi-dose therapeutic, wherein each dose in the treatment regime is provided as a patient specific composition. The patient-specific composition includes radiolabeled and unlabeled HER3 targeting agents, wherein the amounts of each depend on one or more of patient weight, age, gender, disease state, and/or health status.

As used herein, the terms "subject" and "patient" are interchangeable and include, without limitation, a mammal such as a human, a non-human primate, a dog, a cat, a horse, a sheep, a goat, a cow, a rabbit, a pig, a rat and a mouse. Where the subject is human, the subject may be of any age. For example, the subject can be 60 years or older, 65 or older, 70 or older, 75 or older, 80 or older, 85 or older, or 90 or older. Alternatively, the subject can be 50 years or younger, 45 or younger, 40 or younger, 35 or younger, 30 or younger, 25 or younger, or 20 or younger. For a human subject afflicted with cancer, the subject can be newly diagnosed, or relapsed and/or refractory, or in remission.

As used herein, "treating" a subject afflicted with a cancer shall include, without limitation, (i) slowing, stopping or reversing the cancer's progression, (ii) slowing, stopping or reversing the progression of the cancer's symptoms, (iii) reducing the likelihood of the cancer's recurrence, and/or (iv) reducing the likelihood that the cancer's symptoms will recur. According to certain preferred aspects, treating a subject afflicted with a cancer means (i) reversing the cancer's progression, ideally to the point of eliminating the cancer, and/or (ii) reversing the progression of the cancer's symptoms, ideally to the point of eliminating the symptoms, and/or (iii) reducing or eliminating the likelihood of relapse (i.e., consolidation, which ideally results in the destruction of any remaining cancer cells).

"Chemotherapeutic", in the context of this invention, shall mean a chemical compound which inhibits or kills growing cells and which can be used or is approved for use in the treatment of cancer. Exemplary chemotherapeutic agents include cytostatic agents which prevent, disturb, disrupt or delay cell division at the level of nuclear division or cell plasma division. Such agents may stabilize microtubules, such as taxanes, in particular docetaxel or paclitaxel, and epothilones, in particular epothilone A, B, C, D, E, and F, or may destabilize microtubules such as vinca alkaloids, in particular vinblastine, vincristine, vindesine, vinflunine, and vinorelbine. Exemplary chemotherapeutics also include radiosensitizers that may synergize with the radiolabeled HER3, such as temozolomide, cisplatin, and/or fluorouracil.

"Therapeutically effective amount" or "effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics include, for example, improved well-being of the patient, reduction in a tumor burden, arrested or slowed growth of a tumor, and/or absence of metastasis of cancer cells to other locations in the body. According to certain aspects, "therapeutically effective amount" or "effective amount" refers to an amount of the radiolabeled HER3 targeting agent that may deplete or cause a reduction in the overall number of cells expressing HER3 and/or that may inhibit growth of cells expressing HER3, when used alone or in combination or conjunction with other agents and/treatment modalities.

As used herein, "depleting", with respect to cells expressing HER3, shall mean to lower the population of at least one type of cells that express or overexpress HER3 (e.g., HER3-positive cells in a solid tumor or circulating in a subject's blood). According to certain aspects of this invention, a decrease is determined by comparison of the numbers of HER3-positive cells in the subject's blood or in a tissue biopsy, such as from the solid tumor, before and after initiation of treatment with the HER3 targeting agent. As such, and by way of example, a subject's HER3-positive cells may be considered to be depleted if the population is lowered, such as by at least 10%, 20%, 30%, 40%, 50%, 60%, 70%, 80%, 90% or 99%.

"Inhibits growth" refers to a measurable decrease or delay in the growth of a malignant cell or tissue (e.g., tumor) in vitro or in vivo when contacted with a therapeutic or a combination of therapeutics or drugs, when compared to the decrease or delay in the growth of the same cells or tissue in the absence of the therapeutic or the combination of therapeutic drugs. Inhibition of growth of a malignant cell or tissue in vitro or in vivo may be at least about 10%, 20%, 30%, 40%, 50%, 60%, 70%, 80%, 90%, 95%, 96%, 97%, 98%, 99%, or 100%.

The term "immune checkpoint therapy" refers to a molecule capable of modulating the function of an immune checkpoint protein in a positive or negative way in the furtherance of immune response against cancer cells. The term "immune checkpoint" refers to a protein directly or indirectly involved in an immune pathway that under normal physiological conditions acts to prevent uncontrolled immune reactions and thus for the maintenance of self-tolerance and/or tissue protection.

In the context of the present invention, an immune checkpoint therapy encompasses therapies such as antibodies capable of down-regulating at least partially the function of an inhibitory immune checkpoint (antagonist) and/or up-regulating at least partially the function of a stimulatory immune checkpoint (agonist). As example, an immune checkpoint therapy may refer to an antibody against an immune checkpoint inhibitor (ICI) that may be upregulated in certain cancers, and thus may inhibit the function of the ICI.

The term "DDRi" refers to an inhibitor of a DNA damage response pathway protein, of which a PARPi is an example. The term "PARPi" refers to an inhibitor of poly(ADP-ribose) polymerase. In the context of the present invention, the term PARPi encompasses molecules that may bind to and inhibitor the function of poly(ADP-ribose) polymerase, such as antibodies, peptides, or small molecules.

The term "CD47 blockade" refers to an agent that prevents CD47 binding to SIRPα, such as blocking agents that bind to either of CD47 or SIRPα, or those that modulate expression of CD47 or SIRPα, or those that otherwise inhibit the CD47/SIRPα axis. Without limitation, CD47 blockades encompass at least antibodies that bind to CD47 such as magrolimab, lemzoparlimab, and AO-176, SIRPα fusion proteins such as TTI-621 and TTI-622, agents that modulate the expression of CD47 and/or SIRPα, such as phosphorodiamidate morpholino oligomers (PMO) that block translation of CD47, and small molecule agents such as RRx-001.

As used herein, administering to a subject one or more additional therapies, such as one or more of an immune checkpoint therapy and/or DDRi and/or CD47 blockade and/or radiosensitizer "in conjunction with" a HER3 targeting agent means administering the additional therapy before, during and/or after administration of the HER3 targeting agent. This administration includes, without limitation, the following scenarios: (i) the additional therapy is administered first, and the HER3 targeting agent is administered second; (ii) the additional therapy is administered concurrently with the HER3 targeting agent (e.g., the DDRi is administered orally once per day for n days, and the HER3 targeting agent is administered intravenously in a single dose on one of days 2 through n−1 of the DDRi regimen); (iii) the additional therapy is administered concurrently with the HER3 targeting agent (e.g., the DDRi is administered orally for a duration of greater than one month, such as orally once per day for 35 days, 42 days, 49 days, or a longer period during which the cancer being treated does not progress and during which the DDRi does not cause unacceptable toxicity, and the HER3 targeting agent is administered intravenously in a single dose on a day within the first month of the DDRi regimen); and (iv) the HER3 targeting agent is administered first (e.g., intravenously in a single dose or a plurality of doses over a period of weeks), and the additional therapy is administered second (e.g., the DDRi is administered orally once per day for 21 days, 28 days, 35 days, 42 days, 49 days, or a longer period during which the cancer being treated does not progress and during which the DDRi does not cause unacceptable toxicity). Additional permutations that would be obvious to one of skill in the art are possible and within the scope of the presently claimed invention.

An "article of manufacture" indicates a package containing materials useful for the treatment, prevention and/or diagnosis of the disorders described herein. The article of manufacture may include a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition may be a radiolabeled HER3 targeting agent according to aspects of the presently disclosed invention.

A "label" or "package insert" is used to refer to instructions customarily included in commercial packages of therapeutic products that contain information about the indications, usage, dosage, administration, combination therapy, contraindications and/or warnings concerning the use of such therapeutic products. As used herein, a label may indicate that the composition is used for treating a HER3-positive cancer and may optionally indicate administration routes and/or methods. Moreover, the article of manufacture may include (a) a first container with a composition contained therein, wherein the composition includes HER3 targeting agent; and (b) a second container with a composition contained therein, wherein the composition includes a further cytotoxic or otherwise therapeutic agent according to aspects of the presently disclosed invention. Alternatively, or additionally, the article of manufacture may further include a second (or third) container including a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Throughout this application, various patents, patent applications and other publications are cited, each of which is hereby incorporated by reference in its entirety.

Unless otherwise defined, all technical and scientific terms used herein have the same meaning as commonly understood by one of ordinary skill in the art to which the present invention belongs. Although methods and materials similar or equivalent to those described herein can be used in the practice or testing described herein, suitable methods and materials are described below.

Experimental Results

An anti-HER3 IgG monoclonal antibody consisting of heavy chain SEQ ID NO:77 and light chain SEQ ID NO:78 was prepared, conjugated to the chelator DOTA using p-SCN-Bn-DOTA and radiolabeled via chelation with Actinium-225 for further investigation as described below in connection with FIGS. 3-11.

FIG. 3 shows ELISA assay binding characteristics of an Ac225 labeled DOTA-conjugated anti-HER3 monoclonal antibody ("HER3-ARC") versus the unmodified anti-HER3 antibody and a non-specific antibody (IgG), demonstrating that the modifications do not materially affect immune reactivity to HER3.

The binding properties of 225Ac-HER3-ARC were evaluated by ELISA. A 96 well plate was coated with human recombinant HER3 overnight following by incubation of serial dilutions (0-100 μg/ml) of anti-HER3, 225Ac-HER3-ARC and IgG (immunoglobulin 1, nonpecific IgG1 control) for 1 h at room temperature. A secondary antibody (Goat Anti-human IgG F(ab')20-HRP) was added and incubated for 30 min on ice followed by color development using HCl 1M for 10 min. The sample absorbance was measured at 450 nm. $^{225}$Ac-HER3-ARC showed similar binding properties to those of the native antibody by ELISA (HER3-ARC: $EC_{50}$=0.0017 μg/ml, HER3 $EC_{50}$=0.0022 μg/ml).

Figure 4:
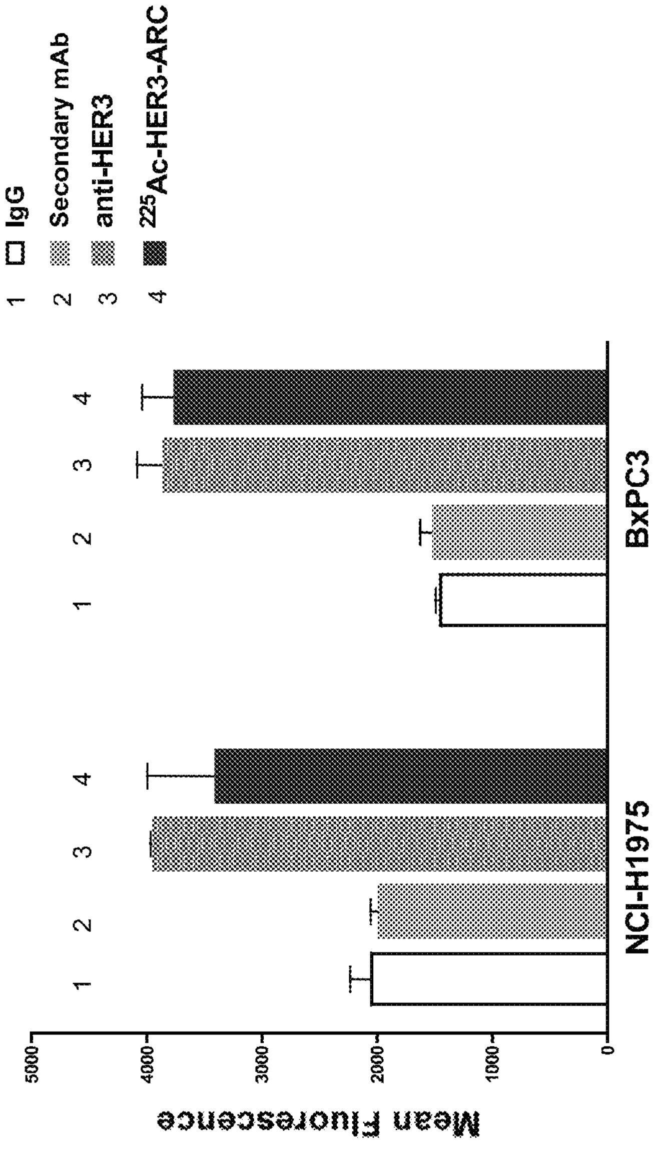
FIG. 4 is a graph showing the results of flow cytometry assays examining the binding of the 225Ac-HER3-ARC, the unmodified anti-HER3 mAb, non-specific antibody control (IgG), and secondary antibody only control to HER3-positive NCI-H1975 cells (human lung adenocarcinoma, NSCLC) and BxPC-3 cells (human pancreatic adenocarcinoma).

FIG. 4 is a graph showing the results of flow cytometry assays examining the binding of the 225Ac-HER3-ARC, the unmodified anti-HER3 mAb, non-specific antibody control (IgG), and secondary antibody only control to HER3-positive NCI-H1975 cells (human lung adenocarcinoma, NSCLC) and BxPC-3 cells (human pancreatic adenocarcinoma).

The binding properties of 225Ac-HER3-ARC were evaluated by flow cytometry in HER3+ cells (NCI-H1975 and BxPC3). Solutions (100 μg/ml) of anti-HER3, 225Ac-HER3-ARC and IgG (immunoglobulin 1, nonspecific IgG1) were added to HER+ cells and incubated for 1 h at room temperature. A PE labeled secondary antibody was added and incubated for 30 min on ice. Sample fluorescence was measured using a flow cytometer. The binding properties of 225Ac-HER3-ARC to HER3+ positive cell lines resembled those of the unmodified anti-HER3 mAb.

Figure 5:
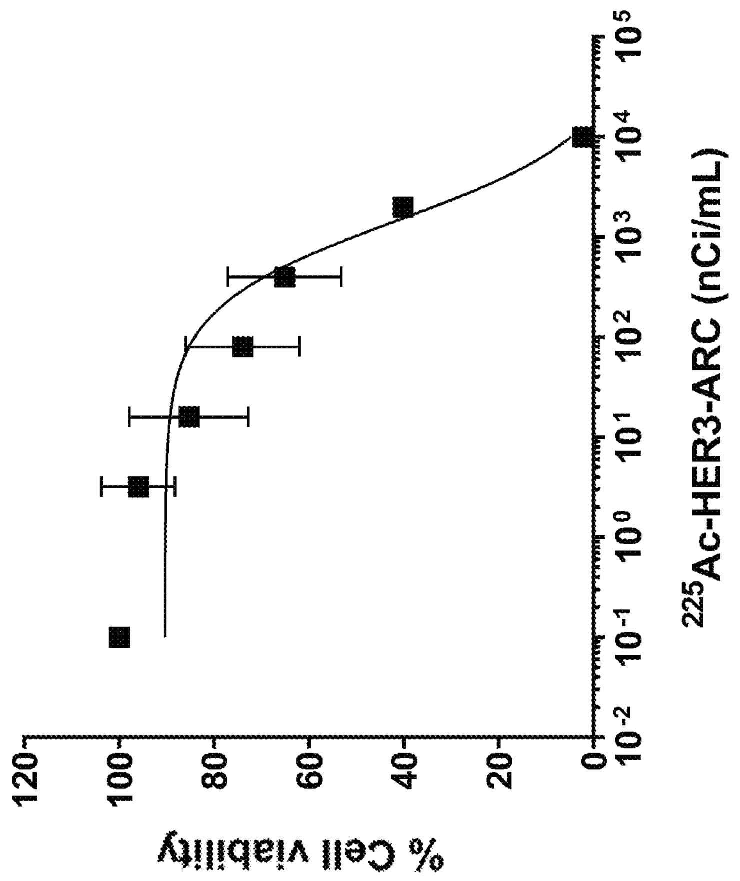
FIG. 5 is a graph showing the in vitro cytotoxic effect of 225Ac-HER3-ARC to HER3-positive cell line NCI-H1975 as a function of radiation dose.

FIG. 5 is a graph showing the in vitro cytotoxic effect of 225Ac-HER3-ARC to HER3-positive cell line NCI-H1975 as a function of radiation dose.

The cytotoxic effects of 225Ac-HER3-ARC to HER3+ cell line NCI-H1975 were evaluated in a colorimetric assay using CellTiter 96® AQueous Non-Radioactive Cell Proliferation Assay (MTS). NCI-H1975 cells were incubated with 225Ac-HER3-ARC for 24 h at 37° C. Unbound 225Ac-HER3-ARC was then removed, and cells were cultured for 72 h at 37° C. Absorbance at 490 nm was measured and % of cell viability calculated. 225Ac-HER3-ARC showed potent in vitro cytotoxicity against HER3+ cell line NCI-H1975.

Figure 6A:
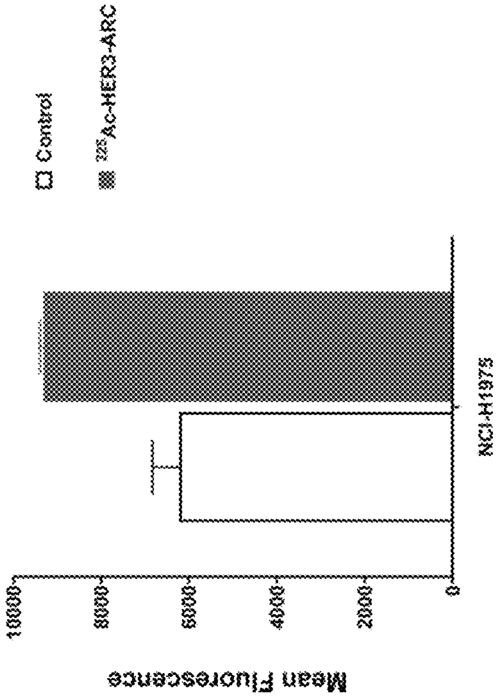
FIG. 6A is a graph showing that 225Ac-HER3-ARC upregulates cell surface calreticulin (CRT) in NCI-H1975 cells.
Figure 6B:
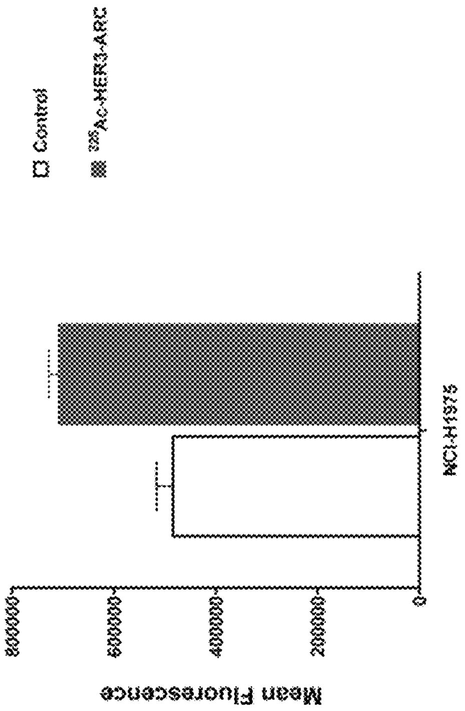
FIG. 6B is a graph showing that 225Ac-HER3-ARC upregulates CD47 on NCI-H1975 cells.

FIG. 6A is a graph showing that 225Ac-HER3-ARC upregulates cell surface calreticulin (CRT) in NCI-H1975 cells and FIG. 6B is a graph showing that 225Ac-HER3-ARC upregulates CD47 on NCI-H1975 cells.

The effect of 225Ac-HER3-ARC on cell surface expression of calreticulin (CRT) and CD47 by HER3+ cell line NCI-H1975 was examined using flow cytometry. Cells were treated with 225Ac-HER3-ARC (100 nCi/ml) or PBS (control) for 72 h. Following treatment, cells were stained for CRT and CD47. The results demonstrate that each of CRT (FIG. 6A) and CD47 (FIG. 6B) is upregulated by 225Ac-HER3-ARC in NCI-H1975 cells.

Figure 7A:
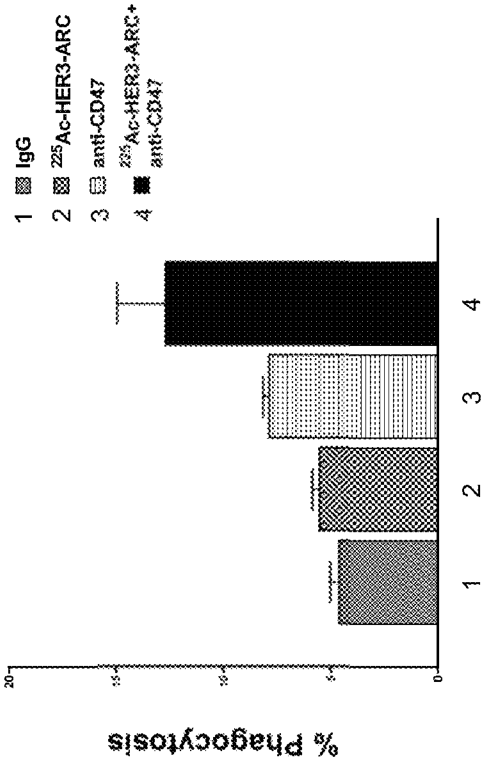
FIG. 7A is a graph showing results of a phagocytosis assay demonstrating that the combination of 225Ac-HER3-ARC and an anti-CD47 blocking antibody enhanced phagocytosis of BxPC-3 cells versus either treatment alone.
Figure 7B:
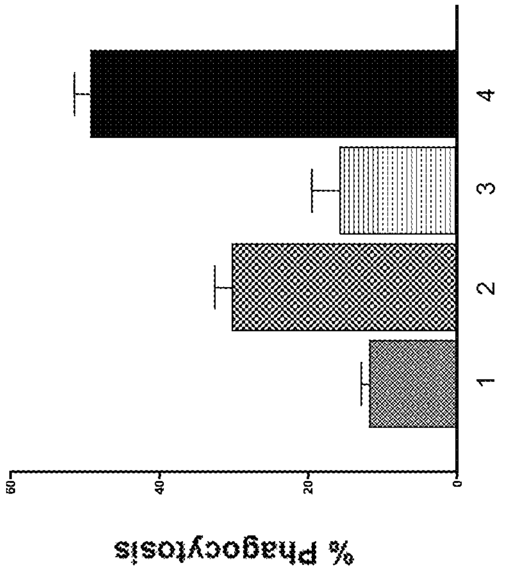
FIG. 7B is a graph showing results of a phagocytosis assay demonstrating that the combination of 225Ac-HER3-ARC and an anti-CD47 blocking antibody enhanced phagocytosis of NCI-H1975 cells versus either treatment alone.

FIG. 7A is a graph showing results of a phagocytosis assay demonstrating that the combination of 225Ac-HER3-ARC and an anti-CD47 blocking antibody enhanced phagocytosis of BxPC-3 cells versus either treatment alone. FIG. 7B is a graph showing results of a phagocytosis assay demonstrating that the combination of 225Ac-HER3-ARC and an anti-CD47 blocking antibody enhanced phagocytosis of NCI-H1975 cells versus either treatment alone. The same key applies for FIGS. 7A and 7B.

The effect of combining 225Ac-HER3-ARC and anti-CD47 on phagocytosis in vitro was evaluated by flow cytometry. BxPC-3 (FIG. 7A) and NCI-H1975 (FIG. 7B) cells were seeded in 6-well plates 24 hr prior to a 24 hr incubation at 37° C. with 225Ac-HER3-ARC. Following 225Ac-HER3-ARC treatment, cells were cultured for 72 hr at 37° C.

BxPC-3 and NCI-H1975 cells were stained with Vybrant DiD cell-labeling solution and treated with anti-human CD47 (Bio X Cell, Cat#BE0019) and mouse IgG1 isotype control (Bio X Cell, Cat#BE0083) for 1 hr at 37° C. Human macrophages were stained with Vybrant DiO cell-labeling solution. Labeled human macrophages and target cells were cocultured for 2 h at 37° C. Phagocytosis was assessed by evaluating the dual labeled cells (DiD+/DiO+).

Figure 8:
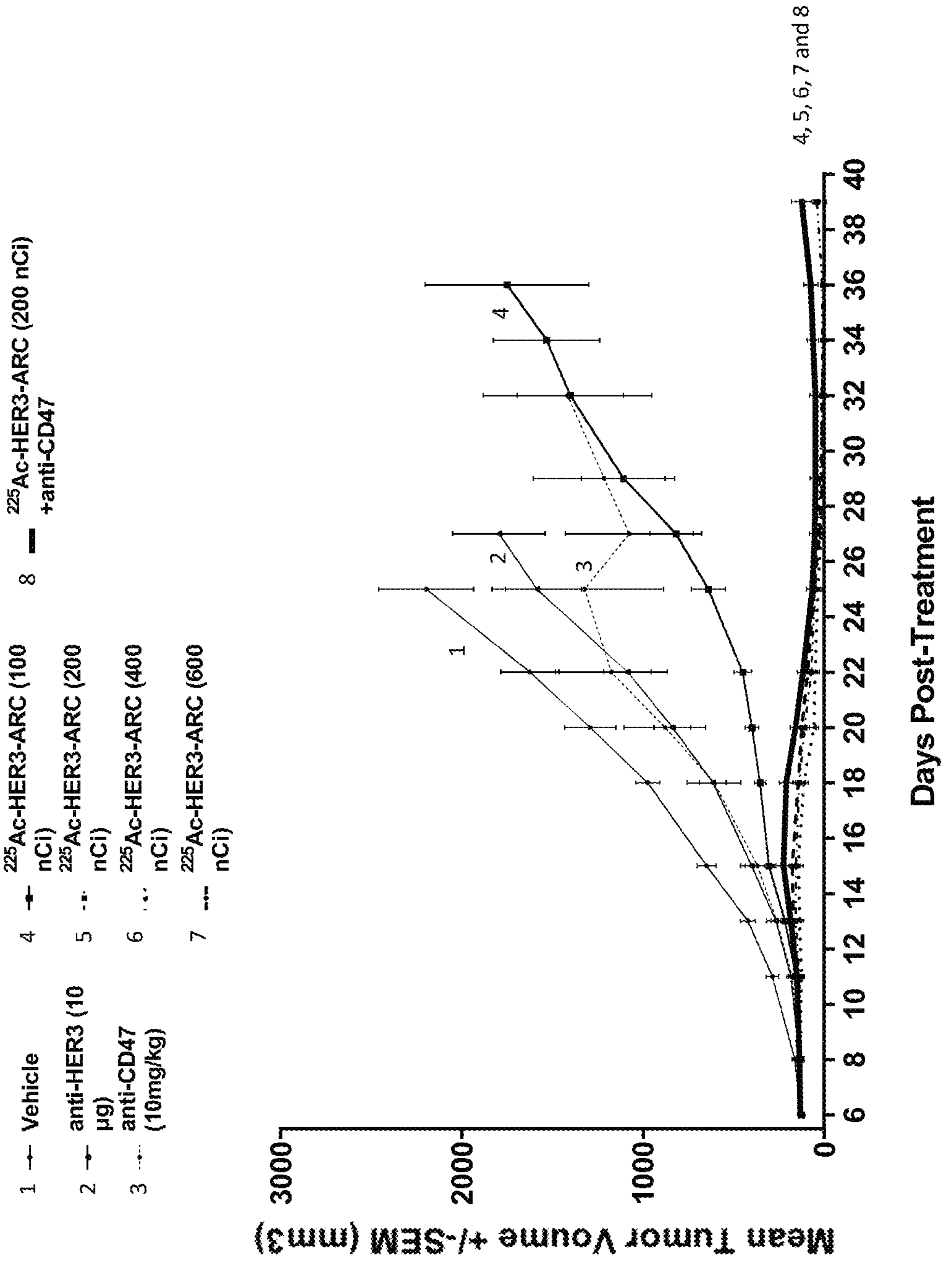
FIG. 8 is graph showing the effects on tumor growth, in a human tumor (NCI-H1975 cell) mouse xenograft model, of a 225Ac-HER3-ARC at different radiation doses and in combination with an anti-CD47 blocking antibody.

FIG. 8 is graph showing the effects on tumor growth, in a human tumor (NCI-H1975 cell) mouse xenograft model, of a 225Ac-HER3-ARC at different radiation doses (100 nCi, 200 nCi, 400 nCi, 600 nCi) alone and at 200 nCi in combination with an anti-CD47 blocking antibody, of unlabeled anti-HER3 mAb, of anti-CD47 blocking antibody alone, and of vehicle-only control. Notably, tumor growth was almost entirely suppressed by 225Ac-HER-ARC at each of radiation doses 200 nCi, 400 nCi, 600 nCi and by the combination of 225Ac-HER-ARC (200 nCi) with the anti-CD47 mAb.

Figure 9:
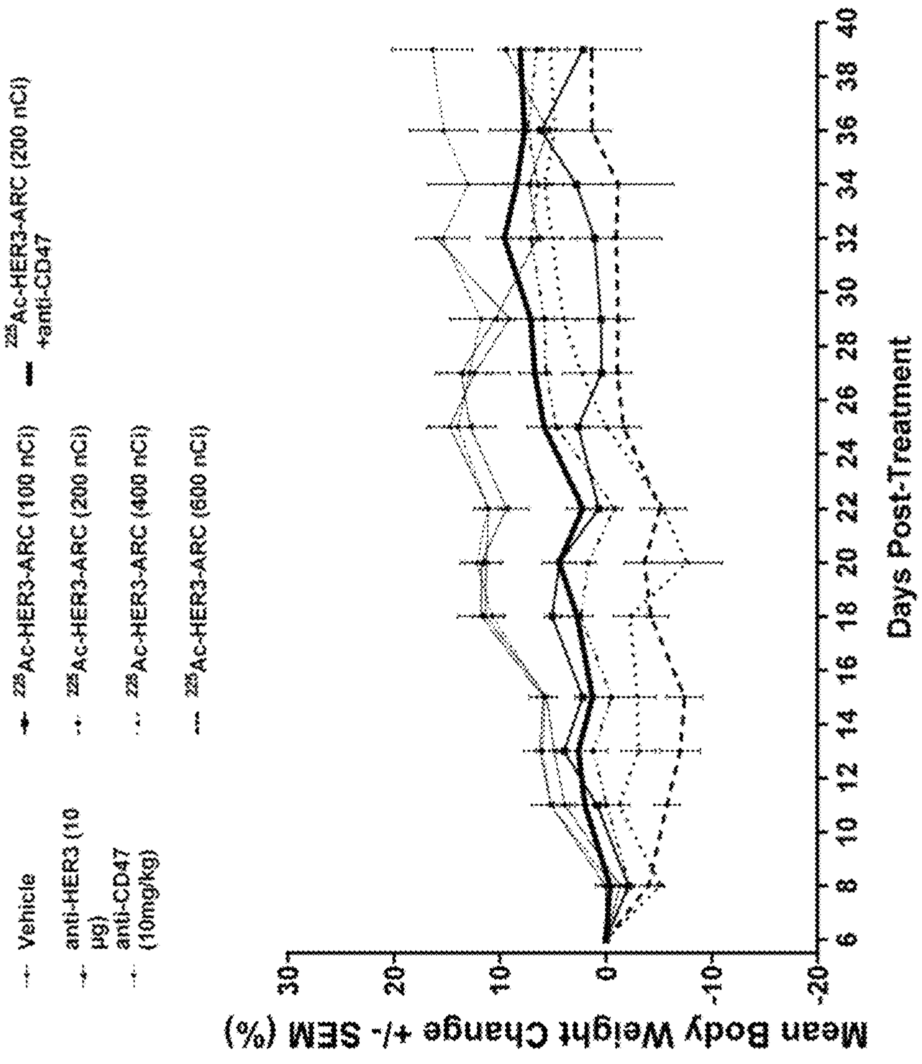
FIG. 9 is a graph showing body weight over time for the subjects of the experiment described in FIG. 8.

FIG. 9 is a graph showing body weight over time for the subjects of the experiment described in FIG. 8.

Figure 10:
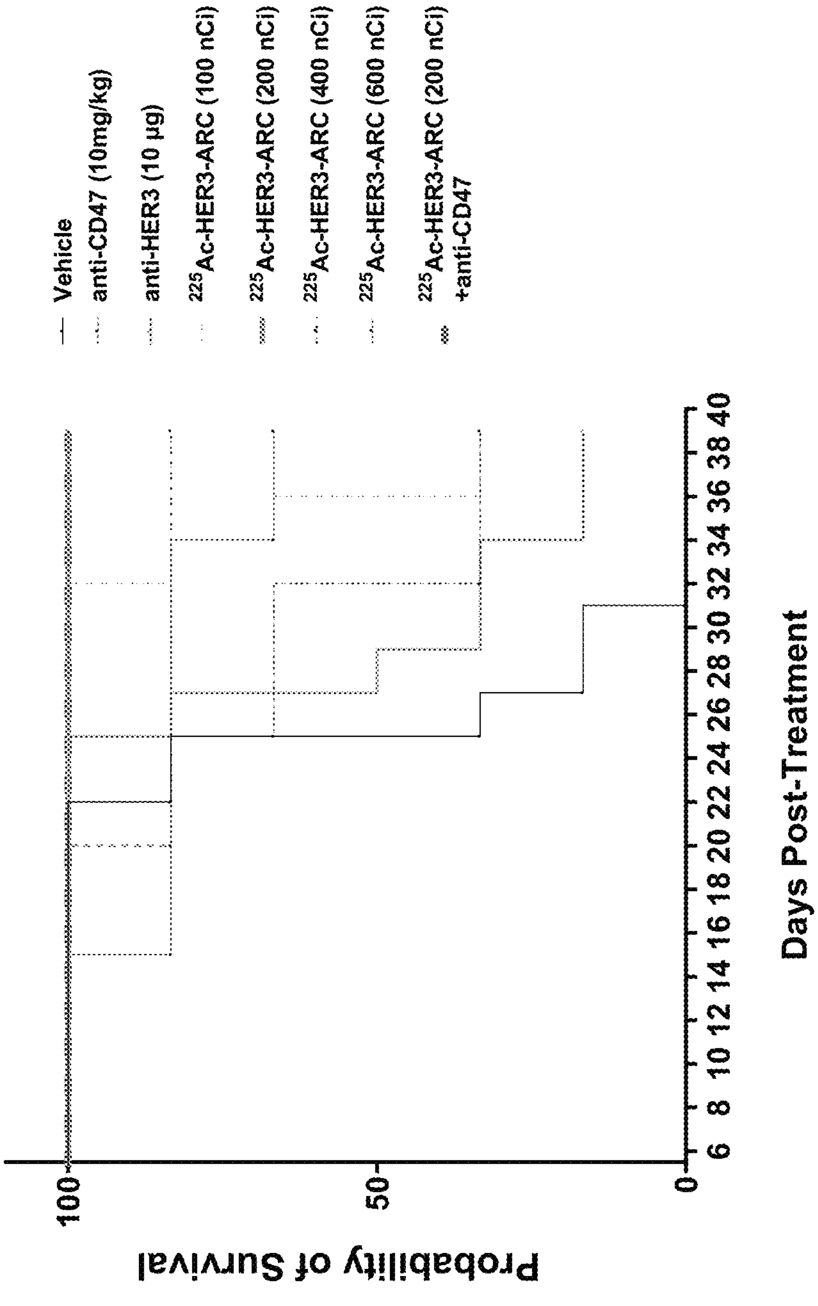
FIG. 10 is a graph showing the probability of survival over time for the experimental group subjects of the experiment described in FIG. 8

FIG. 10 is a graph showing the probability of survival over time for the experimental group subjects of the experiment described in FIG. 8.

Tumor xenograft studies examining the effect of HER2-ARC treatment alone and in combination with CD47 blockade on HER2-positive tumor growth were also performed. Anti-HER2 mAb Trastuzumab was chemically conjugated to DOTA using p-SCN-Bn-DOTA and labeled, via chelation, with either Actinium-225 or Lutetium-177 for use in these experiments.

Figure 11:
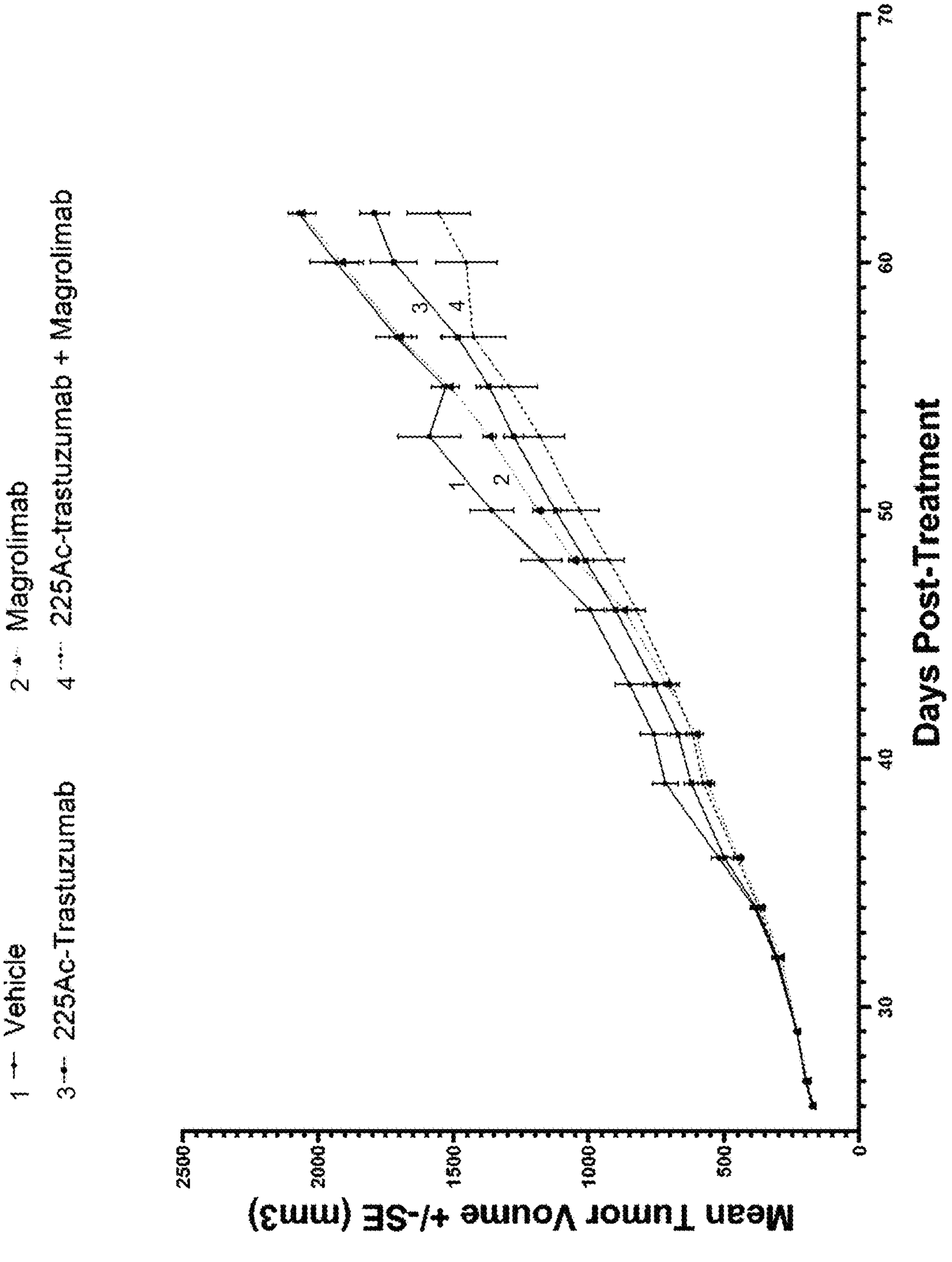
FIG. 11 is a graph showing the comparative effects on tumor growth of vehicle (control), CD47 blocking antibody magrolimab alone, 225Ac-trastuzumab alone, and the combination of magrolimab and 225Ac-trastuzumab in an NGS mouse xenograft model using the HER2-positive SK-OV3 human ovarian cancer cell line.

FIG. 11 is a graph showing the comparative effects on tumor growth of vehicle only (control), magrolimab alone (10 mg/kg), 225Ac-trastuzumab alone (0.025 μCi/animal), and the combination of magrolimab (10 mg/kg) and 225Ac-trastuzumab (0.025 μCi/animal), in an NGS mouse xenograft model using the HER2-positive SK-OV3 human ovarian cancer cell line. Each cohort consisted of eight animals.

Figure 12:
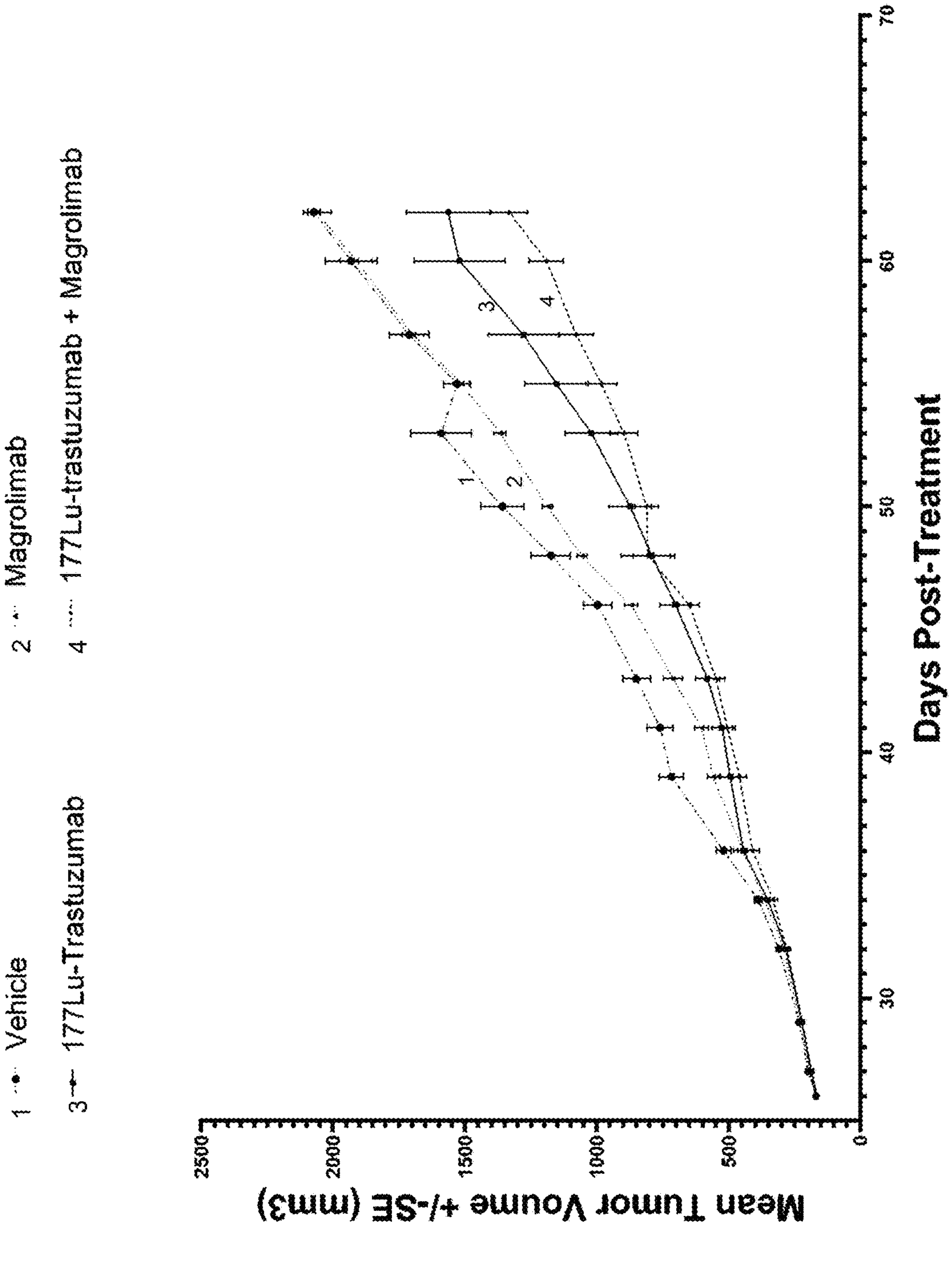
FIG. 12 is a graph showing the comparative effects on tumor growth of vehicle (control), magrolimab alone, 177Lu-trastuzumab alone, and the combination of magrolimab and 177Lu-trastuzumab in an NGS mouse xenograft model using the SK-OV3 human ovarian cancer cell line.

FIG. 12 is a graph showing the comparative effects on tumor growth of vehicle only (control), magrolimab alone (10 mg/kg), 177Lu-trastuzumab alone (25 μCi/animal), and the combination of magrolimab (10 mg/kg) and 177Lu-trastuzumab (25 μCi/animal), in an NGS mouse xenograft model using the HER2-positive SK-OV3 human ovarian cancer cell line. Each cohort consisted of eight animals.

ASPECTS OF THE INVENTION

It is well documented in both preclinical and clinical studies that levels of HER3 can become downregulated following administration of a HER3-targeting antibody (Mishra, 2018). In preclinical models with lumretuzumab, there was a dose-dependent (1-10 mg/kg) downregulation of HER3 as measured by both immunohistochemistry and Western blotting (Maneses-Lorenta, 2015; Mirshberger, 2013). The lowest dose of lumretuzumab (0.3 mg/kg) did not result in HER3 target downregulation (Maneses-Lorenta, 2015), and these low levels of lumretuzumab (0.1 mg/kg and 0.3 mg/kg) were ineffective at controlling HER3-expressing tumors (Mirshberger, 2013). In clinical studies with lumretuzumab, downregulation of surface HER3 was observed in serial tumor biopsies in 92% of patients across all dose levels tested (100-2000 mg; Meulendijks, 2016). Additionally, a decrease in total HER3 levels was observed in three out of five paired tumor biopsy samples in patients treated with the HER3-targeting antibody LJM716 at 40 mg/kg (Reynolds, 2017).

While the internalization and degradation of HER3 may be beneficial to reduce phosphorylation of HER3 and subsequent signaling activity, reduction of surface levels of HER3 may impede antibody targeting of tumors. Therefore, if repeat administration of a HER3-targeting antibody is desired or required for efficacy, the administration of a HER3-targeting antibody may result in downregulation of the target and preclude re-dosing. The present inventors have found use of antibody radioconjugates (ARCs) circumvent the problems associated with the dose-dependent downregulation of HER3 as the lower antibody doses useful in therapeutic methods may not cause HER3 downregulation. Accordingly, the present inventors have found that HER3 targeting agents including a radioisotope are effective as diagnostic and therapeutic agents for improved tumor targeting and killing of HER3-expressing cancer cells, such as certain solid tumors. In particular, therapeutic methods that may include multiple doses of a HER3-targeting agent may provide improved tumor targeting and killing without causing a detrimental level of HER3 downregulation.

Thus, according to certain aspects of the presently disclosed invention, therapeutic methods for treating HER3-positive cancers using a radiolabeled HER3 targeting agent are provided. The methods may also include diagnostic steps to determine if and/or to what extent a patient has a HER3-positive cancer and/or the localization of such cancer, for example, by identifying and/or quantifying HER3 positive cells within solid tumors or circulating in a blood sample from the patient.

According to certain aspects, the therapeutic methods include administration of a radiolabeled HER3 targeting agent, such as a radiolabeled antibody, peptide, or small molecule that targets HER3, either alone or in combination with one or more additional therapeutic agents or modalities. According to certain aspects, the additional agent or modality may be any one or more of administration of an immune checkpoint therapy, a DDRi, a CD47 blockade, a chemotherapeutic agent, a small molecule oncology drug, external beam radiation, and brachytherapy.

According to certain aspects, the radiolabeled HER3 targeting agent may be administered to the patient in a patient specific composition in one or more doses.

According to certain aspects, the patient may be monitored at intervals during the therapy for the presence of HER3-positive cells to evaluate the reduction in HER3-positive cells. Detecting a decreased number of the HER3-positive cells after treatment with the HER3 targeting agent, as compared to the number of HER3-positive cells prior to treatment may indicate effectiveness of the HER3 targeting agent in treating a HER3-positive cancer in the mammalian subject.

According to certain aspects, the method of treating cancer includes identifying a patient having a HER3-positive cancer by identifying HER3-positive cells and administering to the patient an effective amount of a HER3 targeting agent, either alone or in combination with an additional method of treatment. According to certain aspects, the additional method of treatment may be any one or more of administration of an immune checkpoint therapy, a DDRi, a CD47 blockade, a chemotherapeutic agent, a small molecule oncology drug, external beam radiation and brachytherapy.

According to certain aspects, the chemotherapeutic agent is a radiosensitizer.

According to certain aspects, the radiolabeled HER3 targeting agent can be administered to a patient that has undergone, such as recently undergone a treatment, such as surgery for treatment of the cancer, such as to remove all or a portion of a solid tumor. Thus, for example, the radiolabeled HER3 targeting agent may be administered perioperatively or post-operatively.

HER3 Targeting Agents

An object of the presently disclosed invention is to provide radiolabeled HER3-, such as human HER3-, targeting agents for diagnostic use and/or for therapeutic use, such as in the diagnosis and/or treatment of HER3-positive cancers. Radiolabeled HER3-targeting agents can effect a therapeutic response via the delivery of DNA-damaging ionizing radiation to cells, for example, alpha-particles that induce double strand DNA breaks and cell death.

Exemplary anti-HER3 antibodies (also referred to as “HER3 antibodies” herein), such as anti-human HER3 antibodies, that that may be radiolabeled and embodied in and/or used in the various aspect of the presently disclosed invention include, without limitation, the following antibodies, and antibodies such as but not limited to immunoglobulins, such as but not limited to IgG, that (i) include the heavy chain variable region of the HER3 antibody or heavy chain, (ii) include 1, 2 or 3 of the heavy chain CDRs (e.g., by the Kabat definition) of the HER3 antibody or heavy chain or those recited, (iii) include the light chain variable region of the HER3 antibody or light chain, and/or (iv) include 1, 2 or 3 of the light chain CDRs (e.g., by the Kabat definition) of the HER3 antibody or light chain or those recited. It should also be understood that where a HER3 antibody heavy chain or HER3 antibody light chain is disclosed that includes an N-terminal leader sequence, also intended to be disclosed for embodiment in and use in the various aspects of the invention are corresponding heavy chains and corresponding light chains that lack the leader sequence.

An exemplary HER3 antibody that may be radiolabeled and embodied in and/or used inthe presently disclosed invention may, for example, include a murine monoclonal antibody against HER3 including a heavy chain having the amino acid sequence as set forth in SEQ ID NO:9 or 11 and/or a light chain having the amino acid sequence as set forth in SEQ ID NO:10 or 12, or an antibody such as a humanized antibody derived from one or more of said sequences. An exemplary HER3 antibody that may be radiolabeled and embodied in and/or used in the presently disclosed invention may include or a heavy chain with an N-terminal region having the sequence set forth in SEQ ID NO:13 and/or a light chain with an N-terminal region having the sequence as set forth in SEQ ID NO:14. A HER3 antibody that may be similarly embodied or used in various aspect of the invention may, for example, include the heavy chain variable region having the amino acid sequence as set forth in SEQ ID NO:7, and/or a light chain variable region having an amino acid sequence as set forth in SEQ ID NO:8; and/or a heavy chain including one or more of CDR1, CDR2 and CDR3 having the amino acid sequences respectively set forth in SEQ ID NOS:1-3, and/or a light chain with one or more of the CDR1, CD2 and CDR3 having the amino acid sequences respectively set forth in SEQ ID NOS:4-6. See FIGS. 1 and 2 for a further description of these sequences. A HER3 antibody embodied in and/or used in any of the aspects of the invention may, for example, include any combination of the aforementioned light chain sequences and/or heavy chain sequences.

An exemplary HER3 antibody includes an immunoglobulin heavy chain variable region including a CDR-H1 including SEQ ID NO:15, a CDR-H2 including SEQ ID NO:16, and a CDR-H3 including SEQ ID NO:17, and/or an immunoglobulin light chain variable region including a CDR-L1 including SEQ ID NO:18, a CDR-L2 including SEQ ID NO:19, and a CDR-L3 including SEQ ID NO:20. An exemplary An exemplary HER3 antibody includes an immunoglobulin heavy chain variable region including SEQ ID NO:21 and/or an immunoglobulin light chain variable region including SEQ ID NO:22. An exemplary HER3 antibody includes an immunoglobulin heavy chain amino acid sequence of SEQ ID NO:23 and/or an immunoglobulin light chain amino acid sequence of SEQ ID NO:24.

An exemplary HER3 antibody includes an immunoglobulin heavy chain variable region including a CDR-H1 including SEQ ID NO:25, a CDR-H2 including SEQ ID NO:26, and a CDR-H3 including SEQ ID NO:27; and/or an immunoglobulin light chain variable region including a CDR-L1 including SEQ ID NO:28, a CDR-L2 including SEQ ID NO:29, and a CDR-L3 including SEQ ID NO:30. An exemplary HER3 antibody includes an immunoglobulin heavy chain variable region including SEQ ID NO:31 and/or an immunoglobulin light chain variable region including SEQ ID NO:32. An exemplary HER3 antibody includes an immunoglobulin heavy chain amino acid sequence of SEQ ID NO:33 and/or an immunoglobulin light chain amino acid sequence of SEQ ID NO:34

An exemplary HER3 antibody includes an immunoglobulin heavy chain variable region including a CDR-H1 including SEQ ID NO:35, a CDR-H2 including SEQ ID NO:36, and a CDR-H3 including SEQ ID NO:37; and/or an immunoglobulin light chain variable region including a CDR-L1 including SEQ ID NO:38, a CDR-L2 including SEQ ID NO:39, and a CDR-L3 including SEQ ID NO:40. An exemplary HER3 antibody includes an immunoglobulin heavy chain variable region including SEQ ID NO:41, and/or an immunoglobulin light chain variable region SEQ ID NO:42. An exemplary HER3 antibody includes an immunoglobulin heavy chain amino acid sequence of SEQ ID NO:43 and an immunoglobulin light chain amino acid sequence of SEQ ID NO:44.

An exemplary HER3 antibody includes an immunoglobulin heavy chain variable region including a CDR-H1 including SEQ ID NO:45, a CDR-H2 including SEQ ID NO:46, and a CDR-H3 including SEQ ID NO:47; and/or an immunoglobulin light chain variable region including a CDR-L1 including SEQ ID NO:48, a CDR-L2 including SEQ ID NO:29, and a CDR-L3 including SEQ ID NO:49. An exemplary HER3 antibody includes an immunoglobulin heavy chain variable region including SEQ ID NO:50 and/or an immunoglobulin light chain variable region including SEQ ID NO:51. An exemplary HER3 antibody includes an immunoglobulin heavy chain amino acid sequence of SEQ ID NO:52 and/or an immunoglobulin light chain amino acid sequence of SEQ ID NO:53.

An exemplary HER3 antibody includes an immunoglobulin heavy chain variable region including a CDR-H1 including SEQ ID NO:54, a CDR-H2 including SEQ ID NO:55, and a CDR-H3 including SEQ ID NO:56; and/or an immunoglobulin light chain variable region including a CDR-L1 including SEQ ID NO:28, a CDR-L2 including SEQ ID NO:29, and a CDR-L3 including SEQ ID NO:30. An exemplary HER3 antibody includes an immunoglobulin heavy chain variable region including SEQ ID NO:57 and/or an immunoglobulin light chain variable region including SEQ ID NO:58. An exemplary HER3 antibody includes an immunoglobulin heavy chain amino acid sequence of SEQ ID NO:59 and/or an immunoglobulin light chain amino acid sequence of SEQ ID NO: 60.

An exemplary HER3 antibody includes an immunoglobulin heavy chain variable region including a CDR-H1 including SEQ ID NO:61, a CDR-H2 including SEQ ID NO:62, and a CDR-H3 including SEQ ID NO:63; and/or an immunoglobulin light chain variable region including a CDR-L1 including SEQ ID NO:64, a CDR-L2 including SEQ ID NO:65, and a CDR-L3 including SEQ ID NO:66. An exemplary HER3 antibody includes an immunoglobulin heavy chain variable region including SEQ ID NO:67, and/or an immunoglobulin light chain variable region including SEQ ID NO:68. An exemplary HER3 antibody includes an immunoglobulin heavy chain amino acid sequence of SEQ ID NO:69 and an immunoglobulin light chain amino acid sequence of SEQ ID NO:70.

An exemplary HER3 antibody includes an immunoglobulin heavy chain variable region including a CDR-H1 including SEQ ID NO:71, a CDR-H2 including SEQ ID NO:72, and a CDR-H3 including SEQ ID NO:66; and/or an immunoglobulin light chain variable region including a CDR-L1 including SEQ ID NO:28, a CDR-L2 including SEQ ID NO:29, and a CDR-L3 including SEQ ID NO:30. An exemplary HER3 antibody includes an immunoglobulin heavy chain variable region including SEQ ID NO:73, and/or an immunoglobulin light chain variable region including SEQ ID NO:74. An exemplary HER3 antibody includes an immunoglobulin heavy chain amino acid sequence of SEQ ID NO:75 and/or an immunoglobulin light chain amino acid sequence of SEQ ID NO:76.

An exemplary HER3 antibody includes an immunoglobulin heavy chain amino acid sequence of SEQ ID NO:77 and/or an immunoglobulin light chain amino acid sequence of SEQ ID NO:78.

An exemplary HER3 antibody includes an immunoglobulin light chain variable region including SEQ ID NOS:86, 87, 88, 89, 90 or 91 and/or a heavy chain variable region including SEQ ID NOS:79, 80, 81, 82, 83, 84 or 85.

An exemplary HER3 antibody includes an immunoglobulin heavy chain sequence including SEQ ID NO:92, 94, 95, 98 or 99 and/or an immunoglobulin light chain sequence including SEQ ID NO:93, 96, 97, 100 or 101.

Exemplary HER3 antibodies also include Barecetamab (ISU104) from Isu Abxis Co and any of the HER3 antibodies disclosed in U.S. Pat. No. 10,413,607.

Exemplary HER3 antibodies also include HMBD-001 (10D1F) from Hummingbird Bioscience Pte. and any of the HER3 antibodies disclosed in International Pub. Nos. WO 2019185164 and WO2019185878, U.S. Pat. No. 10,662, 241; and U.S. Pub. Nos. 20190300624, 20210024651, and 20200308275.

Exemplary HER3 antibodies also include the HER2/HER3 bispecific antibody MCLA-128 (i.e., Zenocutuzumab) from Merus N.V.; and any of the HER3 antibodies, whether monospecific or multi-specific, disclosed in U.S. Pub. Nos. 20210206875, 20210155698, 20200102393, 20170058035, and 20170037145.

Exemplary HER3 antibodies also include the HER3 antibody Patritumab (U3-1287), an antibody including heavy chain sequence SEQ ID NO:106 and/or light chain sequence SEQ ID NO:7 which are reported chains of Patritumab, and any of the HER3 antibodies disclosed in U.S. Pat. Nos. 9,249,230 and 7,705,130 and International Pub. No. WO2007077028.

Exemplary HER3 antibodies also include the HER3 antibody MM-121 and any of the HER3 antibodies disclosed in U.S. Pat. No. 7,846,440 and International Pub. No. WO2008100624. Exemplary HER3 antibodies also include the EGFR/HER3 bispecific antibody DL1 and any of the HER3 antibodies, whether monospecific or multi-specific, disclosed in U.S. Pat. Nos. 9,327,035 and 8,597,652, U.S. Pub. No. 20140193414, and International Pub. No. WO2010108127.

Exemplary HER3 antibodies also include the HER2/HER3 bispecific antibody MM-111 and any of the HER3 antibodies, whether monospecific or multi-specific, disclosed in U.S. Pub. Nos. 20130183311 and 20090246206 and International Pub. Nos. WO2006091209 and WO2005117973.

According to certain aspects, the HER3 targeting agent includes an anti-HER3 antibody that binds to an epitope of HER3 recognized by Patritumab from Daiichi Sankyo, Seribantumab (MM-121) from Merrimack Pharmaceuticals, Lumretuzumab from Roche, Elgemtumab from Novartis, GSK2849330 from GlaxoSmithKline, CDX-3379 of Celldex Therapeutics, EV20 and MP-RM-1 from MediPharma, Barecetamab (ISU104) from Isu Abxis Co., HMBD-001 (10D1F) from Hummingbird Bioscience Pte., REGN1400 from Regeneron Pharmaceuticals, and/or AV-203 from AVEO Oncology. According to certain aspects, the anti-HER3 antibody is selected from one or more of Patritumab, Seribantumab or an antibody including heavy chain sequence SEQ ID NO:108 and/or light chain sequence SEQ ID NO:109 which are reported for Seribantumab, Lumretuzumab or an antibody including heavy chain sequence SEQ ID NO:110 and/or light chain sequence SEQ ID NO:111 which are reported for Lumretuzumab, Elgemtumab or an antibody including heavy chain sequence SEQ ID NO:112 and/or light chain sequence SEQ ID NO:113 which are reported for Elgemtumab, AV-203, CDX-3379, GSK2849330, EV20, MP-RM-1, ISU104, HMBD-001 (10D1F), and REGN1400. Exemplary antibodies along with exemplary treatment indications are also described in Table 1.

TABLE 1

| Company Name (Originator) | Product Name | Targets | Therapeutic Modality | Exemplary Indications |
|---|---|---|---|---|
| Aveo Pharmaceuticals Inc. | CAN017, AV-203 | HER3 | Antibody | Esophageal cancer, solid tumors |
| Celldex Therapeutics Inc. | CDX-3379, ktn3379 | HER3 | Antibody | Head and neck cancer, solid tumors |
| Daiichi Sankyo Co. Ltd. | patritumab (AMG 888, U3-1287) | HER3 | Antibody | Non-small cell lung cancer (NSCLC), breast cancer, head and neck cancer |
| Daiichi Sankyo Co. Ltd. | U3-1402 | HER3 | Antibody-drug conjugate | NSCLC, breast cancer, colon cancer |
| GSK | GSK2849330 | HER3 | Antibody | Solid tumors |
| Hummingbird Bioscience Pte. Ltd. | HMBD-001 (10D1F) | HER3 | Antibody | Gastric cancer |
| Isu Abxis Co. Ltd. | ISU104 | HER3 | Antibody | Cancer (unspecified) |
| MediPharma | MP-RM-1 | HER3 | Antibody | Solid tumors |
| MediPharma | EV20 | HER3 | Antibody | Solid tumors |
| Merrimack Pharmaceuticals Inc. | Seribantumab (MM-121, SAR256212) | HER3 | Antibody | NSCLC, breast cancer, ovarian cancer |
| Novartis AG | elgemtumab (LJM716) | HER3 | Antibody | Esophageal cancer, Breast cancer, solid tumors |
| Regeneron Pharmaceuticals Inc. | REGN1400 | HER3 | Antibody | Cancer (unspecified) |
| Roche | Lumretuzumab (RG7116 or RO5479599) | HER3 | Antibody | Breast cancer, solid tumors |

It should be understood that wherever in this disclosure specific antibodies, specific antibody heavy chains and specific antibody light chains are disclosed, against HER3 or against any target, also intended to be disclosed for embodiment in or use in the various aspects of the invention are antibodies, such as but not limited to immunoglobulins, such as but not limited to IgG, that (i) include the heavy chain variable region of the disclosed antibody or heavy chain, (ii) include 1, 2 or 3 of the heavy chain CDRs (e.g., by Kabat definition) of the disclosed antibody or heavy chain, (iii) include the light chain variable region of the disclosed antibody or light chain, and/or (iv) include 1, 2 or 3 of the light chain CDRs (e.g., by Kabat definition) of the disclosed antibody or light chain. It should also be understood that wherever in this disclosure an antibody heavy chain or an antibody light chain is disclosed that includes an N-terminal leader sequence, also intended to be disclosed for embodiment in and use in the various aspects of the invention are corresponding heavy chains and corresponding light chains that lack the leader sequence.

Further, the invention provides modified versions of any of the recited amino acid sequences in which one or more isomeric amino acid replacements with exact mass, such as Leu for Ile or vice versa, are made (in, e.g., any of SEQ ID NOS:1-14 listed in FIGS. 1 and 2). Additionally, certain portions of these sequences may be substituted, such as by related portions from human immunoglobulins to form chimeric immunoglobulins (i.e., chimeric or humanized HER3). Exemplary substitutions include all or portions of the human leader sequence, and/or the conserved regions from human IgG1, IgG2, or IgG4 heavy chains and/or human Kappa light chain.

The sequence and structure of human HER3, human HER2, and human EGFR (HER1) are all known. An amino acid sequence of the human HER3 precursor protein (receptor tyrosine-protein kinase erbB-3 isoform 1 precursor NCBI Reference Sequence: NP_001973.2) is provided herein as SEQ ID NO:115. Those skilled in the art will readily appreciate that given known target protein amino acid sequences, various types of suitable antibodies and antibody mimetics specific for the extracellular domain of HER3, such as of human HER3, for use in the various aspects of the invention, may be produced using immunization and/or panning and/or antibody engineering techniques that are well established in the art.

A HER3 targeting agent that is radiolabeled for use in the various embodiments of the invention may, for example, include a HER3 binding peptide such as chelator-bearing HER3 binding peptide, such as a DOTA-bearing HER3 binding peptide, such as any of those disclosed in U.S. Pub. No. 20200121814.

According to certain aspects, the HER3 targeting agent includes/is a multi-specific targeting agent, such as a multi-specific antibody, against a first epitope of HER3 and at least a second epitope of HER3, or against HER3 and one or more different antigens such as one or more of EGFR (HER1), HER2, TROP2, and T-cell receptor gamma (TCRγ) chain alternate reading frame protein (TRAP). Exemplary multi-specific antibodies that may be used include bispecific antibodies against HER3/HER2 such as MM-111 from Merrimack Pharmaceuticals or MCLA-128 (i.e., Zenocutuzumab) from Merus N.V.; or against IGF-1R/HER3 such as MM-141 (i.e., Istiratumab) from Merrimack Pharmaceuticals; or against EGFR/HER3 such as MEHD7945A (i.e., Duligotumab) from Roche or any of the cetuximab-based bispecific or multi-specific zybodies from Zyngenia Inc.

According to certain aspects, a composition including a mixture of a HER3 targeting agent, such as an antibody against HER3, and one or more antibodies against one or more different antigens, in which one or more of the antibodies is radiolabeled, is provided and/or used. An exemplary antibody composition including an antibody mixture includes at least Sym013 from Symphogen having six monoclonal antibodies against EGFR (HER1), HER2, and HER3. In one aspect of the invention, one or more of the antibodies, such as an anti-HER3 antibody, of Sym013 may be radiolabeled. A related aspect of the invention provides a composition including targeting agents against EGFR (HER1), HER2, ad HER3, such as antibodies, in which one or more in any combination or all are radiolabeled The present invention further provides multi-specific targeting agents, compositions and related methods of treating a proliferative disease or disorder which include administration of (i) a multi-specific antibody against two or more epitopes of HER3, or against an epitope of HER3 and an epitope of one or more additional different antigens, and/or (ii) administration of a HER3 targeting agent such as an antibody and one or more discrete targeting agents directed against one or more cancer associated antigens wherein one or more of the targeting agents, such as the HER3 targeting agent is radiolabeled. The additional different antigens may, for example, be antigens whose expression is upregulated on cells involved in various diseases or disorders, such as proliferative disorders, for example, solid tumor cancers, such as those in which HER3 is also or can also be upregulated. For example, the additional different antigens may be selected from the group including mesothelin, TSHR, CD19, CD123, CD22, CD30, CD45, CD171, CD138, CS-1, CLL-1, GD2, GD3, B-cell maturation antigen (BCMA), Tn Ag, prostate specific membrane antigen (PSMA), ROR1, FLT3, TROP2, T-cell receptor gamma (TCRγ) chain alternate reading frame protein (TRAP), fibroblast activation protein (FAP), calreticulin, phosphatidylserine, GRP78 (BiP), TAG72, CD38, CD44v6, CEA, EPCAM, B7H3, KIT, IL-13Ra2, interleukin-11 receptor a (IL-11Ra), PSCA, PRSS21, VEGFR2, LewisY, CD24, platelet-derived growth factor receptor-beta (PDGFR-beta), SSEA-4, CD20, Folate receptor alpha (FRa), ERBB2 (Her2/neu), MUC1, epidermal growth factor receptor (EGFR), EGFRvIII, NCAM, Prostase, PAP, ELF2M, Ephrin B2, IGF-I receptor, CAIX, LMP2, gplOO, bcr-abl, tyrosinase, EphA2, Fucosyl GM1, sLe, GM3, DR5, 5T4, TGS5, HMWMAA, o-acetyl-GD2, Folate receptor beta, TEM1/CD248, TEM7R, CLDN6, GPRC5D, CXORF61, CD97, CD 179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, MAGEA3, MAGEA3/A6, ETV6-AML, sperm protein 17, XAGE1, Tie 2, MAD-CT-1, MAD-CT-2, Fos-related antigen 1, prostein, survivin and telomerase, PCTA-1/Galectin 8, KRAS, MelanA/MART1, Ras mutant, hTERT, sarcoma translocation breakpoints, ML-IAP, ERG (TMPRSS2 ETS fusion gene), NA17, PAX3, Androgen receptor, Cyclin B 1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, GPA7, and IGLL1.

Exemplary DR5 (death receptor 5) targeting agents that may be radiolabeled, unlabeled or drug-conjugated for use in the invention include the monoclonal anti-DR5 antibodies mapatumumab, conatumumab, lexatumumab, tigatuzumab, drozitumab, and LBY-135. Such DR5 targeting agents may, for example, be used in combination with a radiolabeled HER3 targeting agents for the treatment of ovarian, breast, cervical prostate, gastric, bladder, lung, melanoma, colorectal and squamous cell carcinoma cancers and any of the cancers disclosed herein.

Exemplary 5T4 (Trophoblast glycoprotein (TBPG)) targeting agents that may be radiolabeled, drug-conjugated, or unlabeled for use in the invention include the anti-5T4 monoclonal antibodies MED10641, ALG.APV-527, Tb535, H6-DM5, and ZV0508, as well as Naptumomab estafenatox or the Fab portion thereof. Such 5T4 targeting agents may, for example, be used in combination with a radiolabeled HER3 targeting agent for the treatment of ovarian, head and neck, breast, prostate, gastric, bladder, lung, melanoma, colorectal and squamous cell carcinoma cancers and any of the cancers disclosed herein.

Exemplary HER2 (ERBB2) targeting agents that may be radiolabeled, drug-conjugated, or unlabeled for use in the invention include the monoclonal antibodies trastuzumab and pertuzumab. Applicants have successfully conjugated Trastuzumab with p-SCN-DOTA and radiolabeled the composition with $^{225}$Ac or $^{177}$Lu. Exemplary ADCs targeting HER2 that may be used include fam-trastuzumab deruxtecan-nxki (Enhertu®; AstraZeneca/Daiichi Sankyo) and Trastuzumab emtansine (Roche/Genentech). The anti-HER2 antibody may, for example, also be a multi-specific antibody, such as bispecific antibody, against any available epitope of HER3/HER2 such as MM-111 and MM-141/Istiratumab from Merrimack Pharmaceuticals, MCLA-128 from Merus NV, and MEHD7945A/Duligotumab from Genentech. HER2 targeting agents may, for example, be used in combination with a radiolabeled HER3 targeting agent in the treatment of HER2-expressing cancers such as ovarian, breast, metastatic breast, esophageal, lung, cervical, and endometrial cancers including but not limited to those that are both HER2- and HER3-positive.

The amino acid sequences of the heavy chain and the light chain of Trastuzumab reported by DrugBank Online are: heavy chain (SEQ ID NO:102) and light chain (SEQ ID NO:103) and a HER2 binding antibody including one or both of said chains may be embodied in or used in the various embodiments of the invention.

The amino acid sequences of the heavy chain and the light chain of Pertuzumab reported by DrugBank Online are: heavy chain (SEQ ID NO:104) and light chain (SEQ ID NO:105) and a HER2 binding antibody including one or both of said chains may be embodied in or used in the various embodiments of the invention.

Exemplary CD33 targeting agents that may be radiolabeled, drug-conjugated, or unlabeled for use in the invention include the monoclonal antibodies lintuzumab, gemtuzumab, and vadastuximab. In combination with a radiolabeled HER3 targeting agent as disclosed herein, a CD33 targeting therapeutic agent may, for example, be used to treat solid cancers, such as ovarian, breast, cervical prostate, gastric, bladder, lung, melanoma, colorectal and squamous cell carcinoma cancers and any of the cancers disclosed herein, for example, by depleting myeloid-derived suppressor cells (MDSCs). In one aspect, the CD33 targeting agent used in combination with a radiolabeled HER3 targeting agent is 225Ac-lintuzumab. In another aspect, the CD33 targeting agent used in combination with a radiolabeled HER3 targeting agent is the ADC gemtuzumab ozogamicin (Mylotarg®; Pfizer).

Exemplary CD38 targeting agents that may be radiolabeled, drug-conjugated, or unlabeled for use in the invention include anti-CD38 monoclonal antibodies such as daratumumab (Darzalex®; Johnson and Johnson) and isatuximab (Sarclisa®; Sanofi) or antigen-binding fragments thereof. Such CD38 targeting agents may, for example, be used in combination with the radiolabeled HER3 targeting agents in the treatment of solid tumors that may, for example, be infiltrated with CD38-positive suppressive immune cells, such as but not limited to ovarian, breast, cervical prostate, gastric, bladder, lung, melanoma, colorectal and squamous cell carcinoma cancers and any of the cancers disclosed herein.

Exemplary different antigens (over HER3) that may be targeted by a multi-specific antibody according to aspects of the present invention include at least HER1 (EGFR), HER2, and IGF-1R. Exemplary HER3 multi-specific targeting agents include multi-specific antibodies such as MM-111 from Merrimack Pharmaceuticals or MCLA-128 (i.e., Zenocutuzumab) from Merus N.V.; or against IGF-1R/HER3 such as MM-141 (i.e., Istiratumab) from Merrimack Pharmaceuticals; or against EGFR/HER3 such as MEHD7945A (i.e., Duligotumab) from Roche, the cetuximab-based bispecific zybody from Zyngenia Inc., and the multi-specific antibody composition Sym-013 from Symphogen. See also Table 2 for further description and exemplary indications.

component may be derived from a different epitope of the HER3 antigen or may be derived from any of the antigens listed above.

A HER3 targeting agent may include a radioisotope, and any additional antibodies against other antigens may optionally include a radioisotope. According to certain aspects of the present invention, when the immunotherapy includes a bispecific antibody, either one or both of the first target recognition component and the second target recognition component, or any part of the bispecific targeting agent, may include a radioisotope.

TABLE 2

| Company Name (Originator) | Product Name | Targets | Therapeutic Modality | Exemplary Indications |
|---|---|---|---|---|
| Merrimack Pharmaceuticals Inc. | Istiratumab (MM-141) | IGF-1R; HER3 | Bispecific Antibody | Solid tumors |
| Merrimack Pharmaceuticals Inc. | MM-111 | HER2; HER3 | Bispecific Antibody | Breast cancer, solid tumors |
| Merus N.V. | MCLA-128 | HER2; HER3 | Bispecific Antibody | NSCLC, breast cancer, ovarian cancer, colorectal cancer, gastric cancer, endometrial cancer, solid tumors |
| Roche | Duligotuzmab (MEHD7945A, RG7597) | EGFR; HER3 | Antibody | Colorectal cancer, epithelial cancer, head and neck cancer, solid tumors |
| Symphogen | Sym013 | HER1, HER2, HER3 | Antibody (mixture) | Solid tumors |
| Zyngenia Inc. | Cetuximab-based bispecific zybody | EGFR; HER3 | Antibody | Cancer (unspecified) |

The present invention also provides methods of treating a proliferative disease or disorder that includes administration of a first antibody against at least one epitope of HER3, and administration of a second antibody, wherein the second antibody is against a different epitope of HER3 than the first antibody, or is against an epitope of a different antigen, such as one or more antigens selected from the list of different antigens presented above. One or more of the HER3 antibodies may be radiolabeled. Antibodies against the different antigens may, for example, also be radiolabeled in any combination.

Such combinations, presented as a multi-specific antibody or more than one monoclonal antibody as indicated above, may deliver a synergistic therapeutic effect comparable to the effectiveness of a monotherapy with only an antibody against HER3, while reducing adverse side effects of the monotherapy. Moreover, the combination may deliver an improved effectiveness over the monotherapy, which may, for example, be measured by reduction in the total tumor cell number, increase in the length of time to relapse, and other indicia of patient health.

When the methods include administration of a multi-specific antibody, the first target recognition component may, for example, include one of: a first full-length heavy chain and a first full-length light chain, a first Fab fragment, a first single-chain variable fragment (scFvs), or other type of antibody. The second target recognition component may, for example, include one of: a second full length heavy chain and a second full length light chain, a second Fab fragment, or a second single-chain variable fragment (scFvs) or other type of antibody. Moreover, the second target recognition According to certain aspects of the present invention, the radiolabeled targeting agent may exhibit essentially the same immunoreactivity to the antigen as a control targeting agent, wherein the control targeting agent includes the naked targeting agent or otherwise unlabeled targeting agent against the same epitope of the antigen (i.e., HER3) as the radiolabeled targeting agent.

According to certain aspects of the present invention, the targeting agent may be labeled with $^{225}$Ac, and may be at least 5-fold more effective at causing cell death of HER3-positive cells than a control monoclonal antibody, wherein the control monoclonal antibody includes a naked or unlabeled antibody against the same epitope of the antigen as the $^{225}$Ac labeled antibody. For example, a $^{225}$Ac labeled monoclonal antibody may be at least 10-fold more effective, at least 20-fold more effective, at least 50-fold more effective, or at least 100-fold more effective at causing cell death of HER3-positive cells than the control monoclonal antibody.

According to certain aspects of the present invention, the methods may include administration of labeled and unlabeled (e.g., "naked") fractions of the HER3 targeting agent, such as an antibody, antibody fragment, etc. For example, the un-labeled fraction may include the same antibody against the same epitope as the labeled fraction. In this way, the total radioactivity of the antibody may be varied or may be held constant while the overall antibody protein concentration may be held constant or may be varied, respectively. For example, the total protein concentration of un-labeled antibody fraction administered may vary depending on the exact nature of the disease to be treated, age and weight of the patient, identity of the monoclonal antibody, and the label (e.g., radionuclide) selected for labeling of the monoclonal antibody.

According to certain aspects of the present invention, the effective amount of the anti-HER3 antibody is a maximum tolerated dose (MTD) of the anti-HER3 antibody.

According to certain method aspects of the present invention, when more than one antibody is administered, the antibodies may be administered at the same time. As such, according to certain aspects of the present invention, the antibodies may be provided in a single composition. Alternatively, the two antibodies may be administered sequentially. As such, the radiolabeled HER3 targeting agent may be administered before the second antibody, after the second antibody, or both before and after the second antibody. Moreover, the second antibody may be administered before the radiolabeled HER3 targeting agent, after the radiolabeled HER3 targeting agent, or both before and after the radiolabeled HER3 targeting agent.

According to certain aspects of the methods of the present invention, a radiolabeled HER3 targeting agent may be administered according to a dosing schedule selected from the group consisting of one every 7, 10, 12, 14, 20, 24, 28, 35, and 42 days throughout a treatment period, wherein the treatment period includes at least two doses.

According to certain aspects of the present invention, the radiolabeled HER3 targeting agent may be administered according to a dose schedule that includes 2 doses, such as on days 1 and 5, 6, 7, 8, 9, or 10 of a treatment period, or days 1 and 8 of a treatment period.

Administration of the radiolabeled HER3 targeting agents of the present invention, in addition to other therapeutic agents, may be provided in a number of ways depending upon whether local or systemic treatment is desired and upon the area to be treated. Administration may be intratracheal, intranasal, epidermal and transdermal, oral or parenteral. Parenteral administration includes intravenous, intraarterial, subcutaneous, intraperitoneal or intramuscular injection or infusion; or intracranial, e.g., intrathecal or intraventricular, administration. In some embodiments a slow-release preparation including the targeting agents(s) and/or other therapeutic agents may be administered. The various agents may be administered as a single treatment or in a series of treatments that continue as needed and for a duration of time that causes one or more symptoms of the cancer to be reduced or ameliorated, or that achieves another desired effect.

The dose(s) may vary, for example, depending upon the identity, size, and condition of the subject, further depending upon the route by which the composition is to be administered and the desired effect. Appropriate doses of a therapeutic agent depend upon the potency with respect to the expression or activity to be modulated. The therapeutic agents can be administered to an animal (e.g., a human) at a relatively low dose at first, with the dose subsequently increased until an appropriate response is obtained.

The radiolabeled HER3 targeting agent may be administered simultaneously or sequentially with the one or more additional therapeutic agents. Moreover, when more than one additional therapeutic agent is included, the additional therapeutic agents may be administered simultaneously or sequentially with each other and/or with the radiolabeled HER3 targeting agent.

Radiolabeling the HER3 Targeting Agent

The HER3 targeting agent and other targeting agents disclosed herein may, for example, be labeled with a radioisotope, such as a beta emitter (e.g. $^{177}$Lu) or an alpha emitter (e.g., $^{225}$Ac), through conjugation of a chelator molecule, and chelation of the radioisotope thereto. According to certain aspects, the targeting agent may be an antibody against that is deglycosylated in the constant region, such as at asparagine-297 (Asn-297, N297; Kabat number) in the heavy chain CH2 domain, for the purpose of uncovering a unique conjugation site, glutamine (i.e., Gln-295, Q295) so that it is available for conjugation with bifunctional chelator molecules.

According to certain aspects, the radiotherapeutic may be an antibody that may have reduced disulfide bonds such as by using reducing agents, which may then be converted to dehydroalanine for the purpose of conjugating with a bifunctional chelator molecule.

According to certain aspects, the radiotherapeutic may be an antibody for which the disulfide bonds have been reduced using reducing agents, which is then conjugated via aryl bridges with a bifunctional chelator molecule. For example, according to certain aspects a linker molecule such as 3,5-bis(bromomethyl)benzene may be used to bridge the free sulfhydryl groups on the antibody.

According to certain aspects, the radiotherapeutic may be an antibody that may have certain specific existing amino acids replaced with cysteine(s) that then can be used for site-specific labeling.

Exemplary chelators that may be linked to targeting agents in the various aspects of the invention include: 1,4,7,10-tetraazacyclododecane-1,4,7-triacetic acid (DO3A) or a derivative thereof; 1,4,7-triazacyclononane-1,4-diacetic acid (NODA) or a derivative thereof; 1,4,7-triazacyclononane-1,4,7-triacetic acid (NOTA) or a derivative thereof; 1,4,7,10-tetraazacyclododecane-1,4,7,10-tetraacetic acid (DOTA) or a derivative thereof; 1,4,7-triazacyclononane, 1-glutaric acid-4,7-diacetic acid (NODAGA) or a derivative thereof; 1,4,7,10-tetraazacyclodecane, 1-glutaric acid-4,7,10-triacetic acid (DOTAGA) or a derivative thereof; 1,4,8,11-tetraazacyclotetradecane-1,4,8,11-tetraacetic acid (TETA) or a derivative thereof; 1,4,8,11-tetraazabicyclo[6.6.2]hexadecane-4,11-diacetic acid (CB-TE2A) or a derivative thereof; diethylene triamine pentaacetic acid (DTPA), its diester, or a derivative thereof; 2-cyclohexyl diethylene triamine pentaacetic acid (CHX-A"-DTPA) or a derivative thereof; deforoxamine (DFO) or a derivative thereof; 1,2-[[6-carboxypyridin-2-yl]methylamino]ethane ($H_2$dedpa) or a derivative thereof; DADA or a derivative thereof; 1,4,7,10-Tetraazacyclododecane-1,4,7,10-tetra(methylene phosphonic acid) (DOTP) or a derivative thereof; 4-amino-6-[[16-[(6-carboxypyridin-2-yl)methyl]-1,4,10,13-tetraoxa-7,16-diazacyclooctadec-7-yl]methyl]pyridine-2-carboxylic acid (MACROPA-NH2) or a derivative thereof; MACROPA or a derivative thereof; 1,4,7,10-tetrakis(carbamoylmethyl)-1,4,7,10-tetraazacyclododecane (TCMC) or a derivative thereof; {4-[2-(bis-carboxymethyl-amino)-ethyl]-7-carboxymethyl-[1,4,7]triazonan-1-yl}-acetic acid (NETA) or a derivative thereof; Diamsar or a derivative thereof; 1,4,7-triazacyclononane-1,4,7-tris[methyl(2-carboxyethyl)phosphinic acid (TRAP, PRP9, TRAP-Pr) or a derivative thereof; N,N'-bis(6-carboxy-2-pyridylmethyl)ethylenediamine-N,N'-diacetic acid (H4octapa) or a derivative thereof; N,N'-[1-benzyl-1,2,3-triazole-4-yl]methyl-N,N'-[6-(carboxy)pyridin-2-yl]-1,2-diaminoethane (H2azapa) or a derivative thereof; N,N"-[[6-(carboxy)pyridin-2-yl]methyl]diethylenetriamine-N,N',N"-triacetic acid (H5decapa) or a derivative thereof; N,N'-bis(2-hydroxy-5-sulfobenzyl)ethylenediamine-N,N'-diacetic acid (SHBED) or a derivative thereof; N,N'-bis(2-hydroxybenzyl)ethylenediamine-N,N'-diacetic acid (HBED) or a derivative thereof; 3,6,9,15-tetraazabicyclo[9.3.1]pentadeca-1(15),11,13-triene-3,6,9, -triacetic acid (PCTA) or a derivative thereof; desferrioxamine B (DFO) or a derivative thereof; N,N'-(methylenephosphonate)-N,N'-[6-(methoxycarbonyl)pyridin-2-yl]methyl-1,2-diaminoethane (H6phospa) or a derivative thereof; 1,4,7,10,13,16-hexaazacyclohexadecane-N,N,N",N"',N"",N"'"-hexaacetic acid (HEHA) or a derivative thereof; 1,4,7,10,13-pentaazacyclopentadecane-N,N',N",N"',N""-pentaacetic acid (PEPA) or a derivative thereof; or 3,4,3-LI(1,2-HOPO) or a derivative thereof.

According to certain aspects, the targeting agent may be radiolabeled through chemical conjugation of suitable bifunctional chelators that can chelate one or more radionuclides. Exemplary chelator molecules that may be used include p-SCN-Bn-DOTA, $NH_2$-DOTA, $NH_2$—$(CH_2)_{1-20}$-DOTA, $NH_2$-$(PEG)_{1-20}$-DOTA, HS-DOTA, HS—$(CH_2)_{1-20}$-DOTA, HS-$(PEG)_{1-20}$-DOTA, dibromo-S—$(CH_2)_{1-20}$-DOTA, dibromo-S-$(PEG)_{1-20}$-DOTA, p-SCN-Bn-DOTP, $NH_2$-DOTP, $NH_2$—$(CH_2)_{1-20}$-DOTP, $NH_2$-$(PEG)_{1-20}$-DOTP, HS-DOTP, HS—$(CH_2)_{1-20}$-DOTP, HS-$(PEG)_{1-20}$-DOTP, dibromo-S—$(CH_2)_{1-20}$-DOTP, and dibromo-S-$(PEG)_{1-20}$-DOTP.

The chelator molecules may, for example, be attached to a targeting agent through a linker molecule. Exemplary linker molecules include:

—$CH_2(C_6H_4)NH_2$ or —$CH_2(C_6H_4)NH$—X—Y, wherein X is

—$R_2$—$CH_2CH_2O(CH_2CH_2O)_nCH_2CH_2$—,

—$R_2$—$CH_2CH_2NHC(O)CH_2CH_2O(CH_2CH_2O)_nCH_2CH_2$—,

—$R_2$—$(CH_2)_nCH_2$—,

—$R_2$—$CH_2CH_2NHC(O)(CH_2)_nCH_2$—,

—$R_2$—$CH(C(O)R_3)CH_2$—, wherein $R_3$ is —OH or a short peptide (1-20 amino acids), —$R_2$—$CH_2CH_2O(CH_2CH_2O)_nCH_2C(O)O$—, or —$R_2$—$CH_2CH_2NHC(O)CH_2CH_2O(CH_2CH_2O)_nCH_2CC(O)O$—, wherein n is 1-20, and $R_2$ is —C(O)— or —C(S)NH—; and Y is —$NH_2$ or —$SR_4$—, wherein $R_4$ is —H or —$CH_2$-3,5-bis(bromomethyl)benzene.

Targeting agents, such as protein targeting agents, for example antibodies and antigen-binding antibody fragments, and peptide targeting agents may, for example, be conjugated with a chelator for radiolabeling the targeting agent via chelation of a radionuclide. Such protein or peptide targeting agents, for example, that include lysine(s), may conveniently be conjugated to a DOTA chelating moiety using the bifunctional agent S-2-(4-Isothiocyanatobenzyl)-1,4,7,10-tetraazacyclododecane tetraacetic acid a/k/a/ "p-SCN-Bn-DOTA" (Catalog #B205; Macrocyclics, Inc., Plano, TX, USA). p-SCN-Bn-DOTA may be synthesized by a multi-step organic synthesis fully described in U.S. Pat. No. 4,923,985. Chelation of a radionuclide by the DOTA moiety may be performed prior to chemical conjugation of the antibody with p-SCN-Bn-DOTA and/or after said conjugation.

Methods for labeling a chelator-conjugated targeting agent with an exemplary radionuclide are described in in Example 1.

Diagnostic Aspects

The presently disclosed methods may include diagnosing the subject to ascertain if HER3-positive cells are present, to what extent they are, and/or their localization. HER3-positive cells may be present in a number of biological specimens, such as in circulating cells in a sample of blood from the subject or tumor cells in a biopsy of the subject. In one aspect, the diagnosing step may generally include obtaining a sample of blood or tissue from the subject and mounting the sample on a substrate. The presence or absence of the HER3 antigen may be detected using a diagnostic antibody, peptide, or small molecule, wherein the diagnostic antibody peptide, or small molecule is labeled with any of the standard imaging labels known in the art. Exemplary labeling agents include, for example, radiolabels such as $^{3}H$, $^{14}C$, $^{32}P$, $^{35}S$, and $^{125}I$; fluorescent or chemiluminescent compounds, such as fluorescein isothiocyanate, rhodamine, or luciferin; and enzymes, such as alkaline phosphatase, β-galactosidase, or horseradish peroxidase. An exemplary HER3 targeting agent used in such a diagnostic assay includes a human or humanized antibody against HER3.

In another aspect, the methods may include diagnosing the subject to ascertain if HER3-positive cells are present using a HER3 targeting agent labeled with a radionuclide such as any of $^{18}F$, $^{11}C$, $^{68}Ga$, $^{64}Cu$, $^{89}Zr$, or $^{124}I$, for PET imaging, or $^{99m}Tc$ or $^{111}In$, for SPECT imaging. Accordingly, the method may include administering to the subject a HER3 targeting agent labeled with one or more of $^{18}F$, $^{11}C$, $^{68}Ga$, $^{64}Cu$, $^{89}Zr$, $^{124}I$, $^{99m}Tc$, or $^{111}In$, and performing a non-invasive imaging technique on the subject, such as performing a PET or SPECT scan on the subject. The method may include administering the radiolabeled HER3 targeting agent for imaging to the subject and, after an amount of time sufficient for the targeting agent to bind to target in the subject's tissues, performing the imaging. The amount of time sufficient for the targeting agent to bind to target in the subject's tissues may, for example, be at least 20 minutes, at least 30 minutes, at least 60 minutes, or any number or subrange of minutes in the range 20 minutes to 360 minutes. According to certain one aspect of the method, the radiolabeled HER3 targeting agent may include $^{68}Ga$, $^{89}Zr$, or $^{111}In$, and may be labeled using any of the methods disclosed herein (e.g., such as disclosed in Example 1).

If the subject has HER3-positive cancer cells, for example, beyond a predetermined or preselected threshold level, or other indications of a HER3-positive cancer/tumor, the therapeutic methods of the presently disclosed invention may be carried out, i.e., administration of a therapeutically effective amount of a radiolabeled HER3 targeting agent, alone or in combination with one or more additional therapeutic agents may be performed.

Additional Therapeutic Agents and Modalities

The methods of the present invention that include administration of a radiolabeled HER3 targeting agent therapeutic, alone or in combination with other targeting agents, may further include administration of an additional therapeutic agent or modality. According to certain aspects, the additional agent may be relevant for the disease or condition being treated by the radiolabeled HER3 targeting agent. Such administration may be simultaneous, separate or sequential with the administration of the effective amount of the HER3 targeting agent. For simultaneous administration, the agents may be administered as one composition, or as separate compositions, as appropriate.

Exemplary additional therapeutic agents and modalities that may be used in combination or conjunction with a radiolabeled HER3 targeting agent include at least chemotherapeutic agents, small molecule oncology drugs, anti-inflammatory agents, immunosuppressive agents, immunomodulatory agents, include immune checkpoint therapies, DDR inhibitors, CD47 blockades, external beam radiation, brachytherapy, or any combination thereof. Exemplary additional agents and treatment modalities that may be used in combination or conjunction with a radiolabeled HER3 targeting agent alone or in combination other targeting agents as disclosed herein are further described below.

A. Chemotherapeutic and Other Small Molecule Agents

Exemplary chemotherapeutic agents include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolomide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguamne, azathioprine, T-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as oxaliplatin, cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o, p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Therapies targeting epigenetic mechanisms including, but not limited to: (i) histone deacetylase (HDAC) inhibitors such as Vorinostat (suberoylanilide hydroxamic acid; SAHA), Romidepsin, Belinostat (PDX101), Panobinostat (LBH589) and Tucidinostat, demethylating agents (e.g., Vidaza); (ii) LSD1 inhibitors such as seclidemstat, TCP (tranylcypromine), ORY-1001 (iadademstat), GSK2879552 (GSK), INCB059872 (Imago BioSciences), IMG-7289 (Bomedemstat; Imago BioSciences), ORY-2001 (Vafidemstat), and CC-90011 (Celgene); and (iii) release of transcriptional repression (ATRA) therapies, may also be used in combination or conjunction with a radiolabeled HER3 targeting agent and/or other radiolabeled targeting agents and combinations thereof as disclosed herein.

According to certain aspects of the present invention, the chemotherapeutic agents include at least radiosensitizers, such as temozolomide, cisplatin, and/or fluorouracil.

The additional agents may, for example, include a bcl-2 inhibitor such as navitoclax or venetoclax (Venclexta®; Abbvie) and the combination may, for example, be used for the treatment of solid tumors such as breast cancers and lunger cancer such as small cell lung carcinoma (SCLC).

The additional agents may, for example, include a cyclin-dependent kinase CDK4 and CDK6 inhibitor such as palbociclib (Ibrance®; Pfizer) and the combination may, for example, be used for the treatment of solid cancers such as breast cancers such as HR-positive and HER2-negative breast cancer, with or without an aromatase inhibitor.

The additional agents may, for example, include erlotinib (Tarceva®; Roche) and the combination may, for example, be used for the treatment of solid tumor cancers such as non-small cell lung cancer (NSCLC), for example, with mutations in the epidermal growth factor receptor (EGFR) and pancreatic cancer.

The additional agents may, for example, include sirolimus or everolimus (Affinitor®; Novartis) and the combination may, for example, be used for the treatment of solid tumor cancers such as melanoma and breast cancer.

The additional agents may, for example, include pemetrexed (Alimta®; Eli Lilly) and the combination may, for example, be used for the treatment of solid cancers such as mesothelioma such as pleural mesothelioma and lung cancer such as non-small cell lung cancer (NSCLC).

The additional therapeutic agents may, for example, be administered according to any standard dose regime known in the field. For example, therapeutic agents may be administered at concentrations in the range of 1 to 500 mg/m$^2$, the amounts being calculated as a function of patient surface area (m$^2$). For example, exemplary doses of the chemotherapeutic paclitaxel may include 15 mg/m$^2$ to 275 mg/m$^2$, exemplary doses of docetaxel may include 60 mg/m$^2$ to 100 mg/m$^2$, exemplary doses of epithilone may include 10 mg/m$^2$ to 20 mg/m$^2$, and an exemplary dose of calicheamicin may include 1 mg/m$^2$ to 10 mg/m$^2$. While exemplary doses are listed herein, such are only provided for reference and are not intended to limit the dose ranges of the drug agents of the presently disclosed invention.

B. External Beam Radiation and/or Brachytherapy

The additional therapeutic modality administered in conjunction with the HER3 targeting agent, and optionally any other of the additional therapeutics disclosed herein, may be an ionizing radiation, such as administered via external beam radiation or brachytherapy. Such radiation generally refers to the use of X-rays, gamma rays, or charged particles (e.g., protons or electrons) to generate ionizing radiation, such as delivered by a machine placed outside the patient's body (external-beam radiation therapy) or by a source placed inside a patient's body (internal radiation therapy or brachytherapy).

The external beam radiation or brachytherapy may enhance the targeted radiation damage delivered by the radiolabeled HER3 targeting agent and may thus be delivered sequentially with the HER3 targeting agent, such as before and/or after the HER3 targeting agent, or simultaneous with the HER3 targeting agents.

The external beam radiation or brachytherapy may be planned and administered in conjunction with imaging-based techniques such as computed tomography (CT) and/or magnetic resonance imaging (MM) to accurately determine the dose and location of radiation to be administered. For example, a patient treated with any of the radiolabeled HER3 targeting agents disclosed herein may be imaged using either of CT or Mill to determine the dose and location of radiation to be administered by the external beam radiation or brachytherapy.

In various embodiments, the radiation therapy may be selected from the group consisting of total all-body radiation therapy, conventional external beam radiation therapy, stereotactic radiosurgery, stereotactic body radiation therapy, 3-D conformal radiation therapy, intensity-modulated radiation therapy, image-guided radiation therapy, tomotherapy, and brachytherapy. According to certain aspects, the radiation therapy may be provided as a single dose or as fractionated doses, e.g., as 2 or more fractions. For example, the dose may be administered such that each fraction includes 2-20 Gy (e.g., a radiation dose of 50 Gy may be split up into 10 fractions, each including 5 Gy). The 2 or more fractions may be administered on consecutive or sequential days, such as once in 2 days, once in 3 days, once in 4 days, once in 5 days, once in 6 days, once in 7 days, or in a combination thereof.

C. Immune Checkpoint Therapies

The additional agent(s) administered in conjunction with the HER3 targeting agent may be an immune checkpoint therapy. Cancer cells have developed means to evade the standard checkpoints of the immune system. For example, cancer cells have been found to evade immunosurveillance through reduced expression of tumor antigens, downregulation of MHC class I and II molecules leading to reduced tumor antigen presentation, secretion of immunosuppressive cytokines such as TGFb, recruitment or induction of immunosuppressive cells such as regulatory T cells (Treg) or myeloid-derived suppressor cells (MDSC), and overexpression of certain ligands [e.g., programmed death ligand-1 (PD-L1)] that inhibit the host's existing antitumor immunity.

Another major mechanism of immune suppression by cancer cells is a process known as "T-cell exhaustion", which results from chronic exposure to tumor antigens, and is characterized by the upregulation of inhibitory receptors. These inhibitory receptors serve as immune checkpoints in order to prevent uncontrolled immune reactions.

Various immune checkpoints acting at different levels of T cell immunity have been described in the literature, including PD-1 (i.e., programmed cell death protein 1) and its ligands PD-L1 and PD-L2, CTLA-4 (i.e., cytotoxic T-lymphocyte associated protein-4) and its ligands CD80 and CD86, LAG3 (i.e., Lymphocyte-activation gene 3), B and T lymphocyte attenuator, TIGIT (T-cell immunoreceptor with Ig and ITIM domains), TIM-3 (i.e., T-cell immunoglobulin and mucin-domain containing protein 3), and VISTA (V-domain immunoglobulin suppressor of T cell activation).

Enhancing the efficacy of the immune system by therapeutic intervention is a particularly exciting development in cancer treatment. As indicated, checkpoint inhibitors such as CTLA-4 and PD-1 prevent autoimmunity and generally protect tissues from immune collateral damage. In addition, stimulatory checkpoints, such as OX40 (i.e., tumor necrosis factor receptor superfamily, member 4; TNFR-SF4), CD137 (i.e., TNFR-SF9), GITR (i.e., Glucocorticoid-Induced TNFR), CD27 (i.e., TNFR-SF7), CD40 (i.e., cluster of differentiation 40), and CD28, activate and/or promote the expansion of T-cells. Regulation of the immune system by inhibition or overexpression of these proteins is an area of promising current research.

Thus, a promising therapeutic strategy is the use of immune checkpoint therapies that may remove certain blockades on the immune system that are utilized by cancer cells, in combination with the HER3 targeting agents disclosed herein. For example, antibodies against certain immune checkpoint inhibitors (ICI) may block interaction between checkpoint inhibitor proteins and their ligands, therefore preventing the signaling events that would otherwise have led to inhibition of an immune response against the tumor cell.

Moreover, there is a growing body of preclinical evidence supporting the ability of radiation to synergize with ICI antibodies, and this is also being explored in the clinic with increasing numbers of clinical trials evaluating the combination of external beam radiation with immune checkpoint therapies across various tumor types and ICI antibodies (Lamichhane, 2018). Clinical evidence supporting this combination has been generated in melanoma, with two studies demonstrating a clinical benefit using radiation in combination with the anti-cytotoxic T-lymphocyte-associated protein 4 (CTLA-4) ICI antibody, Ipilimumab (Twyman-Saint Vistor, 2015).

Accordingly, an object of the presently disclosed invention is to provide therapies for the treatment of cancer using a HER3 targeting agent in combination with one or more immune checkpoint therapies, such as an ICI antibody.

Immune checkpoint therapies of the present invention include molecules that totally or partially reduce, inhibit, interfere with or modulate one or more checkpoint proteins. Checkpoint proteins regulate T-cell activation or function. Immune checkpoint therapies may unblock an existing immune response inhibition by binding to or otherwise disabling checkpoint inhibition. The immune checkpoint therapies may include monoclonal antibodies, humanized antibodies, fully human antibodies, antibody fragments, small molecule therapeutics, or a combination thereof.

Exemplary immune checkpoint therapies may specifically bind to and inhibit a checkpoint protein, such as the inhibitory receptors CTLA-4, PD-1, TIM-3, VISTA, BTLA, LAG-3 and TIGIT, and/or the activating receptors CD28, OX40, CD40, GITR, CD137, CD27, and HVEM. Additionally, the immune checkpoint therapy may bind to a ligand of any of the aforementioned checkpoint proteins, such as PD-L1, PD-L2, PD-L3, and PD-L4 (ligands for PD-1); CD80 and CD86 (ligands for CTLA-4); CD137-L (ligand of CD137); and GITR-L (ligand of GITR). Other exemplary immune checkpoint therapies may bind to checkpoint proteins such as CD226, B7-H3, B7-H4, BTLA, TIGIT, GALS, KIR, 2B4 (belongs to the CD2 family of molecules and is expressed on all NK, γδ, and memory CD8+ (αβ) T cells), CD160 (also referred to as BY55), and CGEN-15049.

Central to the immune checkpoint process are the CD137, CTLA-4 and PD-1 immune checkpoint pathways.

The CTLA-4 and PD-1 pathways are thought to operate at different stages of an immune response. CTLA-4 is considered the "leader" of the immune checkpoint inhibitors (ICI), as it stops potentially autoreactive T cells at the initial stage of naive T-cell activation, typically in lymph nodes. The PD-1 pathway regulates previously activated T cells at the later stages of an immune response, primarily in peripheral tissues. Moreover, progressing cancer patients have been shown to lack upregulation of PD-L1 by either tumor cells or tumor-infiltrating immune cells. Immune checkpoint therapies targeting the PD-1 pathway might thus be especially effective in tumors where this immune suppressive axis is operational and reversing the balance towards an immune protective environment would rekindle and strengthen a pre-existing anti-tumor immune response. PD-1 blockade can be accomplished by a variety of mechanisms including antibodies that bind PD-1 or its ligand, PD-L1.

According to certain aspects of the presently disclosed invention, the immune checkpoint therapy may include an inhibitor of the PD-1 checkpoint, which may decrease, block, inhibit, abrogate, or interfere with signal transduction resulting from the interaction of PD-1 with one or more of its binding partners, such as PD-L1 and PD-L2. The inhibitor of the PD-1 checkpoint may be an anti-PD-1 antibody, antigen binding fragment, fusion proteins, oligopeptides, and other molecules that decrease, block, inhibit, abrogate or interfere with signal transduction resulting from the interaction of PD-1 with PD-L1 and/or PD-L2. In some embodiments, a PD-1 checkpoint inhibitor reduces the negative co-stimulatory signal mediated by or through cell surface proteins expressed on T lymphocytes so as render a dysfunctional T-cell less dysfunctional (e.g., enhancing effector responses to antigen recognition). In some embodiments, the PD-1 checkpoint therapy is an anti-PD-1 antibody.

Thus, according to certain aspects of the present invention, the immune checkpoint therapy may include a monoclonal antibody against an immune checkpoint inhibitor (ICI) such as against CTLA-4, PD-1, or PD-L1.

According to certain aspects, the ICI antibody may be an antibody against PD-1. The ICI antibody may be an anti-PD-1 antibody, such as nivolumab. For example, the inhibitors of PD-1 biological activity (or its ligands) disclosed in U.S. Pat. No. 7,029,674. Exemplary antibodies against PD-1 include: Anti-mouse PD-1 antibody Clone J43 (Cat #BE0033-2) from BioXcell; Anti-mouse PD-1 antibody Clone RMP1-14 (Cat #BE0146) from BioXcell; mouse anti-PD-1 antibody Clone EH12; Merck's MK-3475 anti-mouse PD-1 antibody (Keytruda®, pembrolizumab, lambrolizumab); and AnaptysBio's anti-PD-1 antibody, known as ANB011; antibody MDX-1 106 (ONO-4538); Bristol-Myers Squibb's human IgG4 monoclonal antibody nivolumab (Opdivo®, BMS-936558, MDX1106); AstraZeneca's AMP-514, and AMP-224; and Pidilizumab (CT-011), CureTech Ltd.

According to certain aspects, the immune checkpoint therapy is an inhibitor of PD-L1. Exemplary inhibitors of PD-L1 include antibodies (e.g., an anti-PD-L1 antibody, i.e., ICI antibody), RNAi molecules (e.g., anti-PD-L1 RNAi), antisense molecules (e.g., an anti-PD-L1 antisense RNA), dominant negative proteins (e.g., a dominant negative PD-L1 protein), and small molecule inhibitors. An exemplary anti-PD-L1 antibody includes clone EH12. Exemplary antibodies against PD-L1 include: Genentech's MPDL3280A (RG7446); anti-mouse PD-L1 antibody Clone 10F.9G2 (Cat #BE0101) from BioXcell; anti-PD-L1 monoclonal antibody MDX-1105 (BMS-936559) and BMS-935559 from Bristol-Meyer's Squibb; MSB0010718C; mouse anti-PD-L1 Clone 29E.2A3; and AstraZeneca's MEDI4736 (Durvalumab).

According to certain aspects, the immune checkpoint therapy is an inhibitor of PD-L2 or may reduce the interaction between PD-1 and PD-L2. Exemplary inhibitors of PD-L2 include antibodies (e.g., an anti-PD-L2 antibody, i.e., ICI antibody), RNAi molecules (e.g., an anti-PD-L2 RNAi), antisense molecules (e.g., an anti-PD-L2 antisense RNA), dominant negative proteins (e.g., a dominant negative PD-L2 protein), and small molecule inhibitors. Antibodies include monoclonal antibodies, humanized antibodies, deimmunized antibodies, and Ig fusion proteins.

According to certain aspects, the immune checkpoint therapy may be an inhibitor of CTLA-4, such as an anti-CTLA-4 antibody, i.e., ICI antibody. According to one aspect, the ICI antibody may be ipilimumab. The anti-CTLA-4 antibody may block the binding of CTLA-4 to CD80 (B7-1) and/or CD86 (B7-2) expressed on antigen presenting cells. Exemplary antibodies against CTLA-4 include: Bristol Meyers Squibb's anti-CTLA-4 antibody ipilimumab (also known as Yervoy®, MDX-010, BMS-734016 and MDX-101); anti-CTLA4 Antibody, clone 9H10 from Millipore; Pfizer's tremelimumab (CP-675,206, ticilimumab); and anti-CTLA-4 antibody clone BNI3 from Abcam. According to certain aspects, the immune checkpoint inhibitor may be a nucleic acid inhibitor of CTLA-4 expression.

CD137 (also known "TNF receptor superfamily member 9") is a costimulatory receptor member of the tumor necrosis factor receptor superfamily, mediating CD28-dependent and independent T-cell co-stimulation (Bartkowiak, 2015). CD137 is inducibly expressed by T cells, natural killer (NK) cells, dendritic cells (DC), B cells, and other cells of the immune system. The protein is composed of a 255-amino acid protein having a short N-terminal cytoplasmic portion, a transmembrane region, and an extracellular domain that possesses 3 cysteine-rich motifs. Ligation of CD137 by its ligand CD137L (4-1BBL; TNFSF9), which is mainly, though not exclusively, expressed on Antigen-Presenting Cells (APCs), evokes various T cell responses such as cell expansion, increased cytokine secretion and the prevention of activation-induced cell death. Thus, such ligation serves to activate the immune system. However, cis-interactions between CD137 and CD137L also potently downregulate the expression of CD137L (Kwon, 2015). The CD137 ligand thus functions to control the extent and kinetics of CD137-mediated immune system activation (Kwon, 2015). Significantly, CD137 expressed on human NK cells becomes upregulated upon binding to anti-tumor antibodies that have become bound to tumor cells (Wei, 2014).

Thus, according to certain aspects of the presently disclosed invention, the immune checkpoint therapy may include an antibody against CD137, which could be used to activate the immune system and thereby provide a therapy for cancer in combination with the presently disclosed HER3 targeting agents. Exemplary anti-CD137 antibodies that may be used are disclosed in U.S. Publication Nos. 20140274909; 20130280265; 20130273078; 20130071403; 20120058047; 20110104049; 20110097313; 20080166336; 20080019905; 20060188439; 20060182744; 20060121030; and 20030223989.

According to certain aspects of the present invention, the immune checkpoint therapy may include more than one modulator of an immune checkpoint protein. As such, the immune checkpoint therapy may include a first antibody or inhibitor against a first immune checkpoint protein and a second antibody or inhibitor against a second immune checkpoint protein.

D. DNA Damage Response Inhibitors

The additional agents administered in conjunction with the HER3 targeting agent may be one or more DNA damage response inhibitors (DDRi). DNA damage can be due to endogenous factors, such as spontaneous or enzymatic reactions, chemical reactions, or errors in replication, or may be due to exogenous factors, such as UV or ionizing radiation or genotoxic chemicals. The repair pathways that overcome this damage are collectively referred to as the DNA damage response or DDR. This signaling network acts to detect and orchestrate a cell's response to certain forms of DNA damage, most notably double strand breaks and replication stress. Following treatment with many types of DNA damaging drugs and ionizing radiation, cells are reliant on the DDR for survival. It has been shown that disruption of the DDR can increase cancer cell sensitivity to these DNA damaging agents and thus may improve patient responses to such therapies.

Within the DDR, there are several DNA repair mechanisms, including base excision repair, nucleotide excision repair, mismatch repair, homologous recombinant repair, and non-homologous end joining. Approximately 450 human DDR genes code for proteins with roles in physiological processes. Dysregulation of DDR leads to a variety of disorders, including genetic, neurodegenerative, immune, cardiovascular, and metabolic diseases or disorders and cancers. For example, the genes OGG1 and XRCC1 are part of the base excision repair mechanism of DDR, and mutations in these genes are found in renal, breast, and lung cancers, while the genes BRCA1 and BRCA2 are involved in homologous recombination repair mechanisms and mutations in these genes leads to an increased risk of breast, ovarian, prostate, pancreatic, as well as gastrointestinal and hematological cancers, and melanoma. Exemplary DDR genes are provided in Table 3.

An object of the presently disclosed invention is to administer radiolabeled HER3 targeting agents that deliver ionizing radiation in combination with a DDRi. Thus, according to certain aspects, the additional agent(s) administered with the HER3 targeting agent may target proteins in the DDR, i.e., DDR inhibitors or DDRi, thus maximizing DNA damage or inhibiting the repair if the damage, such as in G1 and S-phase and/or preventing repair in G2, ensuring the maximum amount of DNA damage is taken into mitosis, leading to cell death.

TABLE 3

| DNA repair mechanism | Gene examples | Cancer |
|---|---|---|
| Base Excision Repair | OGGI | Renal, breast and lung cancer |
| | XRCC1 | Non-small cell lung cancer |
| Nucleotide Excision Repair | ERCC1 | Lung and skin cancer, and glioma |
| | XP | Xeroderma pigmentosum predisposing to skin cancer. Also increased risk of bladder and lung cancer |
| Mismatch Repair | MSH2, MLH1 | Lynch syndrome predisposing to colorectal cancer as well as endometrial, ovarian, stomach, small intestine, hepatobiliary tract, upper urinary tract, brain and skin cancer |
| Homologous Recombinant Repair | BRCA1, BRCA2 | Increased risk of breast, ovarian, prostate, pancreatic, as well as gastrointestinal and hematological cancer, and melanoma |
| Non-homologous End Joining | KU70 | Breast, colorectal and lung cancer |
| | KU80 | Lung cancer |
| Cell cycle checkpoints | ATM | Ataxia-telangiectasia predisposing to leukemia, breast and pancreatic cancer |
| | ATR | Leukemia, lymphoma, gastric and endometrial cancer |

Moreover, one or more DDR pathways may be targeted to ensure cell death, i.e., lethality to the targeted cancer cells. For example, mutations in the BRCA1 and 2 genes alone may not be sufficient to ensure cell death, as other pathways, such as the PARP1 base excision pathway, may act to repair the DNA damage. Thus, combinations of multiple DDRi inhibitors or combining DDRi with antiangiogenic agents or immune checkpoint inhibitors, such as listed hereinabove, are possible and an object of the presently disclosed invention.

Exemplary DDRi—ATM and ATR Inhibitors

Ataxia telangiectasia mutated (ATM) and Ataxia talangiectasia mutated and Rad-3 related (ATR) are members of the phosphatidylinositol 3-kinase-related kinase (PIKK) family of serine/threonine protein kinases.

ATM is a serine/threonine protein kinase that is recruited and activated by DNA double-strand breaks. The ATM phosphorylates several key proteins that initiate activation of a DNA damage checkpoint, leading to cell cycle arrest, DNA repair, or cellular apoptosis. Several of these targets, including p53, CHK2, and H2AX, are tumor suppressors. The protein is named for the disorder ataxia telangiectasia caused by mutations of the ATM. The ATM belongs to the superfamily of phosphatidylinositol 3-kinase-related kinases (PIKKs), which includes six serine/threonine protein kinases that show a sequence similarity to a phosphatidylinositol 3-kinase (PI3K).

Like ATM, ATR is one of the central kinases involved in the DDR. ATR is activated by single stranded DNA structures, which may for example arise at resected DNA DSBs or stalled replication forks. When DNA polymerases stall during DNA replication, the replicative helicases continue to unwind the DNA ahead of the replication fork, leading to the generation of long stretches of single stranded DNA (ssDNA).

ATM has been found to assist cancer cells by providing resistance against chemotherapeutic agents and thus favors tumor growth and survival. Inhibition of ATM and/or ATR may markedly increase cancer cell sensitivity to DNA damaging agents, such as the ionizing radiation provided by the radiolabeled HER3 targeting agent. Accordingly, an object of the presently disclosed invention includes administration of an inhibitor of ATM (ATMi) and/or ATR (ATRi), in combination with the HER3 targeting agents, to inhibit or kill cancer cells, such as those expressing tor overexpressing HER3.

The inhibitor of ATM (ATMi) or ATR (ATRi) may be an antibody, peptide, or small molecule that targets ATM or ATR, respectively. Alternatively, an ATMi or ATRi may reduce or eliminate activation of ATM or ATR by one or more signaling molecules, proteins, or other compounds, or can result in the reduction or elimination of ATM or ATR activation by all signaling molecules, proteins, or other compounds. ATMi and/or ATRi also include compounds that inhibit their expression (e.g., compounds that inhibit ATM or ATR transcription or translation). An exemplary ATMi KU-55933 suppresses cell proliferation and induces apoptosis. Other exemplary ATMi include at least KU-59403, wortmannin, CP466722, and KU-60019. Exemplary ATRi include at least Schisandrin B, NU6027, NVP-BEA235, VE-821, VE-822, AZ20, and AZD6738.

Exemplary DDRi—Wee1 Inhibitors

The checkpoint kinase Wee1 catalyzes an inhibitory phosphorylation of both CDK1 (CDC2) and CDK2 on tyrosine 15, thus arresting the cell cycle in response to extrinsically induced DNA damage. Deregulated Wee1 expression or activity is believed to be a hallmark of pathology in several types of cancer. For example, Wee1 is often overexpressed in glioblastomas, malignant melanoma, hepatocellular carcinoma, breast cancer, colon carcinoma, lung carcinoma, and head and neck squamous cell carcinoma. Advanced tumors with an increased level of genomic instability may require functional checkpoints to allow for repair of such lethal DNA damage. As such, the present inventors believe that Wee1 represents an attractive target in advanced tumors where its inhibition is believed to result in irreparable DNA damage. Accordingly, an object of the presently disclosed invention includes administration of an inhibitor of Wee1, in combination with the HER3 targeting agents, to inhibit or kill cancer cells, such as those expressing tor overexpressing HER3.

A Wee1 inhibitor may be an antibody, peptide, or small molecule that targets Wee1. Alternatively, a Wee1 inhibitor may reduce or eliminate Wee1 activation by one or more signaling molecules, proteins, or other compounds, or can result in the reduction or elimination of Wee1 activation by all signaling molecules, proteins, or other compounds. The term also includes compounds that decrease or eliminate the activation or deactivation of one or more proteins or cell signaling components by Wee1 (e.g., a Wee1 inhibitor can decrease or eliminate Wee1-dependent inactivation of cyclin and Cdk activity). Wee1 inhibitors also include compounds that inhibit Wee1 expression (e.g., compounds that inhibit Wee1 transcription or translation).

Exemplary Wee1 inhibitors include AZD-1775 (i.e., adavosertib), and inhibitors such as those described in, e.g., U.S. Pat. Nos. 7,834,019; 7,935,708; 8,288,396; 8,436,004; 8,710,065; 8,716,297; 8,791,125; 8,796,289; 9,051,327; 9,181,239; 9,714,244; 9,718,821; and 9,850,247; U.S. Pub. Nos. US 20100113445 and 20160222459; and International Pub. Nos. WO2002090360, 2015019037, 2017013436, 2017216559, 2018011569, and 2018011570.

Further Wee1 inhibitors include a pyrazolopyrimidine derivative, a pyridopyrimidine, 4-(2-chlorophenyl)-9-hydroxypyrrolo[3,4-c]carbazole-1,3-(2H, 6H)-dione (CAS No. 622855-37-2), 6-butyl-4-(2-chlorophenyl)-9-hydroxypyrrolo[3,4-c]carbazole-1,3-(2H,6H)-dione (CAS No. 62285550-9), 4-(2-phenyl)-9-hydroxypyrrolo[3,4-c]carbazole-1,3-(2H,6H)-dione (CAS No. 1177150-89-8), and an anti-Wee1 small interfering RNA (siRNA) molecule.

Exemplary DDRi—PARP Inhibitors

Another exemplary type of DDRi that may be used are inhibitors of poly(ADP-ribose) polymerase ("PARP"). Inhibitors of the DNA repair protein PARP, referred to individually and collectively as "PARPi", have been approved for use in a range of solid tumors, such as breast and ovarian cancer, particularly in patients having BRCA1/2 mutations. BRCA1 and 2 function in homologous recombination repair (HRR). When mutated, they induce genomic instability by shifting the DNA repair process from conservative and precise HRR to non-fidelitous methods such as DNA endjoining, which can produce mutations via deletions and insertions.

PARPi have been shown to exhibit synthetic lethality, as exhibited by potent single agent activity, in BRCA1/2 mutant cells. This essentially blocks repair of single-strand DNA breaks. Since HRR is not functional in these tumor cells, cell death results. Because most tumors do not carry BRCA1 or BRCA2 mutations, the potency of PARPi in such tumors is far less pronounced.

To date, the FDA has approved four PARPi drugs (olaparib, niraparib, rucaparib and talazoparib) as monotherapy agents, specifically in patients with germline and somatic mutations in the BRCA1 and BRCA2 genes. Along with veliparib, olaparib, niraparib and rucaparib were among the first generation of PARPi that entered clinical trials. Their IC50 values were found to be in the nanomolar range. In contrast, second generation PARPi like talazoparib have IC50 values in the picomolar range.

These PARPi all bind to the binding site of the cofactor, b nicotinamide adenine dinucleotide (b-NAD+), in the catalytic domain of PARP1 and PARP2. The PARP family of enzymes use NAD+ to covalently add Poly(ADP-ribose) (PAR) chains onto target proteins, a process termed "PARylation." PARP1 (which is the best-studied member) and PARP2, are important components of the DNA damage response (DDR) pathway. PARP1 is involved in the repair of single-stranded DNA breaks, and possibly other DNA lesions (Woodhouse, et al.; Krishnakumar, et al.). Through its zinc finger domains, PARP1 binds to damaged DNA and then PARylates a series of DNA repair effector proteins, releasing nicotinamide as a by-product (Krishnakumar, et al.). Subsequently, PARP1 auto-PARylation leads to release of the protein from the DNA. The available PARPi, however, differ in their capability to trap PARP1 on DNA, which seems to correlate with cytotoxicity and drug efficacy. Specifically, drugs like talazoparib and olaparib are more effective in trapping PARP1 than are veliparib (Murai, et al., 2012; Murai, et al., 2014).

The efficacy of PARPi in ovarian cancer and breast cancer patients who have loss-of-function mutations in BRCA1 or BRCA2 genes is largely attributed to the genetic concept of synthetic lethality: that proteins of BRCA 1 and 2 normally maintain the integrity of the genome by mediating a DNA repair process, known as homologous recombination repair (HRR); and PARPi causes a persistent DNA lesion that, normally, would otherwise be repaired by HR. In the presence of PARPi, PARP1 is trapped on DNA which stalls progression of the replication fork. This stalling is cytotoxic unless timely repaired by the HR system. In cells lacking effective HR, they are unable to effectively repair these DNA lesions, and thus die.

Again, mutations in BRCA genes and others in the HRR system are not prevalent in many cancer types. So, to better harness the therapeutic benefits of PARPi in such cancers, one can induce "artificial" synthetic lethality by pairing a PARPi with either chemotherapy or radiation therapy. Preclinical studies have demonstrated that combining radiation therapy and PARPi can increase the sensitivity of BRCA1/2 mutant tumor cells to PARP inhibition and extend the sensitivity of non-mutant BRCA tumors to PARP inhibition. Additional studies have shown that ionizing radiation (IR) itself can mediate PARPi synthetic lethality in tumor cells.

Accordingly, an object of the presently disclosed invention is to administer radiolabeled HER3 targeting agents that deliver ionizing radiation in combination with a PARPi.

In the various embodiments of this invention, the PARPi may be any known agent performing that function, and preferably, one approved by the FDA. Preferably, the PARPi is olaparib (Lynparza®), niraparib (Zejula®), rucaparib (Rubraca®) or talazoparib (Talzenna®).

Clinically, therapy with PARPi has resulted in sustained anti-tumor responses in a range of cancers including ovarian, prostate, pancreatic, and triple-negative breast cancers (TNBC). In one clinical trial, TNBC patients with germline BRCA1/2 mutations were treated with the PARPi, olaparib. While this therapy demonstrated a higher disease stabilization rate in BRCA1/2-mutant compared to non-mutant patients, there were no sustained responses achieved in either cohort (Gelmon, 2011).

The present inventors realized that the effect of PARPi may be improved through increases in dsDNA breaks induced by ionizing radiation provided by a HER3 targeting agent while these repair pathways are being blocked by the PARPi. Exemplary PARPi include olaparib, niraparib, rucaparib and talazoparib.

E. CD47 Blockades

The additional agents administered with the HER3 targeting agent may be a CD47 blockade, such as any agent that interferes with, or reduces the activity and/or signaling between CD47 (e.g., on a target cell) and SIRPα (e.g., on a phagocytic cell) through interaction with either CD47 or SIRPα. Non-limiting examples of suitable CD47 blockades include CD47 and/or SIRPα reagents, including without limitation SIRPα polypeptides, anti-SIRPα antibodies, soluble CD47 polypeptides, and anti-CD47 antibodies or antibody fragments.

Additional examples of a CD47 blockade include agents that modulate the expression of CD47 and/or SIRPα. For example, such agents may include nucleic acid approaches such as phosphorodiamidate morpholino oligomers (PMO) that block translation of CD47 or antibodies specific for human CD47 that modulate, e.g., block, inhibit, reduce, antagonize, neutralize or otherwise interfere with CD47 expression. The CD47 antibodies or anti-sense approaches may inhibit CD47 expression (e.g., inhibiting cell surface expression of CD47), activity, and/or signaling, or may interfere with the interaction between CD47 and SIRPα. The agents provided herein completely or partially reduce or otherwise modulate CD47 expression or activity upon binding to, or otherwise interacting with, CD47, e.g., a human CD47. The reduction or modulation of a biological function of CD47 is complete, significant, or partial upon interaction between the antibodies and the human CD47 polypeptide and/or peptide. The agents are considered to inhibit CD47 expression or activity when the level of CD47 expression or activity in the presence of the antibody is decreased by at least 50%, e.g., by 60%, 70%, 80%, 90%, 95%, 96%, 98%, 99%, or 100% as compared to the level of CD47 expression or activity in the absence of interaction, e.g., binding, with the antibody described herein.

According to certain aspects, an anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). Non-limiting examples of suitable antibodies include clones B6H12, 5F9, 8B6, and C3 and any of those described in International Pub. No. WO2011/143624 and U.S. Pub. 20210246206. Suitable anti-CD47 antibodies include fully human, humanized or chimeric versions of such antibodies.

Exemplary human or humanized antibodies especially useful for in vivo applications in humans due to their low antigenicity include at least monoclonal antibodies against CD47, such as Hu5F9-G4, a humanized monoclonal antibody available from Gilead as Magrolimab (Sikic, et al. (2019) *Journal of Clinical Oncology* 37:946); Lemzoparlimab and TJC4 from I-Mab Biopharma; AO-176 from Arch Oncology, Inc; AK117 from Akesobio Australia Pty; IMC-002 from Innovent Biologics; ZL-1201 from Zia Lab; SHR-1603 from Jiangsu HengRui Medincine Co.; and SRF231 from Surface Oncology. Bispecific monoclonal antibodies are also available, such as IBI-322, targeting both CD47 and PD-L1 from Innovent Biologics. Antibodies against SIRPa are also possible, such as ALX148 from Alx Oncology; BI 765063 (OSE-172) from OSE; as well as small molecule inhibitors, such as RRx-001 (1-bromoacetyl-3,3 dinitroazetidine) from EpicentRx and Azelnidipine (CAS number 123524-52-7) or pharmaceutically acceptable salts thereof. See also Table 4 for further description of exemplary agents.

TABLE 4

| Company | Approach | Agent/Program |
|---|---|---|
| Akesobio Australia Pty Ltd | CD47 mAb | AK117 |
| Arch Oncology (Tioma Therapeutics) | CD47 mAb | AO-176 |
| Elpiscience Biopharma Inc. | CD47 | ES004 |
| EpicentRx | Small molecule inhibitor of dinitroazetidine hypoxia sensor to downregulate CD47/SIRPα | RRx-001 (1-bromoacetyl-3,3 dinitroazetidine) |
| ImmuneOncia Therapeutics | CD47 mAb human | IMC-002 |
| Innovent Biologics | CD47 mAb<br>CD47/PD-L1 bispecific mAb | IBI-188 (CD47 mAb)<br>IBI-322 (Bispecific) |
| OSE | SIRPα mAb | BI 765063 (OSE-172) |
| Zai Lab | CD47 mAb | ZL-1201 |
| Alx Oncology | High-affinity SIRPα-Fc | ALX148 |
| Gilead/Forty Seven | CD47 mAb<br>SIRPα mAb | Magrolimab FSI-189 |
| I-Mab Biopharma | CD47 mAb | TJC4 |
| Jiangsu HengRui Medicine Co., Ltd. | CD47 mAb | SHR-1603 |
| Surface Oncology | CD47 mAb human | SRF231 |
| Morphiex | CD47 targeting phosphorodiamidate morpholino oligomers | MBT-001 |

AO-176, in addition to inducing tumor phagocytosis through blocking the CD47-SIRPα interaction, is reported to preferentially bind tumor cells versus normal cells (particularly RBCs where binding is negligible) and directly kills tumor versus normal cells.

According to certain aspects, a SIRPa reagent may include the portion of SIRPa that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. For example, the CD47 blocking agent used in various aspects of the invention may be any of those disclosed in U.S. Pat. No. 9,969,789 including but not limited to the SIRPα-IgG Fc fusion proteins disclosed therein, such as TTI-621 and TTI-622, both of which preferentially bind CD47 on tumor cells while also engaging activating Fc receptors. A SIRPα-IgG Fc fusion protein including the amino acid sequence SEQ ID NO:116, SEQ ID NO:117, or SEQ ID NO:118 may, for example, be used.

Therapeutically effective doses of an anti-CD47 antibody or other protein CD47 inhibitor may be a dose that leads to sustained serum levels of the protein of about 40 μg/ml or more (e.g., about 50 ug/ml or more, about 60 ug/ml or more, about 75 ug/ml or more, about 100 ug/ml or more, about 125 ug/ml or more, or about 150 ug/ml or more). Therapeutically effective doses or administration of a CD47 blockade, such as an anti-CD47 antibody or SIRPα fusion protein or small molecule, include, for example, amounts of 0.05-10 mg/kg (agent weight/subject weight), such as at least 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg; or not more than 10 mg/kg, 9.5 mg/kg, 9.0 mg/kg, 8.5 mg/kg, 8.0 mg/kg, 7.5 mg/kg, 7.0 mg/kg, 6.5 mg/kg, 6.0 mg/kg, 5.5 mg/kg, 5.0 mg/kg, 4.5 mg/kg, 4.0 mg/kg, 3.5 mg/kg, 3.0 mg/kg, 2.5 mg/kg, 2.0 mg/kg, 1.5 mg/kg, 1.0 mg/kg, or any combination of these upper and lower limits. Therapeutically effective doses of a small molecule CD47 blockade such as those disclosed herein also, for example, include 0.01 mg/kg to 1,000 mg/kg and any subrange or value of mg/kg therein such as 0.01 mg/kg to 500 mg/kg or 0.05 mg/kg to 500 mg/kg, or 0.5 mg/kg to 200 mg/kg, or 0.5 mg/kg to 150 mg/kg, or 1.0 mg/kg to 100 mg/kg, or 10 mg/kg to 50 mg/kg.

According to certain aspects, the anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPa because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis. In some cases, a suitable soluble CD47 polypeptide can be a fusion protein (for example, as described in U.S. Pub. No. 20100239579).

Advantageously, CD47 blockade can enhance the cytotoxic and prophagocytotic effect of a radiolabeled targeting agent, such as a radiolabeled HER3 and/or HER2 targeting agent, while reducing the dose-limiting radiotoxicity of the targeting agent, thereby improving tolerability and permitting higher radiation doses of the targeting agent to be used/tolerated in the treatment of a subject.

EXAMPLES

Example 1

Production of Radiolabeled HER3 Targeting Agent

The HER3 targeting agent, such as a monoclonal antibody against HER3, may be labeled with Indium-111 ($^{111}$In) or Actinium-225 ($^{225}$Ac) according to procedures detailed in International Publication No. WO 2017/155937 and US Provisional Patent Application No. 63/042,651 filed Dec. 9, 2019 titled "Compositions and methods for preparation of site-specific radioconjugates."

Radiolabeling: As example, the antibody may be conjugated to a chelator-bearing linker, for example, as described herein or in the preceding patent applications. An exemplary linker includes at least dodecane tetraacetic acid (DOTA), wherein a goal of the conjugation reaction is to achieve a DOTA-antibody ratio of 3:1 to 5:1. Chelation with the radionuclide $^{111}$In or $^{225}$Ac may then be performed and efficiency and purity of the resulting $^{111}$In- or $^{225}$Ac-labeled anti-HER3 antibody may be determined by HPLC and iTLC.

An exemplary labeling reaction for $^{225}$Ac is as follows: A reaction including 15 μl 0.15M $NH_4OAc$ buffer, pH=6.5 and 2 μL (10 μg) DOTA-anti-HER3 (5 mg/ml) may be mixed in an Eppendorf reaction tube, and 4 μL $^{225}$AC (10 μCi) in 0.05 M HCl subsequently added. The contents of the tube may be mixed with a pipette tip and the reaction mixture incubated at 37° C. for 90 min with shaking at 100 rpm. At the end of the incubation period, 3 μL of a 1 mM DTPA solution may be added to the reaction mixture and incubated at room temperature for 20 min to bind the unreacted $^{225}$AC into the $^{225}$Ac-DTPA complex. Instant thin layer chromatography with 10 cm silica gel strip and 10 mM EDTA/normal saline mobile phase may be used to determine the radiochemical purity of $^{225}$Ac-DOTA-anti-HER3 through separating $^{225}$Ac-labeled anti-HER3 ($^{225}$Ac-DOTA-anti-HER3) from free $^{225}$Ac ($^{225}$Ac-DTPA). In this system, the radiolabeled antibody stays at the point of application and $^{225}$Ac-DTPA moves with the solvent front. The strips may be cut in halves and counted in the gamma counter equipped with the multichannel analyzer using channels 72-110 for $^{225}$AC to exclude its daughters.

Purification: An exemplary radiolabeled HER3 targeting agent, such as $^{225}$Ac-DOTA-anti-HER3, may be purified either on PD10 columns pre-blocked with 1% HSA or on Vivaspin centrifugal concentrators with a 50 kDa MW cut-off with 2×1.5 mL washes, 3 min per spin. HPLC analyses of the $^{225}$Ac-DOTA-anti-HER3 after purification may be conducted using a Waters HPLC system equipped with flow-through Waters UV and Bioscan Radiation detectors, using a TSK3000SW XL column eluted with PBS at pH=7.4 and a flow rate of 1 ml/min.

Stability determination: An exemplary radiolabeled HER3 targeting agent, such as $^{225}$Ac-DOTA-anti-HER3, may be used for stability determination, wherein the $^{225}$Ac-DOTA-anti-HER3 may be tested either in the original volume or diluted (2-10 fold) with the working buffer (0.15 M $NH_4OAc$) and incubated at room temperature (rt) for 48 hours or at 4° C. for 96 hours and tested by ITLC. Stability is determined by comparison of the intact radiolabeled anti-HER3 before and after incubation. Other antibodies labeled with $^{225}$AC have been found to be stable at 4° C. for up to 96 hrs.

Immunoreactivity (IR) determination: An exemplary radiolabeled HER3 targeting agent, such as $^{225}$Ac-DOTA-anti-HER3, may be used in immunoreactivity experiments. HER3 positive cells and control HER3 negative cells may be used in the amounts of 1.0-7.5 million cells per sample to investigate the amount of binding (percent radioactivity binding to cells after several washes; or using an immunoreactive fraction (IRF) bead assay may be performed according to methods disclosed in as described by Sharma, 2019). Prior assays for other antibodies radiolabeled with $^{111}$In or $^{225}$Ac demonstrated about 50-60% immunoreactivity.

Example 2

Exemplary PARPi Administration and Dosing Regimes (A) Olaparib (Lynparza®)—Normal and Reduced Dosing Regimens Olaparib is sold by AstraZeneca under the brand name Lynparza®. Lynparza® is sold in tablet form at 100 mg and 150 mg. The dosage is 300 mg taken orally twice daily for a daily total of 600 mg. Dosing continues until disease progression or unacceptable toxicity. This dosing regimen is referred to herein as the "normal" human dosing regimen for Lynparza®, regardless of the disorder treated. Any dosing regimen having a shorter duration (e.g., 21 days) or involving the administration of less Lynparza® (e.g., 300 mg/day) is referred to herein as a "reduced" human dosing regimen. Examples of reduced human dosing regimens include the following: (i) 550 mg/day; (ii) 500 mg/day; (iii) 450 mg/day; (iv) 400 mg/day; (v) 350 mg/day; (vi) 300 mg/day; (vii) 250 mg/day; (viii) 200 mg/day; (ix) 150 mg/day; (x) 100 mg/day; or (xi) 50 mg/day.

(B) Niraparib (Zejula®)—Normal and Reduced Dosing Regimens

Niraparib is sold by Tesaro under the brand name Zejula®. Zejula® is sold in capsule form at 100 mg. The dosage is 300 mg taken orally once daily. Dosing continues until disease progression or unacceptable adverse reaction. This dosing regimen is referred to herein as the "normal" human dosing regimen for Zejula®, regardless of the disorder treated. Any dosing regimen having a shorter duration (e.g., 21 days) or involving the administration of less Zejula® (e.g., 150 mg/day) is referred to herein as a "reduced" human dosing regimen. Examples of reduced human dosing regimens include the following: (i) 250 mg/day; (ii) 200 mg/day; (iii) 150 mg/day; (iv) 100 mg/day; or (v) 50 mg/day.

(C) Rucaparib (Rubraca®)—Normal and Reduced Dosing Regimens

Rucaparib is sold by Clovis Oncology, Inc. under the brand name Rubraca™. Rubraca™ is sold in tablet form at 200 mg and 300 mg. The dosage is 600 mg taken orally twice daily for a daily total of 1,200 mg. Dosing continues until disease progression or unacceptable toxicity. This dosing regimen is referred to herein as the "normal" human dosing regimen for Rubraca™, regardless of the disorder treated. Any dosing regimen having a shorter duration (e.g., 21 days) or involving the administration of less Rubraca™ (e.g., 600 mg/day) is referred to herein as a "reduced" human dosing regimen. Examples of reduced human dosing regimens include the following: (i) 1,150 mg/day; (ii) 1,100 mg/day; (iii) 1,050 mg/day; (iv) 1,000 mg/day; (v) 950 mg/day; (vi) 900 mg/day; (vii) 850 mg/day; (viii) 800 mg/day; (ix) 750 mg/day; (x) 700 mg/day; (xi) 650 mg/day; (xii) 600 mg/day; (xiii) 550 mg/day; (xiv) 500 mg/day; (xv) 450 mg/day; (xvi) 400 mg/day; (xvii) 350 mg/day; (xviii) 300 mg/day; (xix) 250 mg/day; (xx) 200 mg/day; (xxi) 150 mg/day; or (xxii) 100 mg/day.

(D)—Talazoparib (Talzenna™)—Normal and Reduced Dosing Regimens

Talazoparib is sold by Pfizer Labs under the brand name Talzenna™. Talzenna™ is sold in capsule form at 1 mg. The dosage is 1 mg taken orally. Dosing continues until disease progression or unacceptable toxicity. This dosing regimen is referred to herein as the "normal" human dosing regimen for Talzenna™, regardless of the disorder treated. Any dosing regimen having a shorter duration (e.g., 21 days) or involving the administration of less Talzenna™ (e.g., 0.5 mg/day) is referred to herein as a "reduced" human dosing regimen. Examples of reduced human dosing regimens include the following: (i) 0.9 mg/day; (ii) 0.8 mg/day; (iii) 0.7 mg/day; (iv) 0.6 mg/day; (v) 0.5 mg/day; (vi) 0.4 mg/day; (vii) 0.3 mg/day; (viii) 0.2 mg/day; or (ix) 0.1 mg/day.

Example 3

Dosing Regimens for HER3 Targeting Agent and PARPi

A human patient may be treated according to the following regimen. One of olaparib, niraparib, rucaparib or talazoparib (PARPi) is orally administered according to one of the dosing regimens listed in Example 2, accompanied by intravenous administration of a radiolabeled HER3 targeting agent as detailed herein in either single or fractional administration. For example, the dosing regimens include, by way of example: (a) the PARPi and the HER3 targeting agent administered concurrently, wherein (i) each is administered beginning on the same day, (ii) the HER3 targeting agent is administered in a single dose or fractionated doses not less than one week apart, and (iii) the PARPi is administered daily or twice daily (as appropriate), and for a duration equal to or exceeding that of the HER3 targeting agent administration; or (b) the PARPi and HER3 targeting agent are administered concurrently, wherein (i) the PARPi administration precedes HER3 targeting agent administration by at least one week, (ii) the HER3 targeting agent is administered in a single dose or fractionated doses not less than one week apart, and (iii) the PARPi is administered daily or twice daily (as appropriate), and for a duration equal to or exceeding that of the HER3 targeting agent administration.

Example 4

Dosing Regimens for HER3 Targeting Agent and a CD47 Blockade

According to certain aspects of the present invention, the CD47 blocking agent may, for example, be a monoclonal antibody that prevents CD47 binding to SIRPα. Exemplary protein CD47 blockades include magrolimab, lemzoparlimab, AO-176, TTI-621, TTI-622, or a combination thereof. The CD47 blockade may alternatively, or additionally, include agents that modulate the expression of CD47 and/or SIRPa, such as phosphorodiamidate morpholino oligomers (PMO) that block translation of CD47 such as MBT-001 (PMO, morpholino, Sequence: 5'-CGTCACAGGCAGGACCCACTGCCCA-3') [SEQ ID NO:114]) or any of the PMO oligomer CD47 inhibitors disclosed in any of U.S. Pat. Nos. 8,557,788, 8,236,313, 10,370,439 and Int'l Pub. No. WO2008060785. Therapeutically effective doses of anti-CD47 antibodies include at least 0.05-10 mg/kg. Thus, methods of the present invention may include administering one or more of the anti-CD47 antibodies or other agents, accompanied by intravenous administration of a radiolabeled HER3 targeting agent as detailed herein in either single or fractional administration. For example, the dosing regimens include, by way of example: (a) the anti-CD47 antibody or agent and the HER3 targeting agent administered concurrently, wherein (i) each is administered beginning on the same day, (ii) the HER3 targeting agent is administered in a single dose or fractionated doses not less than one week apart, and (iii) the anti-CD47 antibody or agent is administered daily or twice daily (as appropriate), and for a duration equal to or exceeding that of the HER3 targeting agent administration; or (b) the anti-CD47 antibody or agent and HER3 targeting agent are administered concurrently, wherein (i) the anti-CD47 antibody or agent administration precedes HER3 targeting agent administration by at least one week, (ii) the HER3 targeting agent is administered in a single dose or fractionated doses not less than one week apart, and (iii) the anti-CD47 antibody or agent is administered daily or twice daily (as appropriate), and for a duration equal to or exceeding that of the HER3 targeting agent administration.

Example 5

Dosing Regimens for HER3 Targeting Agent and an ICI

According to certain aspects of the present invention, the immune checkpoint inhibitor (ICI) may be a monoclonal antibody against any of PD-1, PD-L1, PD-L2, CTLA-4, CD137. Therapeutically effective doses of these antibodies include at least 0.05-10 mg/kg. Thus, method of the present invention include administering one or more ICI, accompanied by intravenous administration of a radiolabeled HER3 targeting agent as detailed herein in either single or fractional administration. For example, the dosing regimens include, by way of example: (a) the ICI and the HER3 targeting agent administered concurrently, wherein (i) each is administered beginning on the same day, (ii) the HER3 targeting agent is administered in a single dose or fractionated doses not less than one week apart, and (iii) the ICI is administered daily or twice daily (as appropriate), and for a duration equal to or exceeding that of the HER3 targeting agent administration; or (b) the ICI and HER3 targeting agent are administered concurrently, wherein (i) the anti-CD47 antibody administration precedes HER3 targeting agent administration by at least one week, (ii) the HER3 targeting agent is administered in a single dose or fractionated doses not less than one week apart, and (iii) the ICI is administered daily or twice daily (as appropriate), and for a duration equal to or exceeding that of the HER3 targeting agent administration.

Without limitation, the following aspects are also provided by this disclosure:

Aspect 1. A method for treating a solid cancer in a mammalian subject such as a human patient, the method including: administering to the subject a therapeutically effective amount of a radiolabeled HER3 targeting agent.

Aspect 2. The method according to any preceding aspect, wherein the solid cancer is a breast cancer, gastric cancer, bladder cancer, cervical cancer, endometrial cancer, skin cancer, stomach cancer, testicular cancer, esophageal cancer, bronchioloalveolar cancer, prostate cancer, colorectal cancer, ovarian cancer, cervical epidermoid cancer, pancreatic cancer, lung cancer, renal cancer, head and neck cancer, or any combination thereof.

Aspect 3. The method according to any preceding aspect, wherein the solid cancer is colorectal cancer, gastric cancer, ovarian cancer, non-small cell lung carcinoma, head and neck squamous cell cancer, pancreatic cancer, renal cancer, or any combination thereof.

Aspect 4. The method according to any preceding aspect, wherein the solid cancer is a HER3-positive cancer such as a HER3-positive solid tumor.

Aspect 5. The method according to any preceding aspect, wherein the radiolabeled HER3 targeting agent includes a radiolabel selected from $^{131}I$, $^{121}I$, $^{123}I$, $^{90}Y$, $^{177}Lu$, $^{186}Re$, $^{188}Re$, $^{89}Sr$, $^{153}Sm$, $^{32}P$, $^{225}Ac$, $^{213}Bi$, $^{213}Po$, $^{211}At$, $^{212}Bi$, $^{213}Bi$, $^{223}Ra$, $^{227}Th$, $^{149}Tb$, $^{137}Cs$, $^{212}Pb$, $^{103}Pd$, or any of those disclosed herein, or any combination thereof.

Aspect 6. The method according to any preceding aspect, wherein the radiolabeled HER3 targeting agent includes a radiolabel selected from $^{131}I$, $^{90}Y$, $^{177}Lu$, $^{225}Ac$, $^{213}Bi$, $^{211}At$, $^{213}Bi$, $^{227}Th$, $^{212}Pb$, or any combination thereof.

Aspect 7. The method according to any preceding aspect, wherein the radiolabeled HER3 targeting agent includes an antibody against HER3.

Aspect 8. The method according to any preceding aspect, wherein the HER3 targeting agent includes an anti-HER3 monoclonal antibody such as any of those disclosed herein, such as a HER3 antibody selected from Patritumab, Seribantumab (MM-121), Lumretuzumab, Elgemtumab, GSK2849330, and AV-203 and any combination thereof.

Aspect 9. The method according to any preceding aspect, wherein the HER3 targeting agent includes a monoclonal antibody: (i) having a heavy chain sequence including SEQ ID NO:77 and/or a light chain sequence including SEQ ID NO:78; (ii) having an immunoglobulin heavy chain variable region including a CDR-H1 including SEQ ID NO:15, a CDR-H2 including SEQ ID NO:16, and/or a CDR-H3 including SEQ ID NO:17, and/or an immunoglobulin light chain variable region including a CDR-L1 including SEQ ID NO:18, a CDR-L2 including SEQ ID NO:19, and/or a CDR-L3 including SEQ ID NO:20; (iii) having an immunoglobulin heavy chain variable region including SEQ ID NO:21 and/or an immunoglobulin light chain variable region including SEQ ID NO:22; or (iv) having an immunoglobulin heavy chain amino acid sequence of SEQ ID NO:23 and/or an immunoglobulin light chain amino acid sequence of SEQ ID NO:24.

Aspect 10. The method according to any preceding aspect, wherein the HER3 targeting agent includes a monoclonal antibody including a heavy chain variable region having an amino acid sequence as set forth in SEQ. ID NO:7 and/or a light chain variable region having an amino acid sequence as set forth in SEQ. ID NO:8.

Aspect 11. The method according to any preceding aspect, wherein the HER3 targeting agent includes a monoclonal antibody including one or more of the heavy chain N-terminal region and complementarity determining regions (CDRs) having amino acid sequences as set forth in SEQ. ID NO:13 and/or 1-3, respectively; and/or including one or more of the light chain N-terminal region and CDRs having amino acid sequences as set forth in SEQ. ID NO:14 and/or 4-6, respectively.

Aspect 12. The method according to any preceding aspect, wherein the effective amount of the radiolabeled HER3 targeting agent is a maximum tolerated dose.

Aspect 13. The method according to any preceding aspect, wherein the radiolabeled HER3 targeting agent is $^{225}Ac$-, $^{177}Lu$-, or $^{131}I$-labeled.

Aspect 14. The method according to any preceding aspect, wherein the therapeutically effective amount of the radiolabeled HER3 targeting agent includes a single dose that delivers less than 2Gy, or less than 8 Gy, such as doses of 2 Gy to 8 Gy, to the subject.

Aspect 15. The method according to any preceding aspect, wherein the radiolabeled HER3 targeting agent is $^{225}Ac$-labeled, and the effective amount of the $^{225}Ac$-labeled HER3 targeting agent includes a dose of 0.1 to 50 uCi/kg body weight of the subject, or 0.2 to 20 uCi/kg body weight of the subject, or 0.5 to 10 uCi/kg subject body weight.

Aspect 16. The method according to any preceding aspect, wherein the radiolabeled HER3 targeting agent is a full-length antibody against HER3 that is $^{225}Ac$-labeled, and the effective of the $^{225}Ac$-labeled HER3 targeting agent includes less than 5 uCi/kg body weight of the subject, such as 0.1 to 5 uCi/kg body weight of the subject.

Aspect 17. The method according to any one of aspects 1 to 6, wherein the radiolabeled HER3 targeting agent is an antibody fragment, such as a minibody or nanobody against HER3 that is $^{225}Ac$-labeled, and the effective of the $^{225}Ac$-labeled HER3 targeting agent includes greater than 5 uCi/kg body weight of the subject, such as 5 to 20 uCi/kg body weight of the subject.

Aspect 18. The method according to any one of aspects 1 to 14, wherein the radiolabeled HER3 targeting agent is $^{225}Ac$-labeled, and the effective amount of the $^{225}Ac$-labeled HER3 targeting agent includes 2 μCi to 2 mCi, or 2 μCi to 250 μCi, or 75 μCi to 400 μCi.

Aspect 19. The method according to any one of aspects 1 to 14, wherein the radioisotope labeled HER3 targeting agent is $^{177}Lu$-labeled and the effective amount of the HER3 targeting agent includes a dose of less than 1000 uCi/kg body weight of the subject, such as a dose of 1 to 900 uCi/kg body weight of the subject, or 5 to 250 uCi/kg body weight of the subject or 50 to 450 uCi/kg body weight.

Aspect 20. The method according to any one of aspects 1 to 14, wherein the radioisotope labeled HER3 targeting agent is $^{177}Lu$-labeled, and the effective amount of the $^{177}Lu$-labeled HER3 targeting agent includes a dose of 10 mCi to at or below 30 mCi, or from at least 100 μCi to at or below 3 mCi, or from 3 mCi to at or below 30 mCi.

Aspect 21. The method according to any one of aspects 1 to 14, wherein the radiolabeled HER3 targeting agent is $^{131}$I-labeled, and the effective amount of the $^{131}$I-labeled HER3 targeting agent includes a dose of less than 1200 mCi, such as a dose of 25 to 1200 mCi, or 100 to 400 mCi, or 300 to 600 mCi, or 500 to 1000 mCi.

Aspect 22. The method according to any one of aspects 1 to 14, wherein the radiolabeled HER3 targeting agent is $^{131}$I-labeled, and the effective amount of the $^{131}$I-labeled HER3 targeting agent includes a dose of less than 200 mCi, such as a dose of 1 to 200 mCi, or 25 to 175 mCi, or 50 to 150 mCi.

Aspect 23. The method according to any preceding aspect, wherein the effective amount of the HER3 targeting agent includes a protein dose of less than 3 mg/kg body weight of the subject, such as from 0.001 mg/kg patient weight to 3.0 mg/kg patient weight, or from 0.005 mg/kg patient weight to 2.0 mg/kg patient weight, or from 0.01 mg/kg patient weight to 1 mg/kg patient weight, or from 0.1 mg/kg patient weight to 0.6 mg/kg patient weight, or 0.3 mg/kg patient weight, or 0.4 mg/kg patient weight, or 0.5 mg/kg patient weight, or 0.6 mg/kg patient weight.

Aspect 24. The method according to any preceding aspect, wherein the HER3 targeting agent is administered according to a dosing schedule selected from the group consisting of once every 7, 10, 12, 14, 20, 24, 28, 36, and 42 days throughout a treatment period, wherein the treatment period includes at least two doses.

Aspect 25. The method according to any one of aspects 1 to 6, wherein the HER3 targeting agent is a peptide or small molecule.

Aspect 26. The method according to any preceding aspect, further including administering to the subject a therapeutically effective amount of an immune checkpoint therapy, a chemotherapeutic agent, a DNA damage response inhibitor (DDRi), a CD47 blockade, or a combination thereof.

Aspect 27. The method according to aspect 26, wherein the immune checkpoint therapy includes an antibody or other blocking agent against CTLA-4, PD-1, TIM-3, VISTA, BTLA, LAG-3, TIGIT, CD28, OX40, GITR, CD137, CD40, CD4OL, CD27, HVEM, PD-L1, PD-L2, PD-L3, PD-L4, CD80, CD86, CD137-L, GITR-L, CD226, B7-H3, B7-H4, BTLA, TIGIT, GALS, KIR, 2B4, CD160, or CGEN-15049, or any combination of such antibodies and blocking agents.

Aspect 28. The method according to aspect 27, wherein the immune checkpoint therapy includes an antibody against PD-1, PD-L1, PD-L2, CTLA-4, CD137, or a combination thereof.

Aspect 29. The method according to aspect 26, wherein the DDRi includes a poly(ADP-ribose) polymerase inhibitor (PARPi), an ataxia telangiectasia mutated inhibitor (ATMi), an ataxia talangiectasia mutated and Rad-3 related inhibitor (ATRi), or a Wee1 inhibitor.

Aspect 30. The method according to aspect 29, wherein the PARPi includes one or more of olaparib, niraparib, rucaparib and talazoparib.

Aspect 31. The method according to aspect 29, wherein the ATMi includes one or more of KU-55933, KU-59403, wortmannin, CP466722, or KU-60019.

Aspect 32. The method according to aspect 29, wherein the ATRi includes one or more of Schisandrin B, NU6027, NVP-BEA235, VE-821, VE-822, AZ20, or AZD6738.

Aspect 33. The method according to aspect 29, wherein the Wee1 inhibitor includes AZD-1775 (i.e., adavosertib).

Aspect 34. The method according to aspect 26, wherein the CD47 blockade includes an agent, such as a monoclonal antibody that prevents CD47 binding to SIRPa and/or an agent that modulates CD47 expression.

Aspect 35: The method according to aspect 34, wherein the CD47 blockade includes one or more of magrolimab, lemzoparlimab, AO-176, TTI-621, TTI-622, or a combination thereof; and/or wherein the agent that modulates CD47 expression includes phosphorodiamidate morpholino oligomers (PMO) that reduce expression of CD47 (e.g., MBT-001).

Aspect 36: The method according to aspect 34, wherein the therapeutically effective amount of the CD47 blockade includes 0.05 to 5 mg/Kg patient weight.

Aspect 37. The method according to aspect 26, wherein the HER3 targeting agent is administered at least one week before the immune checkpoint therapy and/or the DDRi and/or the CD47 blockade; or wherein the immune checkpoint therapy and/or the DDRi and/or CD47 blockade is administered at least one week before the HER3 targeting agent.

Aspect 38. The method according to aspect 26, wherein the HER3 targeting agent is administered with one of the immune checkpoint therapy or the DDRi or the CD47 blockade, and the other of the immune checkpoint therapy or the DDRi or the CD47 blockade is administered either before or after the HER3 targeting agent.

Aspect 39. The method according to aspect 26, wherein the HER3 targeting agent is administered simultaneously with the immune checkpoint therapy and/or the DDRi and/or the CD47 blockade.

Aspect 40. The method according to any preceding aspect, wherein the HER3 targeting agent is a multi-specific antibody, wherein the multi-specific antibody includes: a first target recognition component which specifically binds to an epitope of HER3, and a second target recognition component which specifically binds to a different epitope of HER3 than the first target recognition component, or an epitope of a different antigen.

Aspect 41. The method according to aspect 40, wherein the HER3 targeting agent includes a bispecific antibody against HER3/HER2 such as MM-111 or MCLAO-128, or against IGF-1R/HER3 such as MM-141 (i.e., Istiratumab), and/or against HER1/HER3 such as MEHD7945A (i.e., Duligotumab).

Aspect 42. A method for treating a proliferative disease or disorder, the method including: diagnosing the subject with HER3-positive cells; and if the subject has HER3-positive cells, administering to the subject a therapeutically effective amount of an HER3 targeting agent according to any of the methods of aspects 1 to 41.

Aspect 43. The method according to aspect 42, wherein the diagnosing includes obtaining a sample of blood or tissue from the subject; mounting the sample on a substrate; and detecting the presence or absence of HER3 antigen using a diagnostic antibody, wherein the diagnostic antibody includes an antibody against HER3 labeled with a radiolabel such as $^{3}$H, $^{14}$C, $^{32}$P, $^{35}$S, and $^{1257}$I; fluorescent or chemiluminescent compounds, such as fluorescein isothiocyanate, rhodamine, or luciferin; or an enzyme, such as alkaline phosphatase, β-galactosidase, or horseradish peroxidase.

Aspect 44. The method according to aspect 42, wherein the diagnosing includes administering a HER3 targeting agent to the subject, wherein the HER3 targeting agent includes a radiolabel selected from the group including $^{18}$F, $^{11}$C, $^{68}$Ga, $^{64}$Cu, $^{89}$Zr, $^{124}$I, $^{99m}$Tc, or $^{111}$In; waiting a time sufficient to allow the HER3 targeting agent to accumulate at a tissue site; and imaging the tissues with a non-invasive imaging technique to detect presence or absence of HER3-positive cells.

Aspect 45. The method according to aspect 44, wherein the non-invasive imaging technique includes positron emission tomography (PET imaging) for $^{18}F$, $^{11}C$, $^{68}Ga$, $^{64}Cu$, $^{89}Zr$, or $^{124}I$ labeled HER3 targeting agents or single photon emission computed tomography (SPECT imaging) for $^{99m}Tc$ or $^{111}In$ labeled HER3 targeting agents.

While various specific embodiments have been illustrated and described herein, it will be appreciated that various changes can be made without departing from the spirit and scope of the invention(s). Moreover, features described in connection with one aspect of the invention may be used in conjunction with other aspects of the invention, even if not explicitly exemplified in combination within.

REFERENCES

Mishra R, Patel H, Alanazi S, Yuan L, Garrett J T. HER3 signaling and targeted therapy in cancer. Oncol Rev. 2018; 12(1).

Meneses-Lorente G, Friess T, Kolm I, et al. Preclinical pharmacokinetics, pharmacodynamics, and efficacy of RG7116: a novel humanized, glycoengineered anti-HER3 antibody. Cancer Chemother Pharmacol. 2015; 75(4): 837-850.

Mirschberger C, Schiller C B, Schraml M, et al. RG7116, a Therapeutic Antibody That Binds the Inactive HER3 Receptor and Is Optimized for Immune Effector Activation. Cancer Res. 2013; 73(16):5183-5194.

Meulendijks D, Jacob W, Martinez-Garcia M, et al. First-in-Human Phase I Study of Lumretuzumab, a Glycoengineered Humanized Anti-HER3 Monoclonal Antibody, in Patients with Metastatic or Advanced HER3-Positive Solid Tumors. Clin Cancer Res. 2016; 22(4):877-885.

Reynolds K L, Bedard P L, Lee S-H, et al. A phase I open-label dose-escalation study of the anti-HER3 monoclonal antibody LJM716 in patients with advanced squamous cell carcinoma of the esophagus or head and neck and HER2-overexpressing breast or gastric cancer. BMC Cancer. 2017; 17(1):646.

What is claimed is:

1. A method for treating a solid cancer comprising HER3-positive cancer cells in a mammalian subject, the method comprising:

administering to a mammalian subject afflicted with a solid cancer comprising HER3-positive cancer cells a therapeutically effective amount of a radionuclide labeled HER3 targeting antibody comprising:

radionuclide labeled barecetamab; radionuclide labeled patritumab; radionuclide labeled seribantumab; radionuclide labeled lumretuzumab; radionuclide labeled elgemtumab;

a radionuclide labeled antibody comprising an immunoglobulin heavy chain variable region comprising a CDR-H1 comprising SEQ ID NO:15, a CDR-H2 comprising SEQ ID NO:16, and a CDR-H3 comprising SEQ ID NO:17, and an immunoglobulin light chain variable region comprising a CDR-L1 comprising SEQ ID NO:18, a CDR-L2 comprising SEQ ID NO:19, and a CDR-L3 comprising SEQ ID NO:20;

a radionuclide labeled antibody comprising an immunoglobulin heavy chain variable region comprising SEQ ID NO:21 and an immunoglobulin light chain variable region comprising SEQ ID NO:22; or a radionuclide labeled antibody comprising an immunoglobulin heavy chain amino acid sequence of SEQ ID NO:23 and an immunoglobulin light chain amino acid sequence of SEQ ID NO: 24.

2. The method of claim 1, wherein the radionuclide labeled HER3 targeting antibody comprises $^{225}Ac$ as a radionuclide label.

3. The method of claim 1, wherein the radionuclide labeled HER3 targeting antibody comprises a humanized antibody against HER3.

4. The method of claim 1, wherein the radionuclide labeled HER3 targeting antibody comprises one or more of barecetamab, patritumab, seribantumab, lumretuzumab, and elgemtumab.

5. The method of claim 1, wherein the radionuclide labeled HER3 targeting antibody comprises a monoclonal antibody comprising:

(i) an immunoglobulin heavy chain variable region comprising a CDR-H1 comprising SEQ ID NO:15, a CDR-H2 comprising SEQ ID NO: 16, and/or a CDR-H3 comprising SEQ ID NO:17, and an immunoglobulin light chain variable region comprising a CDR-L1 comprising SEQ ID NO:18, a CDR-L2 comprising SEQ ID NO:19, and/or a CDR-L3 comprising SEQ ID NO:20;

(ii) an immunoglobulin heavy chain variable region comprising SEQ ID NO:21 and an immunoglobulin light chain variable region comprising SEQ ID NO: 22; or (iii) an immunoglobulin heavy chain amino acid sequence of SEQ ID NO: 23 and an immunoglobulin light chain amino acid sequence of SEQ ID NO:24.

6. The method of claim 1, wherein the solid cancer is a breast cancer, gastric cancer, bladder cancer, cervical cancer, endometrial cancer, skin cancer, stomach cancer, testicular cancer, esophageal cancer, bronchioloalveolar cancer, prostate cancer, colorectal cancer, ovarian cancer, cervical epidermoid cancer, pancreatic cancer, lung cancer, renal cancer, head and neck cancer, or any combination thereof.

7. The method of claim 1, wherein the solid cancer is ovarian cancer, breast cancer, gastric cancer, pancreatic cancer, or any combination thereof.

8. The method of claim 1, wherein the effective amount of the radionuclide labeled HER3 targeting antibody is a maximum tolerated dose.

9. The method of claim 1, wherein the radionuclide labeled HER3 targeting agent is $^{225}Ac$-labeled, and the effective amount of the $^{225}Ac$-labeled HER3 targeting antibody comprises a dose of 0.1 to 50 μCi/kg body weight of the subject, or 0.1 to 5 μCi/kg body weight of the subject, or 5 to 20 μCi/kg subject body weight.

10. The method of claim 1, wherein the radionuclide labeled HER3 targeting antibody is $^{225}$Ac-labeled, and the effective amount of the $^{225}$Ac-labeled HER3 targeting agent comprises a dose of 2 μCi to 2mCi, or 2 μCi to 250 μCi, or 75 μCi to 400 μCi.

11. The method of claim 1, wherein the effective amount of the radionuclide labeled HER3 targeting antibody comprises a protein dose of less than 3 mg/kg body weight of the subject, such as from 0.001 mg/kg patient weight to 3.0 mg/kg patient weight, or from 0.005 mg/kg patient weight to 2.0 mg/kg patient weight, or from 0.01 mg/kg patient weight to 1 mg/kg patient weight, or from 0.1 mg/kg patient weight to 0.6 mg/kg patient weight, or 0.3 mg/kg patient weight, or 0.4 mg/kg patient weight, or 0.5 mg/kg patient weight, or 0.6 mg/kg patient weight.

12. The method of claim 1, wherein the radionuclide labeled HER3 targeting antibody is administered according to a dosing schedule selected from the group consisting of once every 7, 10, 12, 14, 20, 24, 28, 36, and 42 days throughout a treatment period, wherein the treatment period includes at least two doses.

13. The method of claim 1, further comprising:

administering to the subject a therapeutically effective amount of a DNA damage response inhibitor (DDRi), a chemotherapeutic agent, or any combination thereof.

14. The method of claim 1, further comprising:

administering to the subject a therapeutically effective amount of an immune checkpoint therapy comprising an antibody against PD-1, PD-L1, CTLA-4, or any combination thereof.

15. The method of claim 1, wherein the radionuclide labeled HER3 targeting antibody comprises a chemically conjugated chelator group that chelates a radionuclide.

16. The method of claim 15, wherein the chelator group comprises DOTA.

17. The method of claim 1, wherein the administering step comprises:

administering to the subject a therapeutically effective amount of a therapeutic composition comprising a radiolabeled fraction of the HER3 targeting antibody and a non-radiolabeled fraction of the HER3 targeting antibody.

18. The method of claim 17, wherein the therapeutic composition further comprises at least one pharmaceutically acceptable excipient.

19. The method of claim 1, further comprising the step of: diagnosing the subject with HER3-positive cancer prior to the administering step.

20. The method of claim 19, wherein the diagnosing step comprises imaging HER3-positive cells in the subject using a radionuclide labeled HER3 targeting antibody.

21. The method of claim 1, wherein the radionuclide labeled HER3 targeting antibody is $^{225}$Ac labeled p-SCN-Bn-DOTA conjugated barecetamab.

22. The method of claim 21, wherein the solid cancer is ovarian cancer, breast cancer, prostate cancer, non-small cell lung cancer, gastric cancer, or pancreatic cancer.

23. The method of claim 1, wherein the radionuclide labeled HER3 targeting antibody is $^{225}$Ac labeled p-SCN-Bn-DOTA conjugated patritumab.

24. The method of claim 23, wherein the solid cancer is ovarian cancer, breast cancer, prostate cancer, non-small cell lung cancer, gastric cancer, or pancreatic cancer.

25. The method of claim 1, wherein the radionuclide labeled HER3 targeting antibody is $^{225}$Ac labeled p-SCN-Bn-DOTA conjugated seribantumab.

26. The method of claim 25, wherein the solid cancer is ovarian cancer, breast cancer, prostate cancer, non-small cell lung cancer, gastric cancer, or pancreatic cancer.

27. The method of claim 1, wherein the radionuclide labeled HER3 targeting antibody is $^{225}$Ac labeled p-SCN-Bn-DOTA conjugated lumretuzumab.

28. The method of claim 27, wherein the solid cancer is ovarian cancer, breast cancer, prostate cancer, non-small cell lung cancer, gastric cancer, or pancreatic cancer.

29. The method of claim 1, wherein the radionuclide labeled HER3 targeting antibody is $^{225}$Ac labeled p-SCN-Bn-DOTA conjugated elgemtumab.

30. The method of claim 29, wherein the solid cancer is ovarian cancer, breast cancer, prostate cancer, non-small cell lung cancer, gastric cancer, or pancreatic cancer.

31. The method of claim 1, wherein the radionuclide labeled HER3 targeting antibody is a $^{225}$Ac labeled p-SCN-Bn-DOTA conjugated antibody comprising an immunoglobulin heavy chain variable region comprising a CDR-H1 comprising SEQ ID NO:15, a CDR-H2 comprising SEQ ID NO: 16, and a CDR-H3 comprising SEQ ID NO:17, and an immunoglobulin light chain variable region comprising a CDR-L1 comprising SEQ ID NO:18, a CDR-L2 comprising SEQ ID NO:19, and a CDR-L3 comprising SEQ ID NO:20;

a $^{225}$Ac labeled p-SCN-Bn-DOTA conjugated antibody comprising an immunoglobulin heavy chain variable region comprising SEQ ID NO:21 and an immunoglobulin light chain variable region comprising SEQ ID NO:22; or a $^{225}$Ac labeled p-SCN-Bn-DOTA conjugated antibody comprising an immunoglobulin heavy chain amino acid sequence of SEQ ID NO:23 and an immunoglobulin light chain amino acid sequence of SEQ ID NO:24.

32. The method of claim 31, wherein the solid cancer is ovarian cancer, breast cancer, prostate cancer, non-small cell lung cancer, gastric cancer, or pancreatic cancer.

* * * * *